US009809863B2

(12) United States Patent
Chandriani et al.

(10) Patent No.: US 9,809,863 B2
(45) Date of Patent: Nov. 7, 2017

(54) FLAVIVIRUS ASSOCIATED WITH THEILER'S DISEASE

(71) Applicant: Elanco Tiergesundheit AG, Indianapolis, IN (US)

(72) Inventors: Sanjay Chandriani, Emeryville, CA (US); Peter Skewes-Cox, Emeryville, CA (US); Amy Kistler, Emeryville, CA (US); Bud Tennant, Ithaca, NY (US); Thomas Divers, Ithaca, NY (US)

(73) Assignees: ELANCO TIERGESUNDHEIT AG, Basel (CH); CORNELL UNIVERSITY, Ithaca, NY (US)

( * ) Notice: Subject to any disclaimer, the term of this patent is extended or adjusted under 35 U.S.C. 154(b) by 415 days.

(21) Appl. No.: 14/439,238

(22) PCT Filed: Oct. 31, 2013

(86) PCT No.: PCT/US2013/067669
§ 371 (c)(1),
(2) Date: Apr. 29, 2015

(87) PCT Pub. No.: WO2014/070975
PCT Pub. Date: May 8, 2014

(65) Prior Publication Data
US 2015/0292042 A1    Oct. 15, 2015

Related U.S. Application Data

(60) Provisional application No. 61/721,858, filed on Nov. 2, 2012.

(51) Int. Cl.
*C12P 19/34* (2006.01)
*C12Q 1/70* (2006.01)
*C07K 14/005* (2006.01)

(52) U.S. Cl.
CPC ............ *C12Q 1/701* (2013.01); *C07K 14/005* (2013.01); *C12Q 1/706* (2013.01); *C12N 2770/24021* (2013.01); *C12N 2770/24022* (2013.01); *C12N 2770/24034* (2013.01); *C12Q 2600/158* (2013.01)

(58) Field of Classification Search
USPC .............................................. 435/6.12, 91.2
See application file for complete search history.

(56) References Cited

U.S. PATENT DOCUMENTS

| 4,683,195 | A | 7/1987 | Mullis et al. |
| 4,683,202 | A | 7/1987 | Mullis |
| 4,816,567 | A | 3/1989 | Cabilly et al. |
| 4,965,188 | A | 10/1990 | Mullis et al. |
| 5,035,996 | A | 7/1991 | Hartley |
| 5,545,806 | A | 8/1996 | Lonberg et al. |
| 5,545,807 | A | 8/1996 | Surani et al. |
| 5,569,825 | A | 10/1996 | Lonberg et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 5,854,033 | A | 12/1998 | Lizardi |
| 6,245,533 | B1 | 6/2001 | Goldstein et al. |
| 2004/0265897 | A1 | 12/2004 | Lizardi |
| 2009/0197254 | A1 | 8/2009 | Lee |
| 2014/0128447 | A1* | 5/2014 | Kapoor .................. C07K 16/10 514/44 A |

FOREIGN PATENT DOCUMENTS

| EP | 070685 | 1/1983 |
| WO | 1988006626 | 9/1988 |
| WO | 1990000594 | 1/1990 |
| WO | 1991013157 | 9/1991 |
| WO | 1992001796 | 2/1992 |
| WO | 1992021376 | 12/1992 |
| WO | 1994016108 | 7/1994 |
| WO | 2006081222 | 8/2006 |
| WO | 2006087574 | 8/2006 |

OTHER PUBLICATIONS

Oswald, "Guerison rapide de deux patients ayant presente un botulisme, apres administration d'antitoxines botuliques", Médecine et maladies infectieuses, 2011, pp. 44-46, vol. 41.
Pellestor, The peptide nucleic acids (PNAs), powerful tools for molecular genetics and cytogenetics, European Journal of Human Genetics, 2004, pp. 694-700, vol. 12.
Presta, "Antibody engineering", Current Opinion in Structural Biology, 1992, pp. 593-596, vol. 2.
Riechmann, "Reschaping human antibodies for therapy", Nature, 1988, pp. 325-327, vol. 332.
Remington, The Science and Practice of Pharmacy 21st Edition, 2009.
Sambrook, Molecular Cloning a Laboratory Manual Third Edition, 2001.
Sambrook, Molecular Cloning a Laboratory Manual Second Edition, 1989.
Scheerlinck, "Genetic adjuvants for DNA vaccines", Vaccine, 2001, pp. 2647-2656, vol. 19.
Silverman, "Multivalent avimer proteins evolved by exon shuffling of a family of human receptor domains", Nature Biotechnology, 2005, pp. 1555-1561, vol. 23, No. 12.
Singh, LNA (locked nucleic acids): synthesis and high-affinity nucleic acid recognition, Chem. Commun., 1998, pp. 455-456.
Skerra, "Alternative binding proteins: Anticalins—harnessing the structural plasticity of the lipocalin ligand pocket to engineer novel binding activities", The FEBS Journal, 2008, pp. 2677-2683, vol. 275.
Stumpp, "DARPins: A new generation of protein therapeutics", Drug Discovery Today, 2008, pp. 695-701, vol. 13, No. 15, 16.
Sullivan, "Development of a preventive vaccine for Ebola virus infection in primates", Letters to Nature, 2000, pp. 604-609, vol. 408.
Svanvik, "Light-Up probes: Thiazole Orange-Conjugated Peptide Nucleic Acid for

(56) References Cited

OTHER PUBLICATIONS

Thomson, "Targeting a Polyepitope Protein Incorporating Multiple Class II-Restricted Viral Epitopes to the Secretory/Endoctytic Pathway Facilitates Immune Recognition by CD4+ Cytotoxic T Lymphocytes: a Novel Approach to Vaccine Design", Journal of Virology, 1998, pp. 2246-2252, vol. 72, No. 3.
Todd, "DzyNA—PCR: Use of DNAzymes to Detect and Quantify Nucleic Acid Sequences in a Real-Time Fluorescent Format", Clinical Chemistry, 2000, pp. 625-630, vol. 46, No. 5.
Tyagi, "Molecular Beacons: Probes that Fluoresce upon Hybridization", Nature Biotechnology, 1996, pp. 302-308, vol. 14.
Velders, "Defined Flanking Spacers a nd Enhanced Proteolysis is Essential for Eradication of Established Tumors by an Epitope String DNA Vaccine", The Journal of Immunology, 2001, pp. 5366-5373, vol. 166.
Verhoeyen, "Reschaping Human Antibodies: Grafting and Antilysozyme Activity", Science, 1988, pp. 1534-1536, vol. 239.
Whitcombe, "Detection of PCR products using self-probing amplicons and fluorescence", Nature Biotechnology, 1999, pp. 804-807, vol. 17.
Widera, "Increased DNA Vaccine Delivery and Immunogenicity by Electroporation in Vivo", The Journal of Immunology, 2000, pp. 4635-4640, vol. 164.
Wu, "The Ligation Amplification Reaction (LAR)-Amplification of Specific DNA Sequences Using Sequential Rounds of Template-Dependent Ligation", Genomics, 1989, pp. 560-569, vol. 4.
Xiang, "Manipulation of the Immune Response to a Plasmid-Encoded Viral Antigen by Coinoculation with Plasmids Expressing Cytokines", Immunity, 1995, pp. 129-135, vol. 2.
Lizardi, "Mutation detection and single-molecule counting using isothermal rolling-circle amplication", Nature Genetics, pp. 225-232, vol. 19 (Jul. 1998).
Afonina, "Minor Groove Binder-Conjugated DNA Probes for Quantitative DNA Detection by Hybridization-Triggered Fluorescence", BioTechniques, 2002, pp. 940-949, vol. 32.
Amara, "Control of a Mucosal Challenge and Prevention of AIDS by a Multiprotein DNA/MVA Vaccine", Science, 2001, pp. 69-74, vol. 292.
Baner, "Signal amplification of padlock probes by rolling circle replication, Nucleic Acids Research", 1998, pp. 5073-5078, vol. 26 No. 22.
Barany, "Genetic disease detection and DNA amplification using cloned thermostable ligase", Proc Natl Acad Sci, 1991, pp. 189-193, vol. 88.
Boerner, "Production of Antigen-Specific Human Monoclonal Antibodies From In Vitro-Primed Human Splenocytes", The Journal of Immunology, 1991, pp. 86-95, vol. 147.
Brock, "*Thermus aquaticus* gen. n. and sp. n., a Non-sporulating Extreme Thermophile", Journal of Bacteriology, 1969, pp. 289-297, vol. 98 No. 1.
Caley, "Venezuelan equine encephalitis virus vectors expressing HIV-1 proteins: vector design strategies for improved vaccine efficacy", Vaccine, 1999, pp. 3124-3135, vol. 17.
Cardullo, "Detection of nucleic acid hybridization by nonradiative fluorescence resonance energy transfer", Proc. Natl. Acad. Sci., 1988, pp. 8790-9794, vol. 85.
Chandriani, "Identification of a previously undescribed divergent virus from the Flaviviridae family in an outbreak of equine serum hepatitis", PNAS, 2013, pp. E1407-E1415.
Cole, "The EBV-Hybridoma Technique and Its Application to Human Lung Cancer", Monoclonal Antibodies and Cancer Therapy, 1985, pp. 77-96.
Dubensky, "Delivery Systems for Gene-based Vaccines", Molecular Medicine, 2000, pp. 723-732, vol. 6 No. 9.
Ebersbach, "Affilin-Novel Binding Molecules Based on Human γ-β-Crystallin, an All B-Sheet protein", J. Mol. Biol., 2000, pp. 172-185, vol. 372.

Epstein, "Identification of GBV-D, a Novel GB-like Flavivirus from Old World Frugivorous Bats (*Peteropus giganteus*) in Bangladesh", PLoS Pathogens, 2010, pp. 1-8, vol. 6, No. 7.
Fiandaca, "Self-Reporting PNA/DNA Primers for PCR Analysis", Genome Research, 2001, pp. 609-613, vol. 11.
Fishwild, "High-avidity human IgGk monoclonal antibodies from a novel strain of minilocus transgenic mice", Nature Biotechnology, 1996, pp. 845-851, vol. 14.
Fraley, "New generation liposomes: the engineering of an efficient vehicle for intracellular delivery of nucleic acids", Trends Biochem Science, 1981, pp. 77-80.
French, "HyBeacon probes: a new tool for DNA sequence detection and allele discrimination", Molecular and Cellular Probes, 2001, pp. 363-374, vol. 15.
Goeddel, "Systems for Heterologous Gene Expression", Methods in Enzymology, 1990, pp. 3-7, vol. 185.
Grabulovski, "A Novel, Non-immunogenic Fyn SH3-derived Binding Protein with Tumor Vascular Targeting Properties", The Journal of Biological Chemistry, 2007, pp. 3196-3204, vol. 282, No. 5.
Hanke, "Enhancement of MHC class I-restricted peptide-specific T cell induction by a DNA prime/MVA boost vaccination regime", Vaccine, 1998, pp. 439-445, vol. 16, No. 5.
Harlow, Antibodies A Laboratory Manual, 1988.
Harlow, Using Antibodies A Laboratory Manual, 1998.
Hoogenboom, "By-passing Immunisation Human antibodies from Synthetic Repertoires of Germline Vh Gene Segments Rearranged in Vitro", J. Mol. Biol., 1992, pp. 381-388, vol. 227.
Huang, "Human Immunodeficiency Virus Type 1-Specific Immunity after Genetic Immunization Is Enhanced by Modification of Gag and Pol Expression", Journal of Virology, 2001, pp. 4947-4951, vol. 75, No. 10.
Innis, A Guide to Methods and Applications, PCR Protocols, 1990.
Iwasaki, "Enhanced CTL Responses Mediated by Plasmid DNA Immunogens Encoding Costimulatory Molecules and Cytokines", The Journal of Immunology, 1997, pp. 4591-4601, vol. 158.
Jones, "Replacing the complementarity-determining regions in a human antibody with those from a mouse", Letters to Nature, 1986, pp. 522-525, vol. 321.
Kim, "Modulation of amplitude and direction of in vivo immune responses by co-administration of cytokine gene expression cassettes with DNA immunogens", Eur. J. Immunol., 1998, pp. 1089-1103, vol. 28.
Kohler, "Continuous cultures of fused cells secreting antibody of predefined specificity", Nature, 1975, pp. 495-497, vol. 256.
Koide, "Antibody Mimics Based on the Scaffold of the Fibronectin Type III Domain", Methods in Molecular Biology, 2007, pp. 95-109, vol. 351.
Krehenbrink, "Artificial Binding Proteins (Affitins) as Probes for Conformational Changes in Secretin PulD", J. Mol. Biol., 2008, pp. 1058-1068, vol. 383.
Leitner, "Enhancement of Tumor-specific Immune Response with Plasmid DNA Replicon Vectors", Cancer Research, 2000, pp. 51-55, vol. 60.
Li, "A new class of homogeneous nucleic acid probes based on specific displacement hybridization", Nucleic Acids Research, 2002, pp. 1-9, vol. 30, No. 2.
Little, "Molecular Diagnostics and Genetics, Clinical Chemistry", 1999, pp. 777-784, vol. 45, No. 6.
Liu, "Gene-Based Vaccines", Molecular Therapy, 2000, pp. 497-500, vol. 1, No. 6.
Lonberg, "Human Antibodies from Transgenic Mice", Intern. Rev. Immunol., 1995, pp. 65-93, vol. 13.
Lonberg, "Antigen-specific human antibodies from mice comprising four distinct genetic modifications", Letters to Nature, 1994, pp. 856-859, vol. 368.
Marks, "By-Passing Immunization: Building High Affinity Human Antibodies by Chain Shuffling", Biotechnology, 1992, pp. 779-783, vol. 10.
Marks, "By-passing Immuniczation Human Antibodies from V-gene Libraries Displayed on Phage", J. Mol. Biol., 1991, pp. 581-597, vol. 222.

(56) References Cited

OTHER PUBLICATIONS

Martin, "Chronic hepatitis associated with GB virus B persistence in a tamarin after intrahepatic inoculation of synthetic viral RNA", PNAS, 2003, pp. 9962-9967, vol. 100, No. 17.
Morrison, "Success in specification", Nature, 1994, pp. 812-813, vol. 368.
Nazarenko, "A closed tube format for amplification and detection of DNA based on energy transfer", Nucleic Acids Research, 1997, vol. 25, No. 12.
Nazarenko, "Multiplex quantitative PCR using self-quenched primers labled with a single fluorophore", Nucleic Acids Research, 2002, vol. 30, No. 9.
Neuberger, "Generating high-avidity human Mabs in mice", Nature Biotechnology, 1996, p. 826, vol. 14.
Nixon, "Engineered protein inhibitors of proteases", Current Opinion in Drug Discovery & Development, 2006 pp. 261-268, vol. 9, No. 2.
Nutiu, "Tripartite molecular beacons", Nucleic Acids Research, 2002, vol. 30, No. 18.
Nygren, "Alternative binding proteins: Affibody binding proteins developed from a small three-helix bundle scaffold", FEBS Journal, 2008, pp. 2668-2676, vol. 275.
Oser, "Nonradioactive Assay of DNA Hybridization by DNA-Template-Mediated Formation of a Ternary TB III Complex in Pure Liquid Phase", Angew. Chem. Int. Ed. Engl, 1990, vol. 29, No. 10.
Oshima, "Description of *Thermus thermophilus* (Yoshida and Oshima) comb. nov., a Nonsporulating Thermophilic Bacterium from a Japanese Thermal Spa", International Journal of Systematic Bacteriology, 1974, pp. 102-112, vol. 24, No. 1.

\* cited by examiner

FLAVIVIRUS ASSOCIATED WITH THEILER'S DISEASE

The present application is a national phase entry under 35 U.S.C. §371 of International Patent Application PCT/US2013/067669, filed on Oct. 31, 2013 and published in English as International Patent Publication WO 2014/070975A1 on May 8, 2014, which claims benefit of priority to U.S. Patent Application Ser. No. 61/721,858, filed Nov. 2, 2012; all of which are incorporated by reference in their entirety.

FIELD OF THE DISCLOSURE

This disclosure relates to Theiler's disease-associated virus ("TDAV"), reagents relating thereto, and methods for detecting, using, and/or treating diseases associated with TDAV.

BACKGROUND OF THE DISCLOSURE

Theiler's disease is a fulminant hepatic disease affecting horses. The cause of Theiler's disease has not yet been elucidated and represents a significant problem related to the diagnosis and treatment of the disease. The disease has been associated with the antecedent administration of biologics of equine origin (e.g., botulinal antitoxin, tetanus antitoxin). A significant delay between exposure to biologics and the onset of acute hepatitis has been observed and the associated histopathologic lesions in the liver determined to be remarkably similar to those associated with acute human hepatitis A virus or hepatitis B virus infection.

SUMMARY OF THE DISCLOSURE

This disclosure describes a new virus that has now been linked to Theiler's disease (Theiler's disease-associated Virus ("TDAV")). TDAV was determined to be a member of the Flaviviridae family that includes hepatitis C virus (HCV), GB virus B, canine hepacvirus (CHV), and equine Non-Primate Hepacivirus (NPHV). This new virus, the genomic nucleotide sequence, amino acid sequence, as well as compositions and methods for preparing, using, and/or detecting the same are described herein. Also provided are reagents and methods for detecting TDAV within biological samples. Thus, this disclosure provides a solution to the problems relating to the detection, diagnosis, treatment and prevention of Theiler's disease.

TDAV is disclosed herein to comprise the nucleic acid and amino acid sequences of SEQ ID NOS.: 1, 2 and/or 3. Nucleic acid molecules comprising such nucleic acid sequences and/or encoding such amino acid sequences are described. Methods and reagents for detecting TDAV (which may also include TDAV-like viruses), in a sample (e.g., a biological sample such as whole blood (e.g., undiluted or processed), cord blood, plasma, serum, cord serum, saliva, lymphatic fluid, cerebrospinal fluid, urine, semen, pleural fluid, breast milk, sweat, ascites, a tissue sample e.g. liver, a food (e.g., meat) or beverage (e.g., milk) product, etc.) are also provided herein. Compositions comprising TDAV, nucleic acids, peptides, and/or polypeptides corresponding to TDAV are also disclosed. Other embodiments are also provided, as described herein.

BRIEF DESCRIPTION OF THE DRAWINGS

FIG. 3. Phylogenetic analysis of Flaviviridae based on polyprotein sequences. Multiple sequence alignments were generated using MUSCLE and a Neighbor-Joining phylogenetic tree with 100 bootstrap replicates was generated in MEGA5. TDAV in bold for emphasis. All branches are numbered starting at '*' and incremented clockwise (see Table S3 for key). Closer branch groups are labeled with range of sequence numbers; representative member of group listed in parenthesis with a thicker line illustrating branch for representative member. WNV=West Nile virus, DENV=Dengue virus 1, DV=Donggang virus, YFV=Yellow fever virus, MV=Modoc virus, TBEV=Tick-borne encephalitis virus, BVDV=Bovine viral diarrhea virus 1, TDAV=Theiler's disease-associated virus, GBV-(A-D)=GB virus (A-D), HCV=Hepatitis C virus genotype 1, NPHV=NPHV #1 (AFJ20709.1). '†' indicates nearly identical branches 8 and 9, corresponding to Tembusu virus and Duck flavivirus TA respectively.

FIG. 7. TDAV can cause chronic infection. TDAV was monitored in paired samples harvested during the outbreak and approximately one year later. Cycles to threshold ($C_t$) from the qRT-PCR TDAV diagnostic assay (primers EVT-146/147) are plotted on an inverted y-axis; a lower $C_t$ value represents a greater viral load. The diagnostic assays were performed in parallel on paired samples, permitting direct comparison of $C_t$ values.

DETAILED DESCRIPTION

Figure 1:
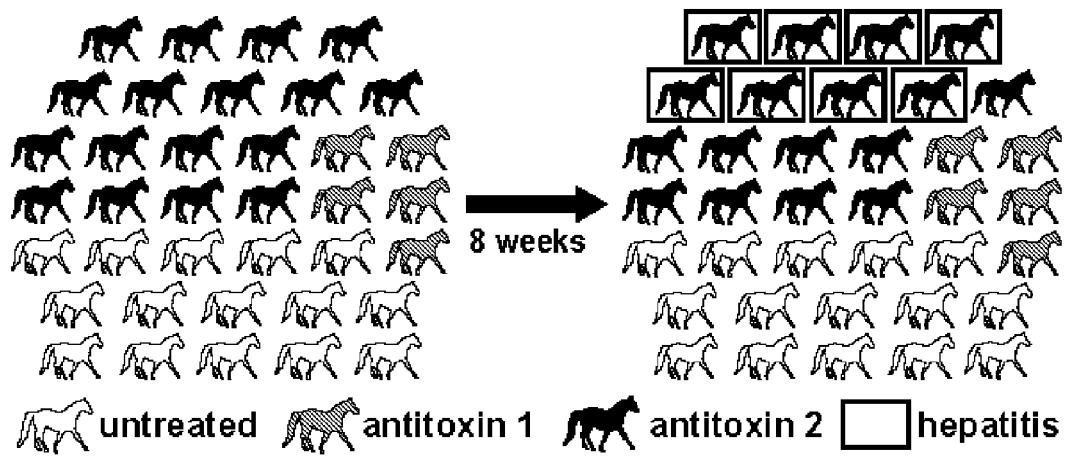
FIG. 1. Overview of a Theiler's disease outbreak. Twenty-two horses on Farm A suspected of exposure to botulinum toxin were therapeutically and prophylactically treated with intravenous equine anti-botulinum toxin hyperimmune plasma. Five horses received antitoxin from one source (grey horses, 'antitoxin 1'), while 17 horses received an independently sourced batch (black horses, 'antitoxin 2'). Fifteen horses followed in this study went untreated (white horses, 'untreated'). Within 8 weeks of antitoxin administration, 8 horses treated with Antitoxin 2 showed signs of acute hepatitis (boxes). All other horses were clinically asymptomatic (no boxes).

This disclosure relates to solutions to the current and unmet need for the identification and detection of the causitive agent(s) of diseases such as Theiler's Disease. As described herein, a possible causitive agent has been identified as Theiler's disease-associated virus (TDAV, which may include, for instance, "TDAV-like" viruses) as well as isolates and compositions thereof. Further provided are nucleic acid sequences and amino acid sequences representing the same (e.g., SEQ ID NOS.: 1-3). Nucleic acid molecules comprising such nucleic acid sequences and/or encoding such amino acid sequences are also provided. Methods and reagents for detecting TDAV (which may also include TDAV-like viruses), in a sample (e.g., a biological sample such as whole blood (e.g., undiluted or processed), cord blood, plasma, serum, cord serum, saliva, lymphatic fluid, cerebrospinal fluid, urine, semen, pleural fluid, breast milk, sweat, ascites, a tissue sample, a food (e.g., meat), beverage (e.g., milk) product, etc.), and/or organism (e.g., insect) are also provided herein. For instance, TDAV virus may be present in a biological sample of an animal (e.g., mammal) such as a horse. Such a horse (e.g., one having Theiler's disease) may have TDAV circulating in a bodily fluid such as, for instance, blood. In some embodiments, TDAV (e.g., a virus sharing at least some identity with that described herein) may be identified and/or detected by detecting and/or isolating the virus or a portion thereof from a biological sample. In some embodiments, TDAV may be detected by detecting a nucleic acid sequence and/or amino acid sequence of the virus, and/or the virus per se (e.g., as an intact virus or viral particle) in the biological sample. Other embodiments are also contemplated as will be clear to one of ordinary skill in the art from this disclosure.

TDAV typically comprises any one or more nucleic acid and/or amino acid sequences that correspond to, may be used to identify, and/or distinguish TDAV from another virus, and/or may be used to detect TDAV in a sample (e.g., a biological sample), and/or used to generate an antibody reactive with TDAV, such as, for example: SEQ ID NO.: 1 or 2 or a portion thereof; a nucleic acid sequence having at least about 50-99%, identity to SEQ ID NO.: 1 or 2 or a portion thereof; a nucleic acid sequence comprising at least any of five, six, seven, eight, nine, 10, 11, 12, 13, 14, 15, 16, 17, 18, 19, 20 or more consecutive nucleotides of SEQ ID NO.: 1 or 2 or a portion thereof; a nucleic acid sequence encoding SEQ ID NO.: 3 or a portion thereof; a nucleic acid sequence encoding a polypeptide or peptide having at least about 50-99% identity to SEQ ID NO.: 3 or a portion thereof; a nucleic acid sequence encoding at least three, four, five, six, seven, eight, nine, 10, 11, 12, 13, 14, 15, 16, 17, 18, 19, 20 or more consecutive amino acid residues of SEQ ID NO.: 3 or a portion thereof; a polypeptide comprising SEQ ID NO.: 3 or a portion thereof; a polypeptide having at least about 50-99% identity or similarity to SEQ ID NO.: 3 or a portion thereof; a peptide or polypeptide comprising at least three contiguous amino acids of SEQ ID NO.: 3 or a portion thereof, and the like. A suitable "portion of" SEQ ID NO.: 1, 2 or 3 may be, for example, any nucleotide sequence (e.g., an oligonucleotide) and/or amino acid sequence (e.g., a peptide or any amino acid sequence to which a binding agent (e.g., antibody) binds) of any number of nucleotides and/or amino acid residues that is specific to TDAV, may be used to identify TDAV, and/or may be used to differentiate TDAV from, for example, another virus in, for example, a biological sample (e.g., using an assay). The sequence of these nucleic acid sequences may be determined by any method available to those of ordinary skill in the art. Any of such nucleotide and/or amino acid sequences may be "unique to Theiler's disease-associated virus (TDAV)". "Used to identify" may include the use of a binding of a binding agent having specificity for a nucleotide and/or amino acid sequence of TDAV described herein. A virus comprising any such nucleotide (e.g., within the viral genome) and/or amino acid sequence (e.g., expressed by the virus) described herein and/or binding to a binding agent having specificity therefor may be referred to herein as a "TDAV-like" virus. In some instances herein, "TDAV" and "TDAV-like" may be used interchangeably. Assays for identifying TDAV (e.g., within a product) may be conducted in any manner set forth herein or otherwise available to one of ordinary skill in the art. For instance, the assay may include the use of one or more oligonucleotides, primer pair(s), method(s), kit(s), solid support(s), and/or antibodies described herein. Other embodiments of such products are also contemplated as will be clear to one of ordinary skill in the art from this disclosure.

As described herein, Theiler's disease has been associated with the antecedent administration of biologics of equine origin (e.g., botulinal antitoxin, tetanus antitoxin, snake antitoxins, anti-thymocyte preparations, general colostral products and the like). It is therefore important to produce products that are known not to contain an infectious agent that may cause Theiler's disease. The reagents and methods described herein provide one of ordinary skill in the art to make such determinations. Accordingly, using the reagents and methods described herein (e.g., assays for detecting TDAV), one may provide a product (e.g., a biologic of equine origin such as botulinal antitoxin or tetanus antitoxin) that has been screened and/or assayed for the presence of a Theiler's disease-associated virus therein. In certain embodiments, the product may be derived from serum or plasma (e.g., horse serum or plasma). The product, for example, may be one screened and/or assayed to detect the presence of TDAV. A preferred "assayed product", for instance, may be one determined not to contain TDAV and/or to contain less TDAV than the original product.

TDAV may be detected as a viral particle per se or a portion thereof (e.g., nucleic acid sequence and/or antigen) may be detected using any of several well-known techniques. A viral particle may be detected by, for example, observing the virus directly (e.g., by electron microscopy), detecting cells expressing an antigen of the virus (e.g., by staining and/or flow cytometry), and/or detecting a nucleic acid molecule (e.g., a target nucleic acid sequence) corresponding to the virus. Other techniques for detecting TDAV in a sample are also available to those of ordinary skill in the art and are contemplated herein.

TDAV nucleic acid sequences (and/or oligonucleotides used to identify and/or detect such nucleic acid sequences) may include those that hybridize (e.g., under highly stringent and/or moderately stringent conditions) to all or any portion of a hybridization probe having a nucleotide sequence encoding a polypeptide of SEQ ID NO.: 3 or a portion thereof, such as SEQ ID NOS.: 1 or 2 (or a complement thereof). The hybridizing portion of the hybridizing nucleic acid is typically at least about five, six, seven, eight, nine, 10, 11, 12, 13, 14, 15, 16, 17, 18, 19, 20 nucleotides in length. The hybridizing portion is typically at least about 50%, 55%, 60%, 50-60%, 65%, 70%, 60-70%, 75% 80%, 70-80%, 85%, 90%, 80-90%, 95%, 95-99%, 97.5%, 99% or 100% identical to the nucleotide sequence to which it hybridizes. Hybridizing nucleic acids are useful, for example, as cloning probes, primers (e.g., PCR primer), and/or diagnostic probes. Nucleic acid duplex or hybrid stability is expressed as the melting temperature or $T_m$, which is the temperature at which a probe dissociates from a target DNA. This melting temperature is typically used to define the required stringency conditions. If sequences are identified that are related and substantially identical to the probe, rather than identical, then it is useful to first establish the lowest temperature at which only homologous hybridization occurs with a particular concentration of salt (e.g., SSC or SSPE). Assuming that a 1% mismatching results in a 1° C. decrease in $T_m$, the temperature of the final wash in the hybridization reaction is reduced accordingly (for example, if sequences having more than 95% identity are sought, the final wash temperature is decreased by 5° C.). In practice, the change in $T_m$ can be between 0.5 and 1.5° C. per 1% mismatch. Highly stringent conditions may involve hybridizing at 68° C. in 5×SSC/5×Denhardt's solution/1.0% SDS, and washing in 0.2×SSC/0.1% SDS at room temperature. Moderately stringent conditions may include washing in 3×SSC at 42° C. Salt concentrations and temperatures can be varied to achieve the optimal level of identity between the probe and the target nucleic acid. Additional guidance regarding such conditions is readily available in the art, for example, in Molecular Cloning: A Laboratory Manual, Third Edition by Sambrook et al., Cold Spring Harbor Press, 2001.

A nucleic acid sequence corresponding to (e.g., sharing at least some identity with) TDAV may also be a "target nucleic acid" and/or "target nucleic acid sequence" (which terms may be used interchangeably). A target nucleic acid sequence may be detected and/or identified and/or quantified by any of several techniques widely available in the art. The target nucleic acid sequence may, for example, correspond to SEQ ID NO.: 1 and/or encode any number of contiguous amino acid residues (e.g., at least any of 5, 6, 7, 8, 9, 10, 11, 12, 13, 14, 15, 16, 17, 18, 19, 20 or more consecutive amino acid residues) encoded thereby (e.g., the amino acid sequence encoded by nucleotides 618-10,479 of SEQ ID NO.: 1 (including stop codon GTG) and/or as in SEQ ID NO.: 2)) and/or a derivative thereof. In some embodiments, the target nucleic acid sequence may be at least about 50%, 55%, 60%, 50-60%, 65%, 70%, 60-70%, 75% 80%, 70-80%, 85%, 90%, 80-90%, 95%, 95-99%, 97.5%, 99% or 100% complementary (e.g., identical to or capable of binding to under, for instance, stringent nucleic acid hybridization conditions) to a portion of or over the entirely of nucleic acid sequence of TDAV (e.g., SEQ ID NO.: 1). The target nucleic acid sequence may comprise a region (e.g., a "target-specific region") that is, for instance, about 4-30, about 5-25, about 6-20, about 7-15, about 8-10, about 10-15, about 15-20, about 20-25, about 25-30, about 30-35, about 35-40, about 40-45, about 45-50 or more nucleotides in length.

The target nucleic acid sequence may be of any kind such as, for example, single- or double-stranded RNA, DNA, or a RNA/DNA hybrid, for example. In some embodiments, the target nucleic acid may be contained on a RNA (e.g., as in the case of simultaneous analysis of gene expression by RT-PCR) or DNA molecule (e.g., cDNA). Target nucleic acid preparation may be carried out in a manner appropriate for the particular detection process to be implemented, as would be known by those of ordinary skill in the art. For example, DNA or RNA nucleic acid molecules may be extracted from any type of sample (e.g., blood) and processed according to standard procedures. Typically, detection involves the use of a nucleic acid (e.g., an oligonucleotide (e.g., probe)) that hybridizes to and/or may be used to amplify (e.g., is specific for) a target nucleic acid sequence. In some embodiments, 1-1000 different oligonucleotides (e.g., any of 1, 2, 3, 4, 5, 6, 7, 8, 9, 10, 11-50, 51-100, 101-150, 151-200, 201-250, 251-300, 301-350, 351-400, 401-450, 451-500, 501-550, 551-600, 601-650, 651-700, 701-750, 751-800, 801-850, 851-900, 901-950, or 951-1000 oligonucleotides) may be used separately or together in a single or multiple reactions to detect and/or identify and/or detect one or more target nucleic acid sequences in a sample. Suitable, exemplary detection techniques may include northern blot and/or polymerase chain reaction and/or variations thereof. Other techniques may also be utilized as may be described herein or elsewhere.

A commonly used technique for detecting nucleic acids involves amplification of one or more target nucleic acids (which may or may not also include one or more non-target nucleic acids) prior to detection and/or identification. Any amplification and/or detection method may be used. The method used to amplify the target nucleic acid(s) may be chosen from any one or more methods available to one of skill in the art including but not limited to linear, logarithmic, and/or any other amplification methods. While the term "amplifying" typically refers to an "exponential" increase in target nucleic acid (e.g., as in a polymerase chain reaction ("PCR")), the term may be used herein to describe both linear and exponential increases in the numbers of the target nucleic acid sequence(s). The term "amplification reaction mixture" typically refers to an aqueous solution comprising the various reagents used to amplify the target nucleic acid sequence(s) such as, for example, enzyme(s), aqueous buffer(s), salt(s), oligonucleotide(s) (e.g., amplification primer(s)), target nucleic acid, and nucleoside triphosphates. Depending upon the context, the mixture can be either a complete or incomplete amplification reaction mixture. Exemplary methods include polymerase chain reaction (PCR; see, e.g., U.S. Pat. Nos. 4,683,202; 4,683,195; 4,965,188; and/or 5,035,996), isothermal procedures (using one or more RNA polymerases (see, e.g., WO 2006/081222)), strand displacement (see, e.g., U.S. Pat. No. RE39007E), partial destruction of primer molecules (see, e.g., WO2006087574)), ligase chain reaction (LCR) (see, e.g., Wu, et al., Genomics 4: 560-569 (1990) and/or Barany, et al. PNAS USA 88:189-193 (1991)), Qβ RNA replicase systems (see, e.g., WO/1994/016108), RNA transcription-based systems (e.g., TAS, 3SR), rolling circle amplification (RCA) (see, e.g., U.S. Pat. No. 5,854,033; U.S. Pub. No. 2004/265897; Lizardi et al. Nat. Genet. 19: 225-232 (1998); and/or Barrer et al. Nucleic Acid Res., 26: 5073-5078 (1998)), and/or strand displacement amplification (SDA) (Little, et al. Clin Chem 45:777-784 (1999)), among others. In some embodiments, such as while carrying out PCR, the melting temperature (e.g., $T_m$) of the target nucleic acid sequence (or region thereof, e.g., a "target specific region") may be about 5° C. below the anneal/extend temperature used for PCR cycling. In some embodiments, the $T_m$ of the target specific region may range from about 51° C. to 60° C., about 52° C. to 59° C., about 53° C. to 58° C., about 54° C. to 57° C., about 55° C. to 56° C., or about 50° C. to about 60° C. Many systems are suitable for use in amplifying target nucleic acid sequences and are contemplated herein as would be understood by one of skill in the art.

In some embodiments, amplification may be accomplished by forming a reaction mixture containing the biological sample comprising nucleic acid of TDAV (or, e.g., a target nucleic acid thereof), a nucleic acid molecule such as a plasmid and/or oligonucleotide (optionally comprising a detectable label) corresponding to TDAV, and other reagents that may be required (e.g., buffers, enzymes (e.g., polymerase)) to amplify and/or detect and/or identify and/or quantify the target nucleic acid. In some embodiments, these methods may involve isolating and/or amplifying the target nucleic acid, and detecting the same using an oligonucleotide probe (e.g., an oligonucleotide corresponding to the nucleotide sequence of the TDAV-like virus described herein). For instance, for a PCR reaction, a pair of primers (a "forward" and a "reverse" primer) such as:

- AGGGTTCTTCGGGTAAATCC (EVT-146; SEQ ID NO.: 4) and CCCTCGGACTGAATTATAGGC (EVT-147; SEQ ID NO.: 5) to produce a 166 base pair amplicon (e.g., corresponding to nucleotides 171-336 of SEQ ID NO.: 1);
- GCTTTCCCTTTGCACTATGG (EVT-154; SEQ ID NO.: 6) and CAAGCCGATGCAACTAAAGC (EVT-155; SEQ ID NO.: 7) to produce a 156 base pair amplicon (e.g., corresponding to nucleotides 1674-1829 of SEQ ID NO.: 1);
- ATGCCATGGGTATGTTGACC (EVT-162; SEQ ID NO.: 10) and CTCCTCGTAGTTGCCTTTGC (EVT-163; SEQ ID NO.: 11) to produce a 155 base pair amplicon (e.g., corresponding to nucleotides 3892-4046 of SEQ ID NO.: 1);
- CTCCTGTGCTCCCTGAACC (EVT-178; SEQ ID NO.: 16) and AACACCATTGACCCAGAAGC (EVT-179; SEQ ID NO.: 17) to produce a 167 base pair amplicon (e.g., corresponding to nucleotides 7834-8000 of SEQ ID NO.: 1); or
- CTTCTGCCTACATCCCATCG (EVT-186; SEQ ID NO.: 18) and TGCATACCTTTCGGCTAAGG (EVT-187; SEQ ID NO.: 19) to produce a 197 base pair amplicon (e.g., corresponding to nucleotides 9931-10127 of SEQ ID NO.: 1).

Other potentially useful primer pairs that may include:

- GGCTCTTTGGATTCACTTGC (EVT-158; SEQ ID NO.: 8) and CCAGTGACCAGCATAATTCG (EVT-159; SEQ ID NO.: 9) to produce a 166 base pair amplicon (e.g., corresponding to nucleotides 2144-2309 of SEQ ID NO.: 1);
- TGGGAGTGTCTGGATTATTGC (EVT-170; SEQ ID NO.: 12) and CAAGGTGTCCGAGAGGTAGG (EVT-171; SEQ ID NO.: 13) to produce a 178 base pair amplicon (e.g., corresponding to nucleotides 5607-5784 of SEQ ID NO.: 1); or,
- TGGTACTGGTACCGTCACTGG (EVT-174; SEQ ID NO.: 14) and GCGAGGACCTGAAGTAGTGC (EVT-175; SEQ ID NO.: 15) to produce a 163 base pair amplicon (e.g., corresponding to nucleotides 6572-6734 of SEQ ID NO.: 1).

Other primer pairs corresponding to SEQ ID NO.: 1 and/or encoding a portion of SEQ ID NO.: 2 may also be useful. Such primer pairs may be used in amplification reactions as described herein and/or as is known in the art. Any of these primers may be also or alternatively be used alone or in combination with any other of such primers in other detection reactions (e.g., as oligonucleotide probes). Thus, a target nucleic acid sequence may also be identical to, be similar to, comprise, and/or correspond to any of SEQ ID NOS.: 4, 5, 6, 7, 8, 9, 10, 11, 12, 13, 14, 15, 16, 17, 18, or 19. The nucleotide sequences of SEQ ID NO.: 1 or 2 corresponding to any of the primers and/or amplicons referred to above may serve as target nucleic acids for other assays as well. Thus, a target nucleic acid may comprise and/or correspond to nucleotides 171-336 of SEQ ID NO.: 1 (SEQ ID NO.: 28); nucleotides 1674-1829 of SEQ ID NO.: 1 (SEQ ID NO.: 29); nucleotides 2144-2309 of SEQ ID NO.: 1 (SEQ ID NO.: 30); nucleotides 3892-4046 of SEQ ID NO.: 1 (SEQ ID NO.: 31); nucleotides 5607-5784 of SEQ ID NO.: 1 (SEQ ID NO.: 32); nucleotides 6572-6734 of SEQ ID NO.: 1 (SEQ ID NO.: 33); nucleotides 7834-8000 of SEQ ID NO.: 1 (SEQ ID NO.: 34); or nucleotides 9931-10127 of SEQ ID NO.: 1 (SEQ ID NO.: 35), as shown below:

SEQ ID NO.: 28

AGGGTTCTTCGGGTAAATCCCGGCGCGGTGTTTTGGGTTCAGGGCAGTAG

GGGCAGACGGGCCAGCAGTCGCTGGTTCCTGGTACCACCACCCTATCCGG

ACGACCTCCCTCACGAAAGGTCGCCACGGTCTGTGGCTCGACGACGCCTA

TAATTCAGTCCGAGGG;

SEQ ID NO.: 29

GCTTTCCCTTTGCACTATGGTCAGAAATCTACTGTTGCTTTGGCTACTAA

AATGGTCTTGACTGCTAAATTACAACCCTTGTGGAGGAATCTTAACACTA

CCATTATGTGCTCAGTTATTCGGACTTCTGTCCATTGCTTTAGTTGCATC

GGCTTG;

SEQ ID NO.: 30

GGCTCTTTGGATTCACTTGCGGGGGGGGGTCTTTGGATCCCCCACTCCGA

TACCTGGCTGCAAAAATAAGAATGAAGCCATCCACAACTACACACACTGT

GTCCAGGCTCTTGGTCACGCCATTAGCGTGGTTGGTGAGGCGAGTGCGAA

TTATGCTGGTCACTGG;

-continued

SEQ ID NO.: 31
ATGCCATGGGTATGTTGACCGCGGTGTCGCATCGGGGGCCGGAAGTACA

CTCGGCCCTCTTTGTCAAGCCGTGGGACAGCGTTCCCAGGGATGCCCAA

ACGGTTACGGACGTGGGTGCACCTCCTGCGGTACCTGGCAAAGGCAACT

ACGAGGAG;

SEQ ID NO.: 32
TGGGAGTGTCTGGATTATTGCTACCGGGTAGCGACCGGTACCCTGGCTCC

TAGAACCGCCGACGCGCTGGAAAGCGGGGCGCGTTGGCTTCGGGAGGCGT

GCTGTGGGACTAACCCTCCCACTAGTCCATTCCCAGGTGGGTGGGGGTC

ACCCAACCCCTACCTCTCGGACACCTTG;

SEQ ID NO.: 33
TGGTACTGGTACCGTCACTGGCCGTTGCGGCTGTGGCGCTGCCATCTCTG

CTGACTTCGAGGAGGGTGTTCGCGTTCGCTGGCACACTACTTCATATTTC

TGCCGTGGGTACTTTGCCCGCGGCATTCCTCTGAATACTCTTGGCACTAC

TTCAGGTCCTCGC;

SEQ ID NO.: 34
CTCCTGTGCTCCCTGAACCCCAGGTGCGGGTTGTGCACTTGACTGCTCCT

TGTTTCAATCATGATGGGGATGTTCTTTGTACTTCGGCTGACATCACCTT

GGCCGGAGTTTTGGTGCATGCCGGGGGGCGTTTTAACCACCGGCACAGCT

TCTGGGTCAATGGTGTT;
or,

SEQ ID NO.: 35
CTTCTGCCTACATCCCATCGTTGGAGGTTGACACCTTCGACGCAACCCAG

CTTTTGGACATTATGAGCAGGCCCTATAACAACCTTGAGCTCCAGATTGG

CAAGCCGATTCGTCGGTCGCTGACTGGACTCTTTGTGTCTAGGATCTGTT

CTTTTTTTGGTTCTGACATTCCTGCTACCTTAGCCGAAAGGTATGCA.

Variants of such target nucleic acids may also be suitable, as would other target nucleic acids that correspond to TDAV.

In some embodiments, the methods may involve preparing a sample of RNA and processing the same using a northern blot technique in which target nucleic acid is detected using an oligonucleotide probe that may include a detectable label. A suitable probe in a northern blot reaction may include any corresponding to TDAV such as, for instance, SEQ ID NO.: 3, which may include a detectable label. The types and/or amount of sample nucleic acid and/or primer and/or probe used in such reactions may vary as would be understood by one of ordinary skill in the art. For example, an amplification reaction may be performed using a nucleic acid polymerase (e.g., Taq polymerase), at least one oligonucleotide primer capable of specifically hybridizing to a target polynucleotide (typically two oligonucleotides as would be used in a polymerase chain reaction (PCR)) and, optionally, at least one (directly or indirectly) detectable oligonucleotide probe that hybridizes to the amplified target nucleic acid. A detectable label and/or probe may, for instance, be incorporated into the at least one oligonucleotide primer and/or probe. In some embodiments, at least one detectable nucleic acid binding agent (e.g., an intercalating or non-intercalating dye) may also be introduced before, during or after amplification. Any of these or other methods may be used to detect a TDAV in a sample as would be understood by one of ordinary skill in the art.

The oligonucleotide probe(s) described above may contain a detectable label that provides a signal that may be monitored to ascertain whether the target nucleic acid sequence has been amplified. Many different reagents, systems, and/or detectable labels may be used in the methods described herein. These include, for example, TaqMan® systems, detectable label-quencher systems (e.g., FRET, salicylate/DTPA ligand systems (see, e.g., Oser et al. Angew. Chem. Int. Engl. 29(10):1167 (1990), displacement hybridization, homologous probes, assays described in EP 070685), molecular beacons (e.g., NASBA), Scorpion, locked nucleic acid (LNA) bases (Singh, et al. Chem Commum 4:455-456 (1998)), peptide nucleic acid (PNA) probes (Pellestor, et al. European J. Human Gen. 12:694-700 (2004)), Eclipse probes (Afonina, et al. Biotechniques 32:940-949 (2002)), light-up probes (Svanvik, et al. Anal Biochem 281:26-35 (2001)), molecular beacons (Tyagi, et al. Nat. Biotechnol. 14:303-308 (1996)), tripartite molecular beacons (Nutiu, et al. Nucleic Acids Res. 30:e94 (2002)), QuantiProbes (www.qiagen.com), HyBeacons (French, et al. Mol. Cell. Probes 15:363-374 (2001)), displacement probes (Li, et al. Nucliec Acids Res. 30:e5 (2002)), Hyb-Probes (Cardullo, et al. PNAS 85:8790-8794 (1988)), MGB Alert (www.nanogen.com), Q-PNA (Fiandaca, et al. Genome Res. 11:609-611 (2001)), Plexor (www.Promega-.com), LUX primers (Nazarenko, et al. Nucleic Acids Res. 30:e37 (2002)), Scorpion primers (Whitcombe, et al. Nat Biotechnol 17:804-807 (1999)), AmpliFluor (Sunrise) primers (Nazarenko, et al. Nucleic Acids Res. 25:2516-2521 (1997)), DzyNA primers (Todd, et al. Clin. Chem. 46:625-630 (2000)), and the like. In each of these assays, the generation of amplification products may be monitored while the reaction is in progress. An apparatus for detecting the signal generated by the detectable label may be used to detect, measure, and quantify the signal before, during, and/or after amplification. The particular type of signal may dictate the choice of detection method. For example, in some embodiments, fluorescent dyes are used to label probes and/or amplified products. The probes may bind to single-stranded and/or double-stranded amplified products, and/or the dyes intercalate into the double-stranded amplified products, and consequently, the resulting fluorescence increases as the amount of amplified product increases. In some embodiments, the $T_m$ may be ascertained by observing a fluorescence decrease as the double-stranded amplified product dissociates and the intercalating dye is released therefrom. The amount of fluorescence may be quantitated using standard equipment such as a spectra-fluorometer, for example. One or more detectable labels and/or quenching agents may also be attached to a primer or probe. The detectable label may emit a signal when free or when bound to one the target nucleic acid. The detectable label may also emit a signal when in proximity to another detectable label. Detectable labels may also be used with quencher molecules such that the signal is only detectable when not in sufficiently close proximity to the quencher molecule. For instance, in some embodiments, the assay system may cause the detectable label to be liberated from the quenching molecule. Any one or more of such detectable labels may be used to label and/or detect the primers and/or probes used in the methods described herein. As mentioned above, in some embodiments the detectable label may be attached to a probe, which may be incorporated into a primer, or may otherwise bind to amplified target nucleic acid (e.g., a detectable nucleic acid binding agent such as an intercalating or non-intercalating dye). In some embodiments, the probe is an oligonucleotide that hybridizes to a target nucleic acid 3' relative to the at least one primer. In some embodiments, the polymerase has nuclease activity (e.g., 5'-3') for releasing the probe from the amplified nucleic acid. In some embodiments, release from the amplified nucleic acid renders the probe detectable. In some embodiments, the probe may have a detectable label and a quencher molecule that quenches the detectable label when free but does not quench when the probe is hybridized to the amplified nucleic acid. In some embodiments, two or more probes may be used where at least one probe has a detectable label and at least one other probe has a quencher molecule. When in sufficiently close proximity of one another, the quencher molecule typically suppresses the signal of the detectable label on the other probe. In some embodiments, two or more probes, each having a different detectable label, may be used without quencher molecules. In such embodiments, the probes may be rendered detectable (e.g., de novo or by exhibiting a different signal than either probe alone) when in sufficiently close proximity to one another. Such reactions may also be combined with other detection steps, such as melting temperature analysis and the like. When using more than one detectable label, each should differ in their spectral properties such that the labels may be distinguished from each other, or such that together the detectable labels emit a signal that is not emitted by either detectable label alone.

Exemplary detectable labels include, for instance, a fluorescent dye or fluorphore (e.g., a chemical group that can be excited by light to emit fluorescence or phosphorescence), "acceptor dyes" capable of quenching a fluorescent signal from a fluorescent donor dye, and the like. Suitable detectable labels may include, for example, fluorosceins (e.g., 5-carboxy-2,7-dichlorofluorescein; 5-Carboxyfluorescein (5-FAM); 5-HAT (Hydroxy Tryptamine); 5-Hydroxy Tryptamine (HAT); 6-JOE; 6-carboxyfluorescein (6-FAM); FITC); Alexa fluors (e.g., 350, 405, 430, 488, 500, 514, 532, 546, 555, 568, 594, 610, 633, 635, 647, 660, 680, 700, 750); BODIPY fluorophores (e.g., 4921515, 493/503, 500/510, 505/515, 530/550, 542/563, 558/568, 564/570, 576/589, 581/591, 630/650-X, 650/665-X, 665/676, FL, FL ATP, Fl-Ceramide, R6G SE, TMR, TMR-X conjugate, TMR-X, SE, TR, TR ATP, TR-X SE), coumarins (e.g., 7-amino-4-methylcoumarin, AMC, AMCA, AMCA-S, AMCA-X, ABQ, CPM methylcoumarin, coumarin phalloidin, hydroxycoumarin, CMFDA, methoxycoumarin), calcein, calcein AM, calcein blue, calcium dyes (e.g., calcium crimson, calcium green, calcium orange, calcofluor white), Cascade Blue, Cascade Yellow; Cy™ dyes (e.g., 3, 3.18, 3.5, 5, 5.18, 5.5, 7), cyan GFP, cyclic AMP Fluorosensor (FiCRhR), fluorescent proteins (e.g., green fluorescent protein (e.g., GFP. EGFP), blue fluorescent protein (e.g., BFP, EBFP, EBFP2, Azurite, mKalamal), cyan fluorescent protein (e.g., ECFP, Cerulean, CyPet), yellow fluorescent protein (e.g., YFP, Citrine, Venus, YPet), FRET donor/acceptor pairs (e.g., fluorescein/tetramethylrhodamine, IAEDANS/fluorescein, EDANS/dabcyl, fluorescein/fluorescein, BODIPY FL/BODIPY FL, Fluorescein/QSY7 and QSY9), LysoTracker and LysoSensor (e.g., LysoTracker Blue DND-22, LysoTracker Blue-White DPX, LysoTracker Yellow HCK-123, LysoTracker Green DND-26, LysoTracker Red DND-99, LysoSensor Blue DND-167, LysoSensor Green DND-189, LysoSensor Green DND-153, LysoSensor Yellow/Blue DND-160, LysoSensor Yellow/Blue 10,000 MW dextran), Oregon Green (e.g., 488, 488-X, 500, 514); rhodamines (e.g., 110, 123, B, B 200, BB, BG, B extra, 5-carboxytetramethylrhodamine (5-TAMRA), 5 GLD, 6-Carboxyrhodamine 6G, Lissamine, Lissamine Rhodamine B, Phallicidine, Phalloidine, Red, Rhod-2, 5-ROX (carboxy-X-rhodamine), Sulphorhodamine B can C, Sulphorhodamine G Extra, Tetramethylrhodamine (TRITC), WT), Texas Red, Texas Red-X, VIC and other labels described in, e.g., US Pub. No. 2009/0197254), among others as would be known to those of skill in the art. Other detectable labels may also be used (see, e.g., US Pub. No. 2009/0197254), as would be known to those of skill in the art. The use of other methods and/or reagents is also contemplated herein as would be understood by one of skill in the art.

Polymerase enzymes suitable for the practicing the methods described herein are well known in the art and can be derived from a number of sources. For instance, thermostable polymerases may be obtained from a variety of thermophilic bacteria that are commercially available (for example, from American Type Culture Collection, Rockville, Md.) using methods that are well-known to one of ordinary skill in the art (see, e.g., U.S. Pat. No. 6,245,533). Bacterial cells may be grown according to standard microbiological techniques, using culture media and incubation conditions suitable for growing active cultures of the particular species that are well-known to one of ordinary skill in the art (See, e.g., Brock, T. D., and Freeze, H., J. Bacteriol. 98(1):289-297 (1969); Oshima, T., and Imahori, K, Int. J. Syst. Bacteriol. 24(1):102-112 (1974)). Suitable sources of thermostable polymerases may include the thermophilic bacteria *Thermus aquaticus, Thermus thermophilus, Thermococcus litoralis, Pyrococcus furiosus, Pyrococcus woosii* and other species of the *Pyrococcus* genus, *Bacillus stearothermophilus, Sulfolobus acidocaldarius, Thermoplasma acidophilum, Thermus flavus, Thermus ruber, Thermus brockianus, Thermotoga neapolitana, Thermotoga maritima* and other species of the *Thermotoga* genus, and *Methanobacterium thermoautotrophicum*, and mutants of each of these species. Preferable thermostable polymerases can include, but are not limited to, Taq DNA polymerase, Tne DNA polymerase, Tma DNA polymerase, or mutants, derivatives or fragments thereof.

Sources of nucleic acids (e.g., target nucleic acids) in the compositions, methods and/or kits include, but are not limited to, biological samples (e.g., mammalian, non-mammalian) described herein. For instance, mammalian tissue, blood, cultured cells, and/or other culture samples (e.g., containing virus) may also be suitable sources of template nucleic acids. In addition, viruses, bacteriophage, bacteria, fungi and other micro-organisms may be the source of nucleic acid for analysis. The DNA may be genomic or it may be cloned in plasmids, bacteriophage, bacterial artificial chromosomes (BACs), yeast artificial chromosomes (YACs) or other vectors. RNA may be isolated directly from the relevant cells or it may be produced by in vitro priming from a suitable RNA promoter or by in vitro transcription. Other sources may also be suitable as would be understood by one of ordinary skill in the art.

Nucleic acid molecules corresponding to and/or derived from and/or encoding TDAV and/or an antigen (or immunogen) thereof may also be contained within a vector (e.g., a recombinant vector) such as one or more non-viral and/or viral vectors. In one embodiment, such a vector may be utilized to deliver such nucleic acid molecules (e.g., to a cell in vitro or in vivo). Where such vectors are used to induce and/or enhance an immune response, the vector may also encode other proteins (e.g., co-stimulatory molecules, cytokines or chemokines) and/or be combined with other factors (e.g., exogenous cytokines) (Xiang et al., *Immunity*, 2:129-135, 1995; Kim et al., *Eur. J. Immunol.*, 28:1089-1103, 1998; Iwasaki et al., *J. Immunol.* 158:4591-3601, 1997; Sheerlinck et al., *Vaccine*, 19:2647-2656, 2001). Other strategies may also be utilized to improve the efficiency of such delivery systems including, for example, the use of self-replicating viral replicons (Caley et al., *Vaccine*, 17:3124-2135, 1999; Dubensky et al., *Mol. Med.* 6:723-732, 2000; Leitner et al., *Cancer Res.* 60: 51-55, 2000), codon optimization (Liu et al., *Mol. Ther.*, 1:497-500, 2000; Dubensky, supra; Huang, et al., *J. Virol.* 75:4947-4951, 2001), in vivo electroporation (Widera et al., *J. Immunol.* 164:4635-3640, 2000), incorporation of stimulatory motifs such as CpG (Gurunathan, supra; Leitner, supra), sequences for targeting of the endocytic or ubiquitin-processing pathways (Thomson et al., *J. Virol.* 72:2246-2252, 1998; Velders et al., *J. Immunol.* 166:5366-5373, 2001), prime-boost regimens (Gurunathan supra; Sullivan et al., *Nature* 408:605-609, 2000; Hanke et al., *Vaccine*, 16:439-445, 1998; Amara et al., *Science* 292:69-74, 2001), proteasome-sensitive cleavage sites, and the use of mucosal delivery. "Non-viral" vectors may include, for instance, plasmid vectors (e.g., compatible with bacterial, insect, and/or mammalian host cells). Exemplary vectors may include, for example, PCR-ii, PCR3, and pcDNA3.1 (Invitrogen, San Diego, Calif.), pBSii (Stratagene, La Jolla, Calif.), pet15 (Novagen, Madison, Wis.), pGEX (Pharmacia Biotech, Piscataway, N.J.), pEGFp-n2 (Clontech, Palo Alto, Calif.), pETI (Bluebacii, Invitrogen), pDSR-alpha (PCT pub. No. WO 90/14363) and pFASTBACdual (Gibco-BRL, Grand island, NY) as well as Bluescript® plasmid derivatives (a high copy number COLe1-based phagemid, Stratagene Cloning Systems, La Jolla, Calif.), PCR cloning plasmids designed for cloning TAQ-amplified PCR products (e.g., TOPO™ TA Cloning® kit, PCR2.1® plasmid derivatives, Invitrogen, Carlsbad, Calif.). Bacterial vectors may also be used including, for instance, *Shigella*, *Salmonella* (e.g., for mucosal delivery), *Vibrio cholerae*, *Lactobacillus*, *Bacille Calmette Guérin* (BCG), and *Streptococcus* (see for example, WO 88/6626; WO 90/0594; WO 91/13157; WO 92/1796; and WO 92/21376). The vectors may be constructed using standard recombinant techniques widely available to one skilled in the art. Many other non-viral plasmid expression vectors and systems are known in the art and may be used. Various viral vectors that have been successfully utilized for introducing a nucleic acid to a host include retrovirus, adenovirus, adeno-associated virus (AAV), herpes virus, and poxvirus, among others. Viral vectors may be constructed using standard recombinant techniques widely available to one skilled in the art.

Other delivery techniques may also suffice including, for example, DNA-ligand complexes, adenovirus-ligand-DNA complexes, direct injection of DNA, CaPO$_4$ precipitation, gene gun techniques, electroporation, and colloidal dispersion systems. Colloidal dispersion systems include macromolecule complexes, nanocapsules, microspheres, beads, and lipid-based systems including oil-in-water emulsions, micelles, mixed micelles, and liposomes. The preferred colloidal system is a liposome, which are artificial membrane vesicles useful as delivery vehicles in vitro and in vivo. RNA, DNA and intact virions can be encapsulated within the aqueous interior and be delivered to cells in a biologically active form (Fraley, R. et al. *Trends Biochem. Sci.*, 6:77, 1981). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposomes include, for instance, phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

As would be understood by those of ordinary skill in the art, methods for preparing and using such non-viral vectors, viral vectors, and variations thereof are available in the art. For instance, useful techniques may be found in common molecular biology references such as *Molecular Cloning: A Laboratory Manual* (Sambrook et al., Cold Spring Harbor Laboratory Press, 1989), *Gene Expression Technology* (Methods in Enzymology, Vol. 185, edited by D. Goeddel, 1991. Academic Press, San Diego, Calif.), and *PCR Protocols: A Guide to Methods and Applications* (Innis et al., 1990. Academic Press, San Diego, Calif.), for instance.

TDAV polypeptides described herein may be the same as or similar to those specific to TDAV (e.g., SEQ ID NO.: 3 or a portion thereof), and may contain and/or be modified to contain substitutions that may be considered, for instance, conservative or non-conservative. A conservative substitution may be, for example, the substitution of one type of amino acid residue with a similar type of amino acid residue. A non-conservative substitution may be, for example, the substitution of one type of amino acid residue with a different type of amino acid residue. Amino acids may be similar to one another if, for example, based on size, hydrophobicity, polarity, aliphaticity (or not), aromaticity (or lack thereof), charge (positive or negative), or other attributes. Non-limiting, exemplary and preferred substitutions are shown in Table 1:

TABLE 1

Amino acid substitutions

| Original Residues | Exemplary Substitutions | Preferred Substitutions |
| --- | --- | --- |
| Ala | Val, Leu, Ile | Val |
| Arg | Lys, Gln, Asn, His | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A cultured cell comprising nucleic acid molecules corresponding to and/or derived from and/or encoding TDAV and/or an antigen (or immunogen) thereof may also be provided. The cultured cell may be transfected and/or infected by a vector or progeny thereof such that the may express a polypeptide (e.g., an antigen). Suitable cell lines are known to those of skill in the art and are commercially available, for example, through established cell culture collections. Such cells may then be used to produce viral particles, polypeptides, reagents for detecting and/or isolating TDAV, or for other uses. An exemplary method may comprise culturing a cell comprising the nucleic acid molecule (e.g., optionally under the control of an expression sequence) under conditions that allow for the production of viral particles or expression a polypeptide. The viral particle, polypeptide and/or other reagent may then be isolated from the cell or the cell culture medium using standard techniques.

Binding agents reactive with antigens of TDAV are also provided. For example, an antigen of TDAV may include any minimum number of contiguous amino acid residues (e.g., 5, 6, 7, 8, 9, 10, 11, 12, 13, 14, 15, 16, 17, 18, 19, 20 or more) of SEQ ID NO.: 3 (and/or encoded by SEQ ID NO.: 1 and/or SEQ ID NO.: 2) unique to TDAV. The binding agent may therefore be utilized to identify, isolate and/or remove TDAV from a sample (e.g., a biological sample). As described above, in some embodiments, binding agents may be antibodies. The term "antibody" or "antibodies" may refer to whole or fragmented antibodies in unpurified or partially purified form (e.g., hybridoma supernatant, ascites, polyclonal antisera) or in purified form, or to derivatives of antibodies. A purified antibody may be one that is separated from at least about 50%, 60%, 75%, 90%, or 95% of the proteins with which it is initially found (e.g., as part of a hybridoma supernatant or ascites preparation). The antibodies may be of any suitable origin or form including, for example, murine (e.g., produced by murine hybridoma cells), or expressed as humanized antibodies, chimeric antibodies, human antibodies, and the like. For instance, antibodies may be of any suitable type including, for example, human (e.g., IgG (IgG1, IgG2, IgG3, IgG4), IgM, IgA (IgA1 and IgA2), IgD, and IgE), canine (e.g., IgGA, IgGB, IgGC, IgGD), chicken (e.g., IgA, IgD, IgE, IgG, IgM, IgY), goat (e.g., IgG), mouse (e.g., IgG, IgD, IgE, IgG, IgM), pig (e.g., IgG, IgD, IgE, IgG, IgM), rat (e.g., IgG, IgD, IgE, IgG, IgM) and/or a fragment and/or derivative thereof (e.g., as chimeric antibodies). Suitable derivatives may include, for example, an Fab, F(ab')$_2$, Fab' single chain antibody, Fv, single domain antibody, mono-specific antibody, bi-specific antibody, tri-specific antibody, multi-valent antibody, chimeric antibody, canine-human chimeric antibody, canine-mouse chimeric antibody, antibody comprising a canine Fc, humanized antibody, human antibody, caninized, CDR-grafted antibody, shark antibody, nanobody (e.g., antibody consisting of a single monomeric variable domain), camelid antibody (e.g., antibodies of members of the Camelidae family), microbody, intrabody (e.g., intracellular antibody), or mimetic. Mimetics may also include, for example, organic compounds that specifically bind TDAV virus or an antigen thereof such as, for example, an affibody (Nygren, et al., *FEBS J.* 275(11):2668-76, 2008), affilin (Ebersbach, et al., *J. Mol. Biol.* 372 (1):172-85, 2007), affitin (Krehenbrink et al., *J. Mol. Biol.* 383(5):1058-68, 2008), anticalin (Skerra, A., *FEBS J.* 275(11):2677-83, 2008), avimer (Silverman et al., *Nat. Biotechnol.* 23(12): 1556-61, 2005), DARPin (Stumpp et al., *Drug Discov. Today* 13(15-16):695-701, 2008), Fynomer (Grabulovski et al., *J. Biol. Chem.* 282(5):3196-3204, 2007), Kunitz domain peptide (Nixon et al., *Curr. Opin. Drug Discov. Devel.* 9(2):261-8, 2006), and/or a monobody (Koide et al., *Methods Mol. Biol.* 352:95-109, 2007). Other binding agents are also provided herein as would be understood by one of ordinary skill in the art.

Methods of preparing and utilizing various types of antibodies are well-known to those of skill in the art and would be suitable in practicing the present invention (see, for example, Harlow, et al. *Antibodies: A Laboratory Manual*, Cold Spring Harbor Laboratory, 1988; Harlow, et al., Using Antibodies: A Laboratory Manual, Portable Protocol No. 1, 1998; Kohler and Milstein, *Nature,* 256:495, 1975; Jones et al., *Nature,* 321:522-525, 1986; Riechmann et al., *Nature,* 332:323-329, 1988; Presta, Curr. Op. Struct. Biol. 2:593-596, 1992; Verhoeyen et al., *Science,* 239:1534-1536, 1988; Hoogenboom et al., *J. Mol. Biol.,* 227:381, 1991; Marks et al., *J. Mol. Biol.,* 222:581, 1991; Cole et al., *Monoclonal Antibodies and Cancer Therapy*, Alan R. Liss, p. 77, 1985; Boerner et al., *J. Immunol.,* 147(1):86-95, 1991; Marks et al., *Bio/Technology* 10, 779-783, 1992; Lonberg et al., *Nature* 368:856-859, 1994; Morrison, *Nature* 368:812-13, 1994; Fishwild et al., *Nature Biotechnology* 14, 845-51, 1996; Neuberger, *Nature Biotechnology* 14, 826, 1996; Lonberg and Huszar, *Intern. Rev. Immunol.* 13:65-93, 1995; as well as U.S. Pat. Nos. 4,816,567, 5,545,807, 5,545,806, 5,569,825, 5,625,126, 5,633,425, and 5,661,016). In certain applications, the antibodies may be contained within hybridoma supernatant or ascites and utilized either directly as such or following concentration using standard techniques. In other applications, the antibodies may be further purified using, for example, salt fractionation and ion exchange chromatography, or affinity chromatography using Protein A, Protein G, Protein A/G, and/or Protein L ligands covalently coupled to a solid support such as agarose beads, or combinations of these techniques. The antibodies may be stored in any suitable format, including as a frozen preparation (e.g., −20° C. or −70° C.), in lyophilized form, or under normal refrigeration conditions (e.g., 4° C.). When stored in liquid form, a suitable buffer such as Tris-buffered saline (TBS) or phosphate buffered saline (PBS) may be utilized.

Where the binding agent is an antibody, it may be identified with reference to the nucleotide and/or amino acid sequence corresponding to the variable and/or complementarity determining regions ("CDRs") thereof. For instance, an exemplary binding agent that is, is derived from, or is related to the monoclonal antibody that binds TDAV or antigen thereof may comprise a heavy and/or a light chain that each comprise one or more constant and/or variable regions. The variable regions typically comprise one or more CDRs that in large part determine the binding specificity of the antibody. These monoclonal antibodies may be identified by analysis of the nucleotide sequences encoding the variable regions. The monoclonal antibodies may also be identified by analysis of the amino acid sequences of (e.g., which may be encoded by the nucleotide sequences) the variable regions. The binding agent may also be a derivative of an antibody (of, for example, the monoclonal antibody 1E4, 1G10, and/or 1G1) such as, for example, an Fab, F(ab')$_2$, Fab' single chain antibody, Fv, single chain, mono-specific antibody, bi-specific antibody, tri-specific antibody, multi-valent antibody, chimeric antibody, canine-human chimeric antibody, canine-mouse chimeric antibody, antibody comprising a canine $F_c$, humanized antibody, human antibody, caninized, CDR-grafted antibody, shark antibody, nanobody (e.g., antibody consisting of a single monomeric variable domain), camelid antibody (e.g., antibodies members of the Camelidae family) microbody, intrabody (e.g., intracellular antibody), and/or de-fucosylated antibody and/or derivative thereof. Mimetics of binding agents and/or antibodies are also provided. The binding agent may also comprise a detectable label and/or function/effector moiety fixably attached thereto. Functional/effector moieties may include, for example, cytotoxic drugs or toxins, or active fragments thereof such as diphtheria A chain, exotoxin A chain, ricin A chain, abrin A chain, curcin, crotin, phenomycin, enomycin, among others. Functional moieties may also include radiochemicals. In one embodiment, the effector moieties may be fixably attached to the binding agents. In one example, the detectable labels are fixably attached to the binding agents by chemical bonds. In one example, the chemical bonds are covalent chemical bonds. In one example, the effector moieties are conjugated to the binding agents.

The skilled artisan has many suitable techniques available for using the binding agents (e.g., antibodies) described herein to identify biological samples containing proteins that bind thereto. For instance, antibodies may be utilized to isolate TDAV and/or an antigen thereof using, for example, immunoprecipitation or other capture-type assay. This well-known technique may be performed by attaching the antibody to a solid support or chromatographic material (e.g., a bead coated with Protein A, Protein G and/or Protein L), contacting a sample (e.g., a solution) either containing or believed to contain the TDAV and/or an antigen thereof (e.g., a biological sample such as blood) with the material such that the TDAV and/or an antigen thereof binds to the antibody, thereby separating it from other components in the sample. The bound TDAV and/or an antigen thereof may then be separated from the antibody and analyzed as desired. Similar methods for isolating TDAV and/or an antigen thereof using a binding agent are well-known in the art. The binding agents (e.g., antibodies) may also be utilized to detect, isolate, and/or remove TDAV and/or an antigen thereof within or from a biological sample. Assays such as, for example, flow cytometric analysis, ELISA, immunoblotting (e.g., western blot), in situ detection, immunocytochemistry, and/or immunohistochemistry may be utilized in such methods. Other uses for the binding agents described herein may also be suitable, as would many other methods and/or assay systems.

In certain embodiments, preparations and/or compositions comprising the TDAV viral particles, nucleic acids corresponding thereto (e.g., contained within a vector), polypeptides and/or peptides corresponding thereto, and/or binding agents thereof are also provided. For example, a preparation or composition may comprise, for example, a TDAV viral particle, nucleic acid, polypeptide, peptide, and/or binding agent as a partially purified (e.g., about any of 50%, 60%, 75%, 90%, 95% purity (e.g., w/w)) or purified (e.g., about 98-100% (w/w)) preparation or composition. Typically, such preparations include a buffer such as phosphate- or tris-buffered saline (PBS or TBS, respectively). The preparations may also be formulated to contain excipients, like stabilizers, for example. The TDAV viral particles, nucleic acids corresponding thereto (e.g., contained within a vector), polypeptides and/or peptides corresponding thereto, and/or binding agents thereof may also be combined with one or more pharmaceutically acceptable carriers prior to use (e.g., administration to a host). A pharmaceutically acceptable carrier may be a material that is not biologically or otherwise undesirable, e.g., the material may be administered to a cell and/or subject, without causing significant undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable pharmaceutical carriers and their formulations that may be suitable are available to those of ordinary skill in the art as described in, for example, *Remington's: The Science and Practice of Pharmacy*, 21$^{st}$ Edition, David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally from about 5 to about 8 or from about 7 to about 7.5. Other carriers include sustained-release preparations such as semipermeable matrices of solid hydrophobic polymers containing polypeptides or fragments thereof. Matrices may be in the form of shaped articles, e.g., films, liposomes or microparticles. It will be apparent to those persons skilled in the art that certain carriers may be more preferable depending upon, for instance, the route of administration and concentration of composition being administered. Pharmaceutical compositions may also include carriers, thickeners, diluents, buffers, preservatives, surface active agents, adjuvants, immunostimulants, in addition to the binding agent and/or nucleic acid. Pharmaceutical compositions may also include one or more active ingredients such as antimicrobial agents, antiinflammatory agents and anesthetics. Adjuvants may also be included in the immunuostimulatory compositions to stimulate or enhance the immune response. Non-limiting examples of suitable classes of adjuvants include those of the gel-type (e.g., aluminum hydroxide/phosphate ("alum adjuvants"), calcium phosphate, microbial origin (muramyl dipeptide (MDP)), bacterial exotoxins (cholera toxin (CT), native cholera toxin subunit B (CTB), *E. coli* labile toxin (LT), pertussis toxin (PT), CpG oligonucleotides, BCG sequences, tetanus toxoid, monophosphoryl lipid A (MPL) of, for example, *E. coli, Salmonella minnesota, Salmonella typhimurium,* or *Shigella exseri*), particulate adjuvants (biodegradable, polymer microspheres), immunostimulatory complexes (ISCOMs)), oil-emulsion and surfactant-based adjuvants (Freund's incomplete adjuvant (FIA), microfluidized emulsions (MF59, SAF), saponins (QS-21)), synthetic (muramyl peptide derivatives (murabutide, threony-MDP), nonionic block copolymers (L121), polyphosphazene (PCCP), synthetic polynucleotides (poly A:U, poly I:C), thalidomide derivatives (CC-4407/ACTIMID), RH3-ligand, or polylactide glycolide (PLGA) microspheres, among others. Metallic salt adjuvants such as alum adjuvants are well-known in the art as providing a safe excipient with adjuvant activity. The mechanism of action of these adjuvants are thought to include the formation of an antigen depot such that antigen may stay at the site of injection for up to 3 weeks after administration, and also the formation of antigen/metallic salt complexes which are more easily taken up by antigen presenting cells. In addition to aluminium, other metallic salts have been used to adsorb antigens, including salts of zinc, calcium, cerium, chromium, iron, and berilium. The hydroxide and phosphate salts of aluminium are the most common. Formulations or compositions containing aluminium salts, antigen, and an additional immunostimulant are known in the art. An example of an immunostimulant is 3-de-O-acylated monophosphoryl lipid A (3D-MPL). Other homologs and/or derivatives of any of these toxins may also suitable, provided that they retain adjuvant activity.

The TDAV viral particles, nucleic acids corresponding thereto (e.g., contained within a vector), polypeptides and/or peptides corresponding thereto, and/or binding agents may be used, for example, to stimulate an immune response against TDAV described herein in a host. In some embodiments, immunogenic compositions and vaccines comprising TDAV, antigen thereof (e.g., SEQ ID NO.: 2 or a fragment thereof), and/or nucleic acid corresponding thereto (e.g., SEQ ID NO.: 1 or a fragment thereof) may be used to treat diseases caused by or associated with the presence of TDAV in a host (e.g., an animal such as a horse). An immunological composition is one that, upon administration to a host (e.g., an animal such as a horse) induces or enhances an immune response directed against the antigen or immunogen (e.g., TDAV) contained within the composition. This response may include the generation of antibodies (e.g., through the stimulation of B cells) or a T cell-based response (e.g., a cytolytic response). These responses may or may not be protective or neutralizing. A protective or neutralizing immune response is one that may be detrimental to the cell containing or expressing the antigen (e.g., from which the antigen was derived) and beneficial to the host (e.g., by reducing or preventing tumor growth). As used herein, protective or neutralizing antibodies and/or cellular responses may be reactive to TDAV and/or an antigen thereof. An immunological composition that, upon administration to a host, results in a protective or neutralizing immune response may be considered a vaccine. Immunological compositions comprising at least one TDAV and/or antigen may also include one or more additional antigens.

Methods for treating disease caused by or associated with TDAV in a mammalian host by administering to the mammal at least one or more effective doses of one or more TDAV viral particles (e.g., inactivated), nucleic acids, polypeptides, peptides, and/or binding agents described herein are also provided. For instance, a TDAV viral particle (e.g., inactivated) or vector corresponding thereto, may be administered to a host in a suitable dose (e.g., about $10^4$, $10^5$, $10^6$, $10^7$ or $10^8$ viral particles) and dosing schedule (e.g., once, twice, or three times a day/week/month), as may be determined by one of ordinary skill in the art. A polypeptide and/or peptide may be administered to a host in a suitable dose (e.g., about 1-100 mg/kg body weight) and dosing schedule (e.g., once, twice, or three times a day/week/month), as may be determined by one of ordinary skill in the art. A binding agent may be administered in a suitable dosage (e.g., about 1-50 mg/kg of body weight), about 1 to about 30 mg/kg, or about 1 to about 15 mg/kg (e.g., about any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, or 40 mg/kg). In certain embodiments, these reagents may be administered via any route (e.g., intradermally, intravenously, orally, rectally) at one or more times. When multiple doses are administered, the doses may comprise about the same or different types and or amounts of reagent (e.g., in a prime-boost format). The doses may also be separated in time from one another by the same or different intervals. For instance, the doses may be separated by about any of 6, 12, 24, 36, 48, 60, 72, 84, or 96 hours, one week, two weeks, three weeks, one month, two months, three months, four months, five months, six months, seven months, eight months, nine months, 10 months, 11 months, 12 months, 1.5 years, 2 years, 3 years, 4 years, 5 years, or any time period before, after, and/or between any of these time periods. In some embodiments, the binding agents may be administered in conjunction with other agents (e.g., chemotherapeutic agents), as described above. Such other agents may be administered about simultaneously with the binding agents, or at a different time and/or frequency. Other embodiments of such methods may also be appropriate as could be readily determined by one of ordinary skill in the art. Generally, a dose has the effect of decreasing the number of TDAV viral particles in a mammal is called an effective dose. Methods for preparing and/or using such preparations are well-known in the art.

In some embodiments, methods for detecting cells comprising TDAV viral particles and/or antigens thereof using binding agents are provided. In certain embodiments, cells expressing TDAV antigen(s) on the cell surface in an animal (e.g., a horse), may be detected by contacting a test biological sample with a binding agent and detecting the same bound to the cells (e.g., using flow cytometry). In certain embodiments, the method may comprise comparing the amount of binding to the test biological sample or components thereof to the amount of binding to a control biological sample or components thereof, wherein increased binding to the test biological sample or components thereof relative to the control biological sample or components thereof indicates the presence of a lymphoma cell in the test biological sample. In some embodiments, the biological sample is equine blood. Such methods are also provided in an in vivo and/or in vitro format. In some embodiments, methods for decreasing the viability and/or number of TDAV viral particles in a host using such the nucleic acids and/or binding agents described herein are also provided.

To assist the skilled artisan in using the nucleic acids and/or binding agents described herein, the same may be provided in kit format. A kit including such nucleic acids and/or binding agents (e.g., antibodies) and optionally other components necessary for using the same to detect, isolate and/or remove TDAV and/or antigen in and/or from a biological sample (e.g., cell or fluid) thereof is also provided herein. The nucleic acids and/or binding agents of the kit may be provided in any suitable form, including frozen, lyophilized, or in a pharmaceutically acceptable buffer such as TBS or PBS. The kit may also include other reagents required for utilization of the antibodies in vitro or in vivo such as buffers (e.g., TBS, PBS), blocking agents (solutions including nonfat dry milk, normal sera, Tween-20 Detergent, BSA, or casein), and/or detection reagents (e.g., goat anti-mouse IgG biotin, streptavidin-HRP conjugates, allophycocyanin, B-phycoerythrin, R-phycoerythrin, peroxidase, and/or detectable label) and other labels and/or staining kits (e.g., ABC Staining Kit, Pierce). The kits may also include other reagents and/or instructions for using the antibodies in commonly utilized assays described above such as, for example, flow cytometric analysis, ELISA, immunoblotting (e.g., western blot), in situ detection, immunocytochemistry, immunohistochemistry. In one embodiment, the detectable labels may be fixably attached to the binding agents. In one example, the detectable labels are fixably attached to the binding agents by chemical bonds. In one example, the chemical bonds are covalent chemical bonds. In one example, the detectable labels are conjugated to the binding agents.

In one embodiment, the kit provides a monoclonal antibody against TDAV and/or an antigen thereof in purified form. The monoclonal antibody may be provided in biotinylated form either alone or along with an avidin-conjugated detection reagent (e.g., antibody). The kit may include fluorescently-labelled antibodies that may be used to directly detect TDAV and/or an antigen thereof. Buffers and the like required for using any of these systems are well-known in the art and may be prepared by the end-user or provided as a component of the kit. The kit may also include a solid support containing positive- and negative-control protein and/or tissue samples. For example, kits for performing spotting or western blot-type assays may include control cell or tissue lysates for use in SDS-PAGE or nylon or other membranes containing pre-fixed control samples with additional space for experimental samples. Kits for visualization of TDAV and/or an antigen thereof on slides may include pre-formatted slides containing control cell or tissue samples with additional space for experimental samples. As mentioned above, the binding agents described herein and/or derivatives thereof may also be incorporated into compositions for use in vitro or in vivo. Other embodiments are also provided as would be understood by one of ordinary skill in the art.

As described above, this disclosure relates to SEQ ID NO.: 1, 2 or 3, any portion thereof, any derivative thereof, and/or any virus or viral particle comprising any of SEQ ID NOS.: 1, 2 or 3, any portion thereof, and/or any derivative thereof. This disclosure relates to, for example, an isolated nucleic acid sequence comprising SEQ ID NO.: 1 or 2 or a portion thereof; an isolated nucleic acid sequence having at least 50-99% identity to SEQ ID NO.: 1 or 2 or a portion thereof; an isolated nucleic acid sequence comprising at least five, six, seven, eight, nine, 10, 11, 12, 13, 14, 15, 16, 17, 18, 19, 20 or more consecutive nucleotides of SEQ ID NO.: 1 or 2 or a portion thereof; an isolated nucleic acid sequence encoding SEQ ID NO.: 3 or a portion thereof; an isolated nucleic acid sequence encoding a polypeptide having at least 50-99% identity to SEQ ID NO.: 3 or a portion thereof; an isolated nucleic acid sequence encoding at least at least three, four, five, six, seven, eight, nine, 10, 11, 12, 13, 14, 15, 16, 17, 18, 19, 20 or more consecutive amino acids of SEQ ID NO.: 3 or a portion thereof; a polypeptide comprising SEQ ID NO.: 3 or a portion thereof; a polypeptide having at least 50-99% identity or similarity to SEQ ID NO.: 3 or a portion thereof; a peptide or polypeptide comprising at least at least three, four, five, six, seven, eight, nine, 10, 11, 12, 13, 14, 15, 16, 17, 18, 19, 20 or more consecutive contiguous amino acids of SEQ ID NO.: 3, optionally comprising a conservative and/or non-conservative substitution therein; an expression vector comprising or encoding SEQ ID NO.: 1, 2 and/or 3, and/or a complementary or similar (e.g., 50-99% identical) nucleic acid sequence, and/or a similar (e.g., 50-99% identical) amino acid sequence; a host cell comprising or encoding SEQ ID NO.: 1, 2 and/or 3, and/or a complementary or similar nucleic acid sequence, and/or a similar amino acid sequence; an oligonucleotide having a nucleic acid sequence hybridizable under highly or moderately stringent conditions to SEQ ID NO.: 1 or 2 or a portion thereof, complementary to a fragment of SEQ ID NO.: 1 or 2 or a portion thereof, corresponding to a nucleic acid sequence encoding at least a portion of SEQ ID NO.: 3, or complementary to a nucleic acid sequence encoding at least a portion of SEQ ID NO.: 3; an oligonucleotide corresponding to or complementary to at least portion of SEQ ID NO.: 1 or 2; an oligonucleotide selected from the group consisting of SEQ ID NO.: 1, SEQ ID NO.: 2, SEQ ID NO.: 3, SEQ ID NO.: 4, SEQ ID NO.: 5, SEQ ID NO.: 6, SEQ ID NO.: 7, SEQ ID NO.: 8, SEQ ID NO.: 9, SEQ ID NO.: 10, SEQ ID NO.: 11, SEQ ID NO.: 12, SEQ ID NO.: 13, SEQ ID NO.: 14, SEQ ID NO.: 15, SEQ ID NO.: 16, SEQ ID NO.: 17, SEQ ID NO.: 18, and SEQ ID NO.: 19; an oligonucleotide comprising nucleotides encoding at least a portion of SEQ ID NO.: 3, optionally comprising one or more detectable labels; two or more oligonucleotides for amplifying a nucleic acid sequence of a virus (e.g., TDAV), each oligonucleotide comprising a nucleic acid sequence corresponding to at least a portion of SEQ ID NO.: 1 or 2, complementary to at least a portion of SEQ ID NO.: 1 or 2, corresponding to a nucleic acid sequence encoding at least a portion of amino acids of SEQ ID NO.: 3, or complementary to a nucleic acid sequence encoding a portion of SEQ ID NO.: 3, optionally comprising one or more detectable labels; a primer pair selected from the group consisting of SEQ ID NOS.: 4 and 5; SEQ ID NOS.: 6 and 7; SEQ ID NOS.: 8 and 9; SEQ ID NOS.: 10 and 11; SEQ ID NOS.: 12 and 13; SEQ ID NOS.: 14 and 15; SEQ ID NOS.: 16 and 17; and SEQ ID NOS.: 18 and 19, optionally comprising one or more detectable labels; methods for detecting and/or identifying and/or quantifying a virus (e.g., TDAV) in a sample (e.g., a biological sample such as serum), comprising amplifying from the sample a nucleic acid corresponding to TDAV; a kit for the detection of nucleic acid of a virus in a sample, the kit comprising an oligonucleotide, oligonucleotides, and/or primer pair for detecting and/or identifying and/or quantifying TDAV, the kit further optionally comprising a solid support, and/or one or more amplification reagents; a composition comprising a pharmaceutically acceptable carrier and a nucleic acid or complement thereof and/or a peptide and/or polypeptide corresponding to TDAV (which may be an immunogenic composition and/or a vaccine); a method of producing a nucleic acid molecule, peptide and/or polypeptide corresponding to TDAV, the method comprising transfecting a host cell with an expression vector encoding the peptide or polypeptide, culturing the host cell such that nucleic acid molecule, peptide and/or polypeptide is expressed, and isolating the peptide or polypeptide; a method of eliciting an immune response in a mammal by administering to the mammal a pharmaceutical composition comprising a nucleic acid molecule, peptide, and/or polypeptide corresponding to TDAV, and/or host cell comprising or expressing the same; a method of generating a binding agent (e.g., antibody) against a nucleic acid, peptide and/or polypeptide corresponding to TDAV and the binding agent(s) produced thereby (e.g., reactive with a polypeptide encoded by SEQ ID NO.: 1 or 2, a fragment of at least 9 nucleotides thereof). Other embodiments are also provided by this disclosure as would be recognized by one of ordinary skill in the art.

Any indication that a feature is optional is intended provide adequate support for claims that include closed or exclusive or negative language with reference to the optional feature. Exclusive language specifically excludes the particular recited feature from including any additional subject matter. For example, if it is indicated that A can be drug X, such language is intended to provide support for a claim that explicitly specifies that A consists of X alone, or that A does not include any other drugs besides X. "Negative" language explicitly excludes the optional feature itself from the scope of the claims. For example, if it is indicated that element A can include X, such language is intended to provide support for a claim that explicitly specifies that A does not include X. Non-limiting examples of exclusive or negative terms include "only," "solely," "consisting of," "consisting essentially of," "alone," "without", "in the absence of (e.g., other items of the same type, structure and/or function)" "excluding," "not including", "not", "cannot," or any combination and/or variation of such language.

All publications and patents cited in this specification are herein incorporated by reference as if each individual publication or patent were specifically and individually indicated to be incorporated by reference. Genbank records referenced by GID or accession number, particularly any polypeptide sequence, polynucleotide sequences or annotation thereof, are incorporated by reference herein. The citation of any publication is for its disclosure prior to the filing date and should not be construed as an admission that the present invention is not entitled to antedate such publication by virtue of prior invention.

Certain embodiments are further described in the following examples. These embodiments are provided as examples only and are not intended to limit the scope of the claims in any way.

EXAMPLES

Described below are the procedures utilized to isolate the genome of a novel virus termed "Theiler's disease-associated virus" (TDAV). The genome is presented as SEQ ID NO: 1; the amino acid coding sequence presented as SEQ ID NO.: 2; and the amino acid sequence is presented as SEQ ID NO.: 3.

A. Materials and Methods

1. RNA Extraction

Sera harvested from horses were stored at −80° C. RNA was extracted from 300 µl aliquots of stored sera using the TRIzol LS reagent (Life Technologies) as per the manufacturer's protocol. Briefly, 900 µl of TRIzol LS was added to 300 µl of sera; tube was shaken by hand; homogenized sample was incubated for 5 minutes (min) at room temperature; 0.24 ml of chloroform was added and shaken vigorously; sample was centrifuged at 12000×g for 15 min at 4° C.; the aqueous top phase was saved; 15 µg of GlycoBlue (Life Technologies) was added; 600 µl of 2-propanol was added; sample was incubated room temperature for 10 min; sample was centrifuged at 12000×g for 10 min at 4° C.; supernatant was discarded; RNA pellet was washed with 75% ethanol; pellet was dried and RNA was dissolved in 20 µl water. Extracted RNA samples were subjected to Turbo DNA-free (Life Technologies) treatment as per the manufacturer's protocol with one modification (include RNase inhibitor). Briefly, a mix of 2.9 µl Turbo DNase buffer, 5 µl H20, and 0.25 µl RNase Inhibitor (Life Technologies) was added to a 20 µl RNA sample; 1 µl Turbo DNase was added; sample was incubated at 37° C. for 20 min; 3 µl DNase inactivation reagent was added; sample was incubated at room temperature for 5 mM; sample was centrifuged at 10000×g for 1.5 min at room temperature; 21.5 µl of supernatant was saved for further analysis.

2. Library Preparation and Sequencing

Briefly, 4 µL of DNase-treated RNA was used as template for reverse transcription with the following conditions: 3Sol_N primer (final concentration, 8 uM) was mixed with RNA and denatured at 65° C. for 5 min before incubation on ice for 5 min. Superscript III reverse transcriptase (10 U/ul) reagents (Life Technologies) Superscript III buffer (1×), $MgCl_2$ (5 mM), DTT (10 mM), dNTP (500 µM), and RNaseOUT (0.4 U/µL), were added and sample was incubated at 42° C. for 60 min followed by 94° C. for 4 mM. For second strand synthesis, a 5 µL mix of Sequenase buffer (0.33×) and Sequenase 2.0 (0.13 U/µL) was added. Reaction temperature was ramped from 4° C. to 37° C. over 8 mM, then held at 37° C. for 8 min. In an initial PCR step, 5 µL of this cDNA was amplified with Klentaq LA DNA polymerase (0.1 U/µL) (Sigma) in Klentaq buffer (1×), dNTP (200 µM), and 3_Sol primer (2 mM), and PCR was performed under the following cycling conditions: 94° C. for 3 mM, 25 cycles [94° C. for 30 seconds (s), 40° C. for 1 min, 68° C. for 1 min], 68° C. for 7 min. A final 4-primer PCR used 10 ng of the initial PCR reaction as a template with Klentaq buffer (1×), dNTP (200 µM), SolM1 primer (10 nM), SolM2_barcode (10 nM), two oligos manufactured with the CleanAmp Precision™ modification (TriLink Bio-Technologies), 5SolM1_18 (200 nM), 5SolM2_19 (200 nM), and Klentaq LA DNA polymerase (0.1 U/µL). The following cycling conditions were used for this PCR step: 94° C. for 1 min, then two cycles [94° C. for 30 s, 40° C. for 30 s, 68° C. for 1 mM], 94° C. for 10 min, seven cycles [94° C. for 30 s, 58° C. for 30 s, 68° C. for 1 min], and 72° C. for 5 min. Resulting sequencing libraries were purified using DNA Clean & Concentrator-5 (Zymo Research) according to the manufacturer's protocol and eluted with 20 g, $H_2O$. Ten microliters of purified libraries were size selected (423 bp+/−7%) using LabChip XT (DNA 750 assay kit, Caliper/Perkin Elmer) and further purified by Zymo column. Individual library concentration were determined by qPCR using a PhiX control library (Illumina) with primers 1.1 and 2.1 and Fast SYBR Green Master Mix (Life Technologies), as per manufacturer's protocol. Libraries were then pooled in equimolar concentrations and re-quantified prior to sequencing. Paired-end sequencing (100 cycles for each paired end) on the HiSeq2000 (Illumina) with v3 cluster generation reagents and SBS reagents was performed as per manufacturer's instructions.

3. Illumina Sequencing

Paired-end sequencing (100 cycles for each paired end) was performed by first generating clusters on flow cell (FC) on the cBot as described in the "cBot User Guide" (Part #: 15006165 Rev. G, Illumina); the clustered FC was subjected to paired-end sequencing on the HiSeq200 as described in the "HiSeq 2000 User Guide" (Part#: 15011190 Rev. K, Illumina).

4. Sequencing Analysis

The initial FASTQ sequence data were binned by sequencing index for each of the three samples. Sequence read pairs for which one of the reads had 10 or more uncalled bases (Ns) were removed. Low complexity reads were identified by analyzing the size of the compressed Lempel-Ziv-Welch sequence string after removing Ns from the string to avoid artificial increases in complexity. Sequence read pairs for which one of the reads had a compressed size below 37 were removed. The remaining sequencing reads were aligned to the horse genome (EquCab2.0, GCF_000002305.2) (33) by nucleotide BLAST (blastn) with default word size and E value (11 and 10, respectively). Sequence read pairs for which one of the reads had at least 80/100 nucleotides (80% total read identity) mapping identically to the horse genome were considered host-derived and removed from downstream analysis. The remaining sequencing reads were aligned by both blastn and translated BLAST (blastx) to all RefSeq (March 2012) viral genomes and protein sequences, respectively, with default word size (11 for blastn, 3 for blastx) and E value (10 for both blastn and blastx). Sequences matching the viral database were isolated and considered candidates. To confirm viral origin in an unbiased context, candidate viral sequences were aligned to the non-redundant nucleotide database (NT; April 2012) by blastn using the default parameters. Candidate viral reads that did not have an alignment to NT were aligned to the non-redundant protein database (NR; April 2012) by blastx using the default parameters. Candidate viral reads whose highest-scoring alignments mapped only to viral genomes were deemed viral in origin.

5. Genome Assembly

All reads mapping to the Flaviviridae family from each of the three samples were consolidated into FASTA files representing the starting point for genome assemblies. These reads were used as seeds for a targeted metatranscriptomic assembly using an alpha version (v0.16.2) of the Paired-Read Iterative Contig Extension (PRICE) assembler software (http://derisilab.ucsf.edu/software/price/index.html). PRICE uses paired-end information to generate local assemblies that extend existing contigs; in this case, the initial contigs were reads with blastx matches to the Flaviviridae family, and the contigs were repeatedly extended through as many cycles as possible. In some cases, if an assembly stalled, the unfiltered sequence data were mapped to the existing assembly, and reads with high percent identity were culled in an effort to gather more high-quality seeds for further assembly.

6. Phylogenetic Analysis

Figure 3:
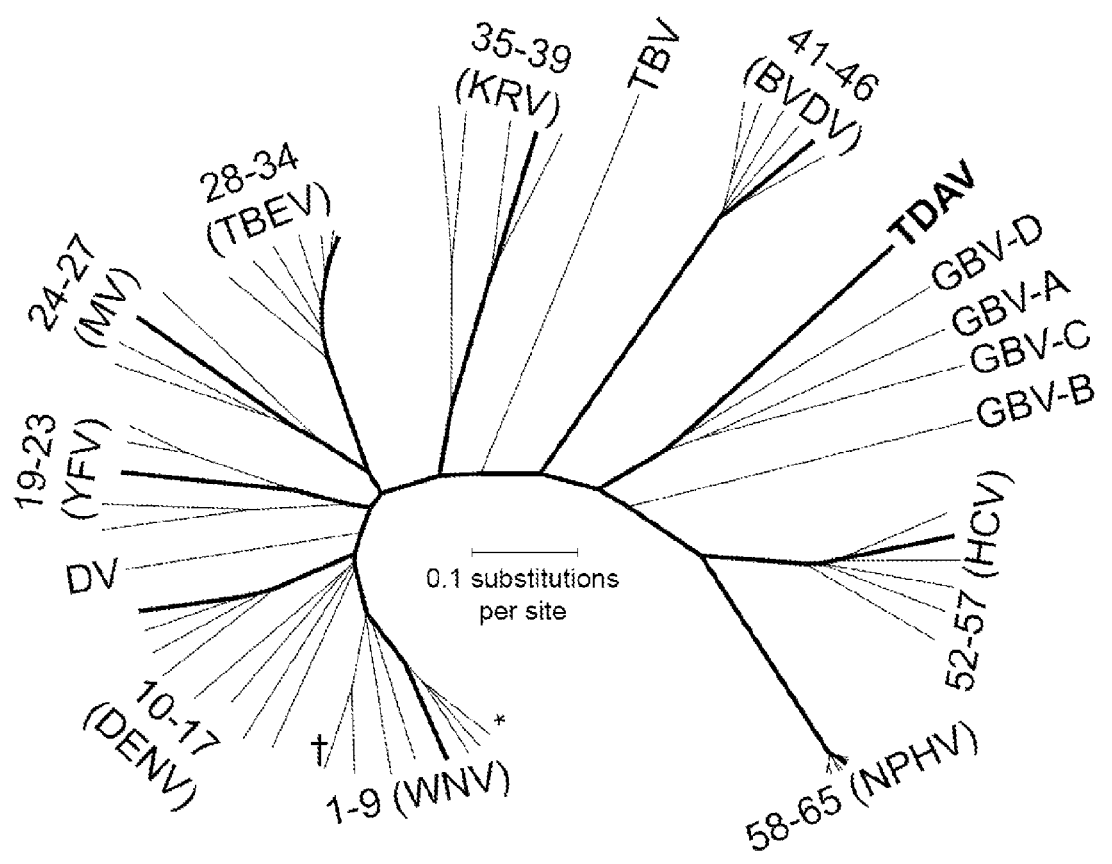
Figure 4A:
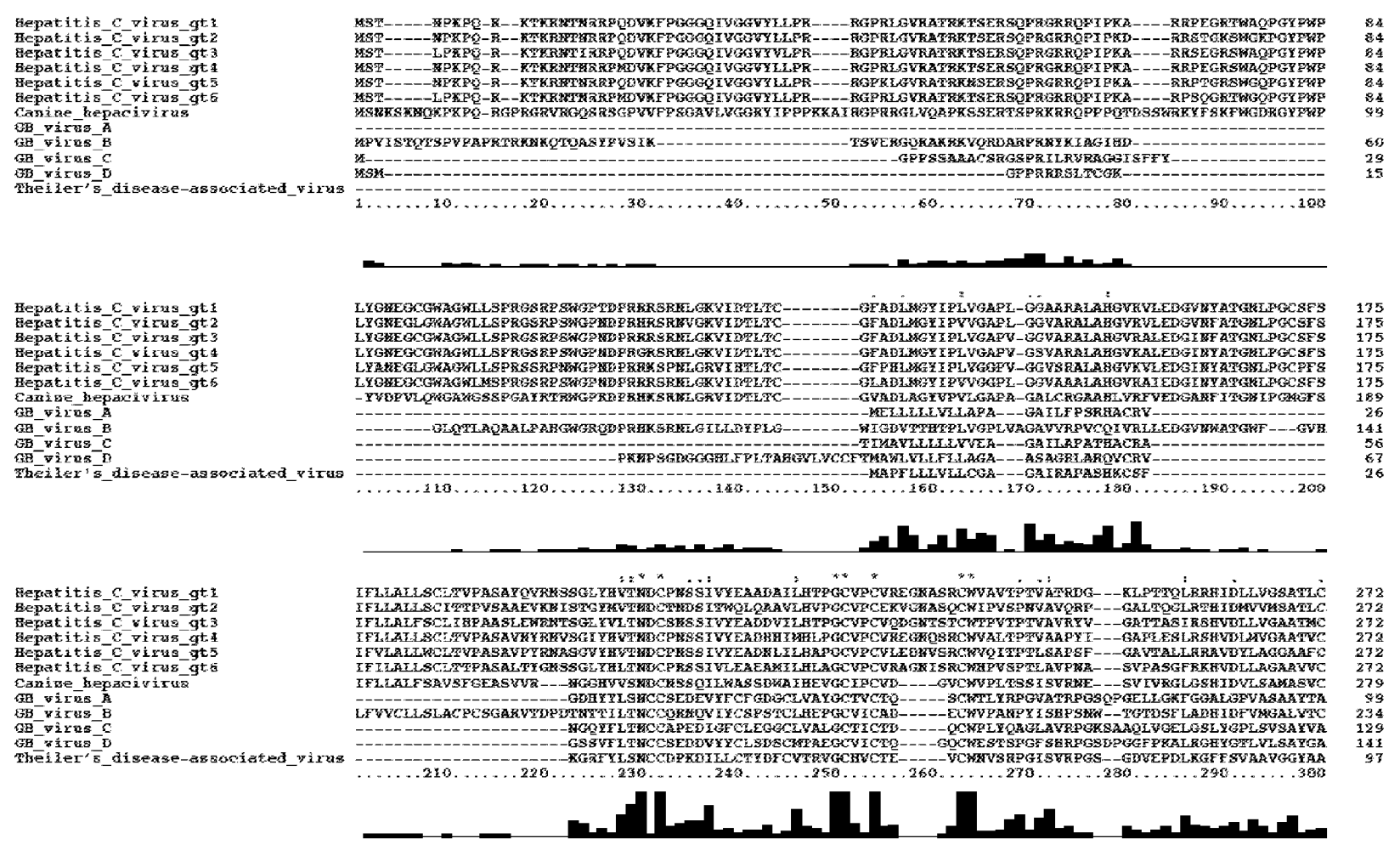
Figure 4B:
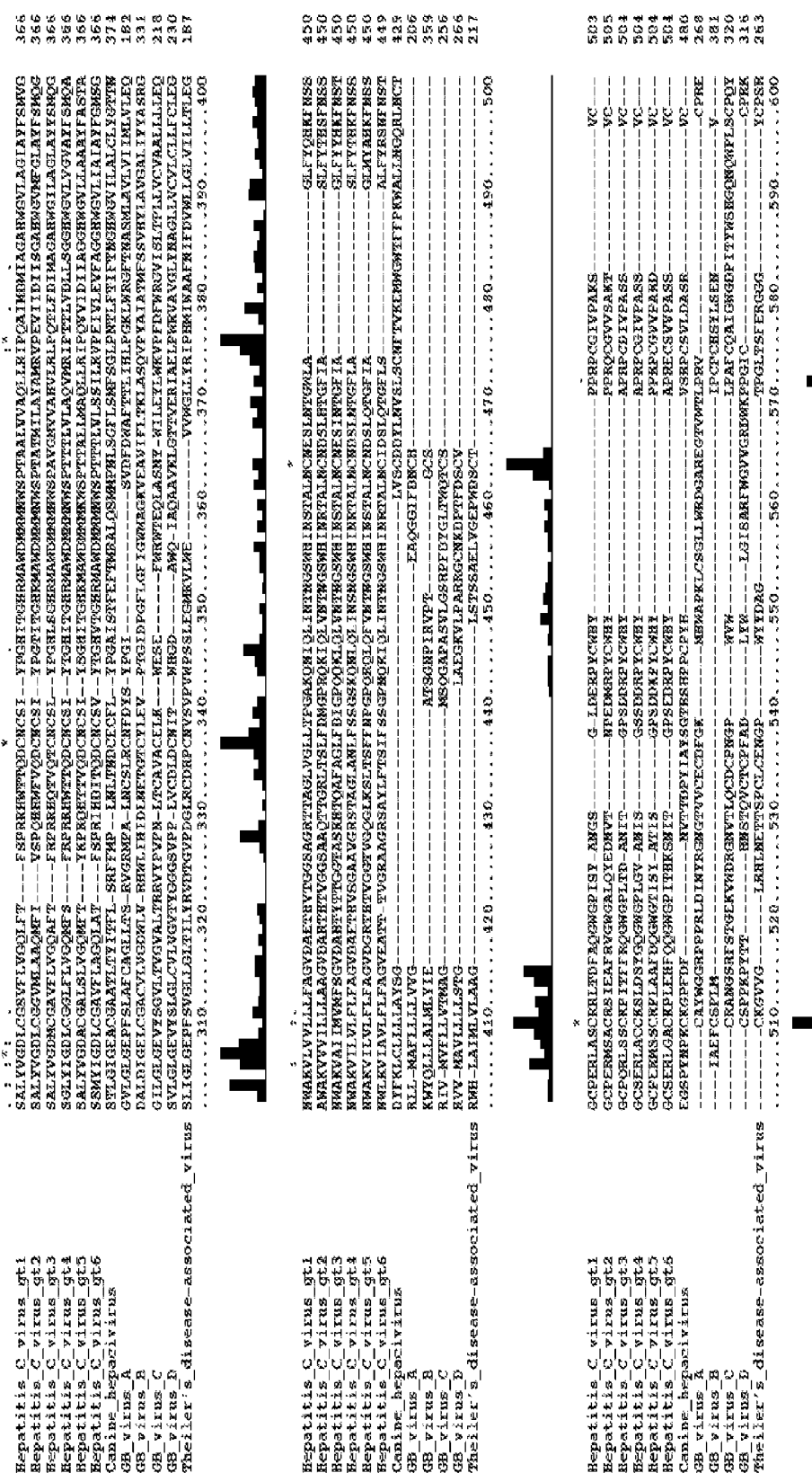
FIGS. 4A-N. Multiple sequence alignment of polyprotein sequences from Hepatitis C virus, GB viruses, Canine hepacivirus, and TDAV. All six HCV genotypes, all four GB viruses, Canine hepacivirus, and TDAV were aligned using MUSCLE and viewed in ClustalX v2.0. '*' above column indicates perfect conservation, '.' indicates high degree of conservation, and ':' indicates amino acid similarity across entire column. Bar graph below alignment shows fraction of column members matching consensus.
Figure 4C:
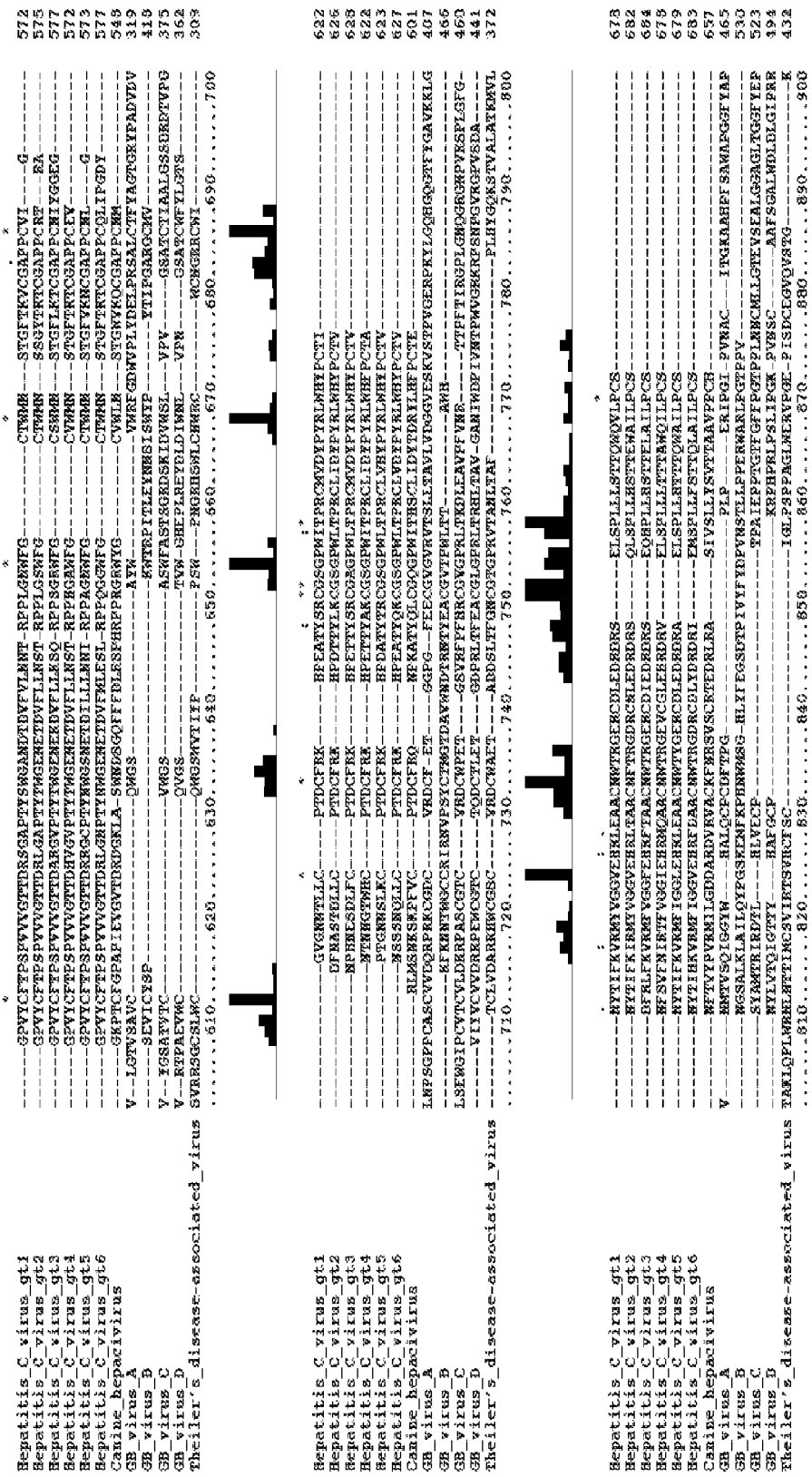
Figure 4D:
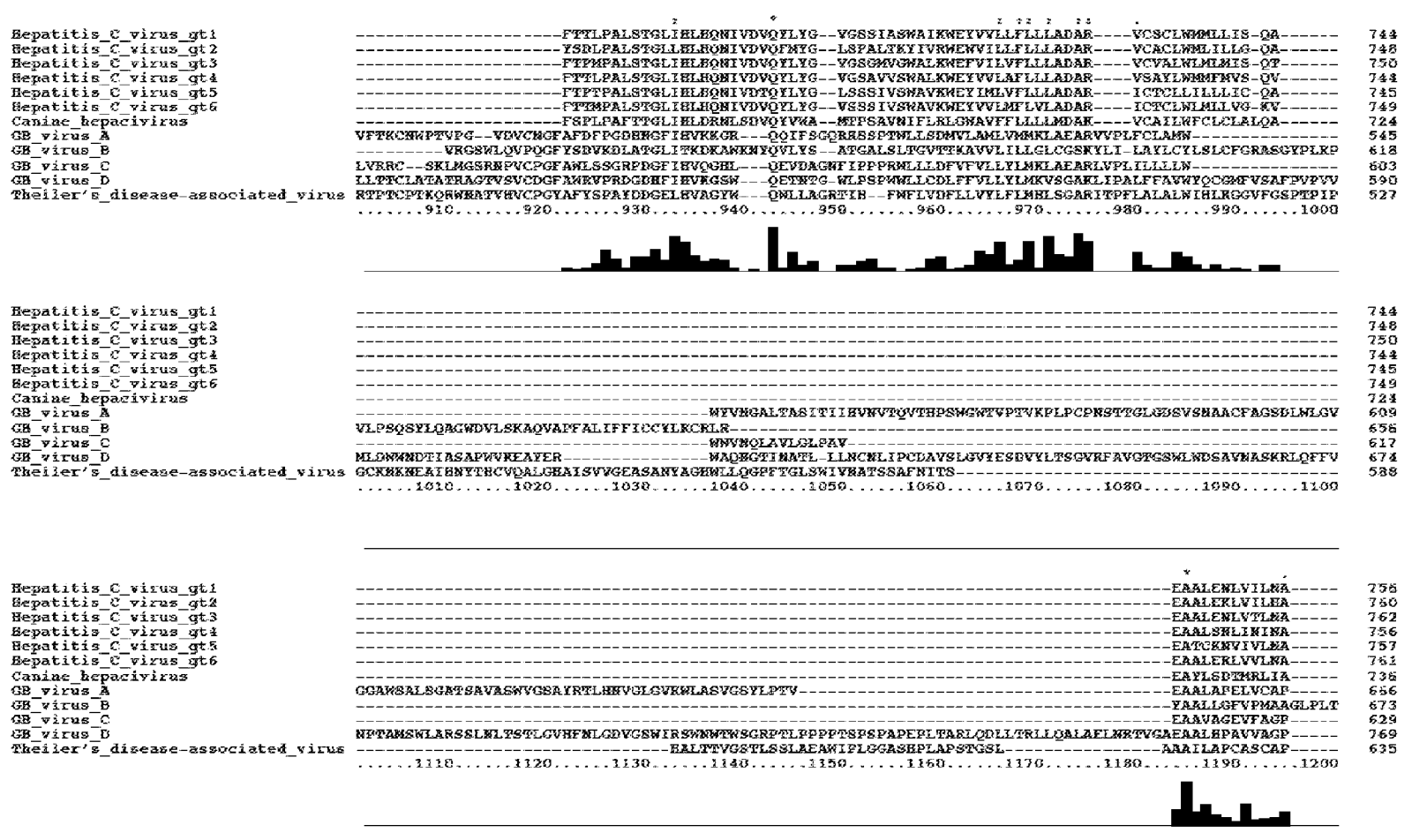
Figure 4E:
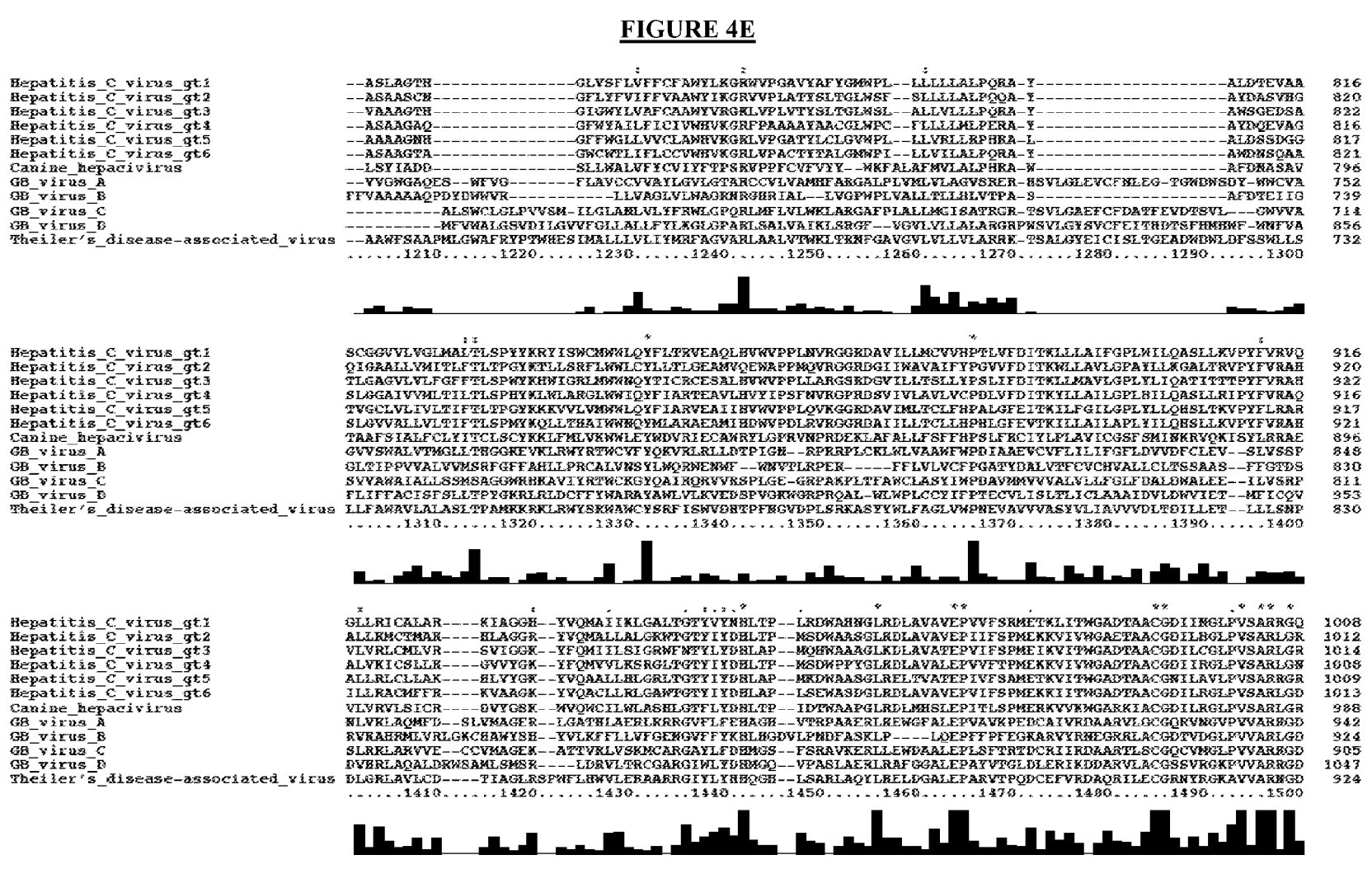
Figure 4F:
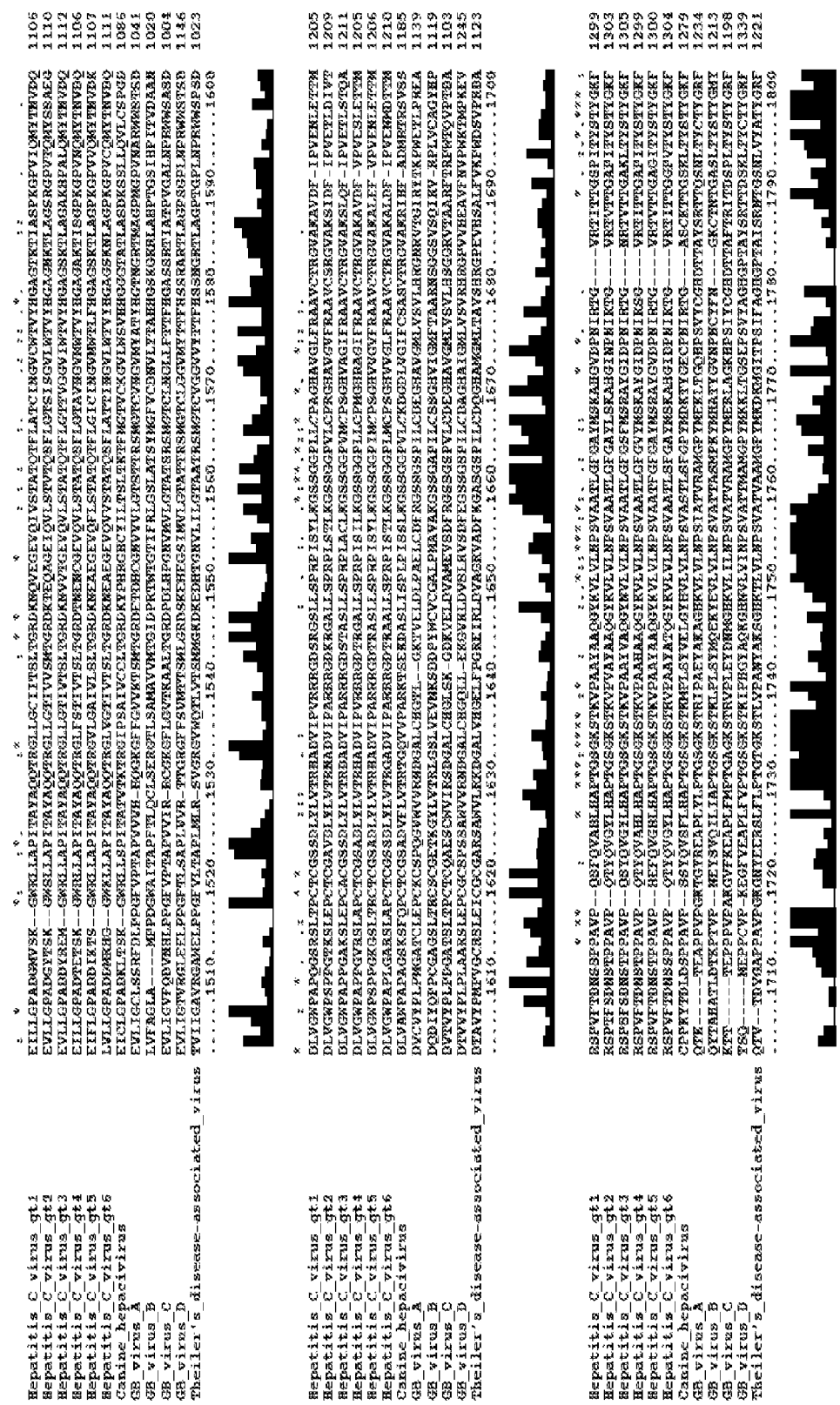
Figure 4G:
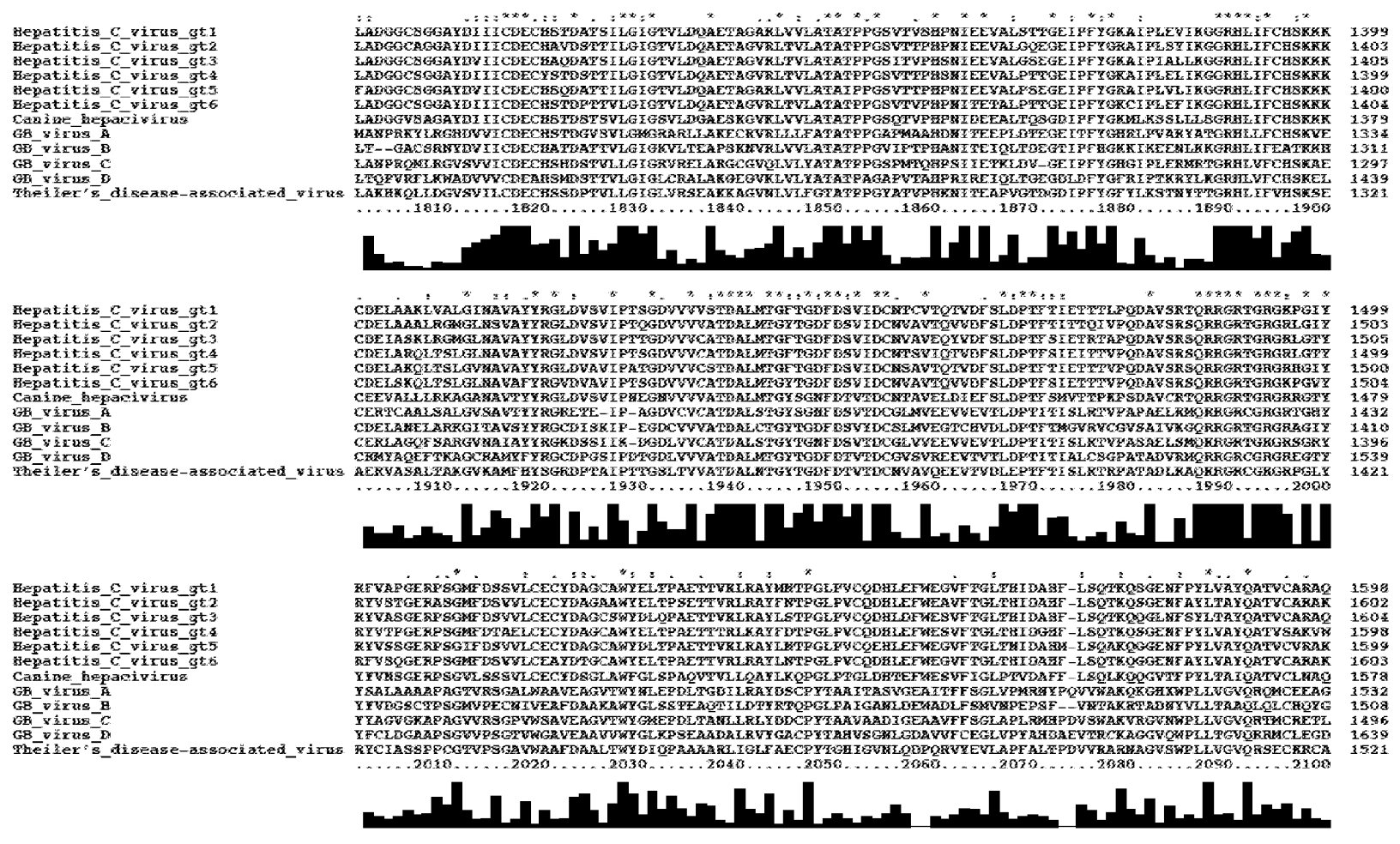
Figure 4H:
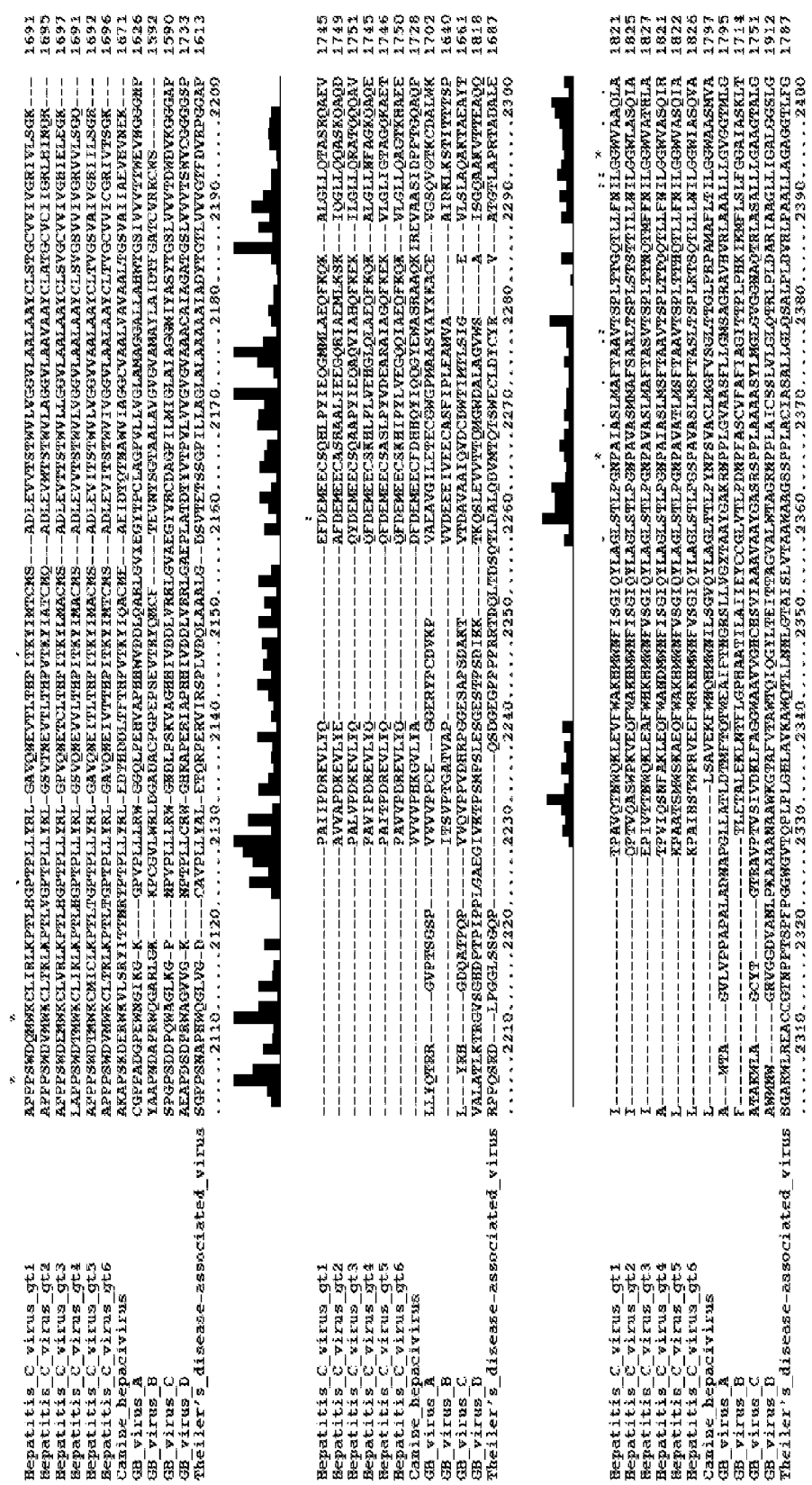
Figure 4I:
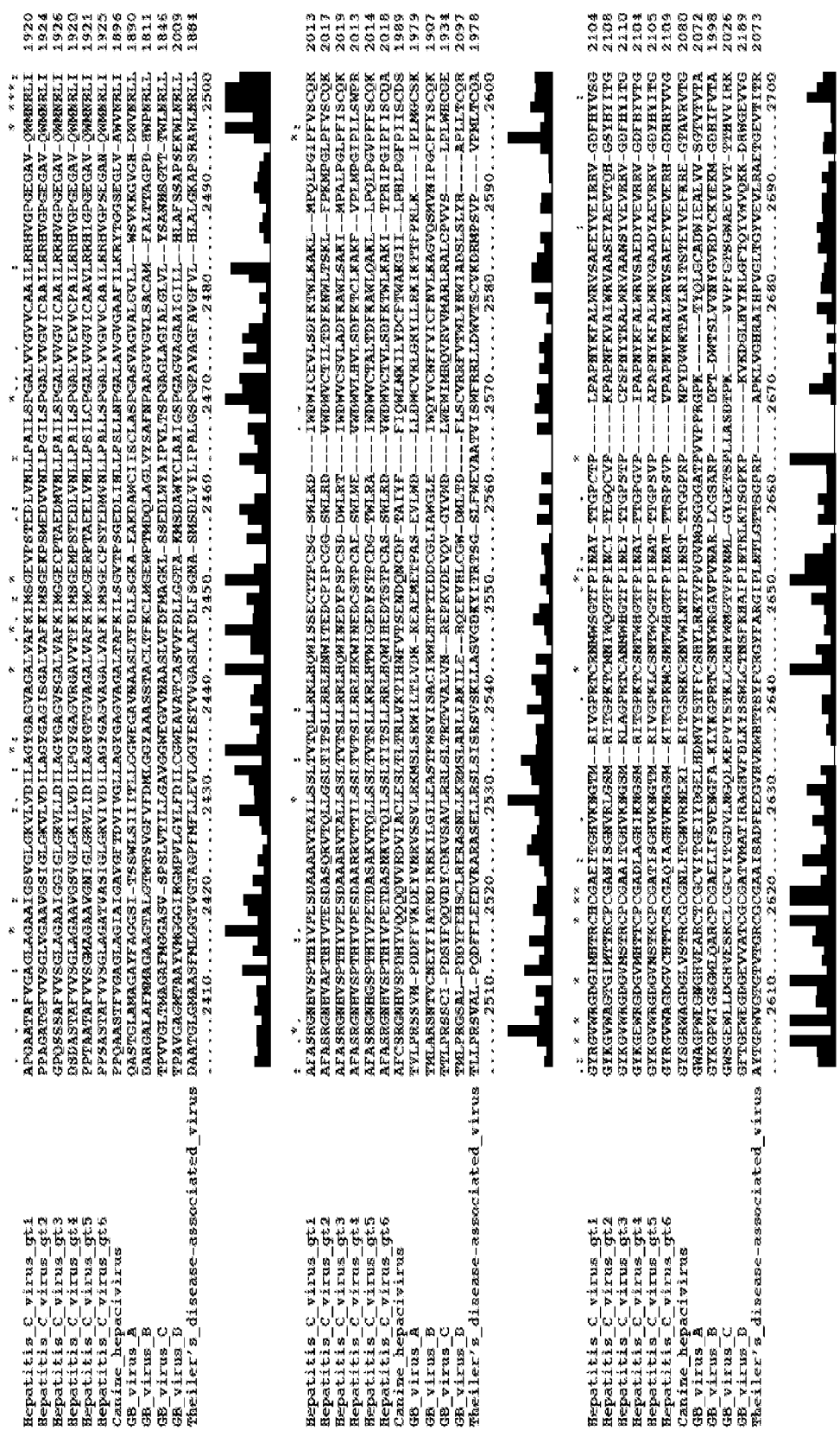
Figure 4J:
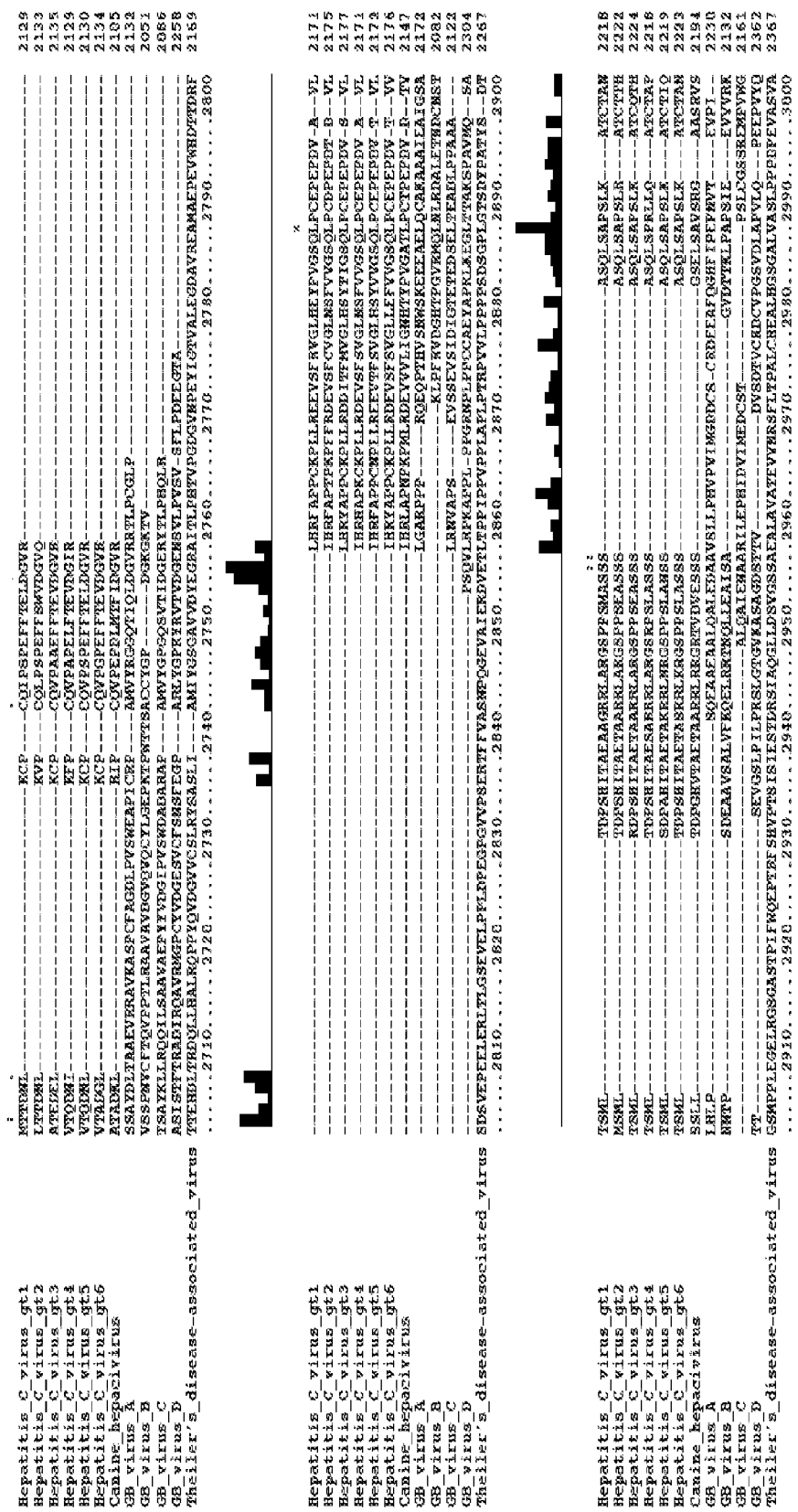
Figure 4K:
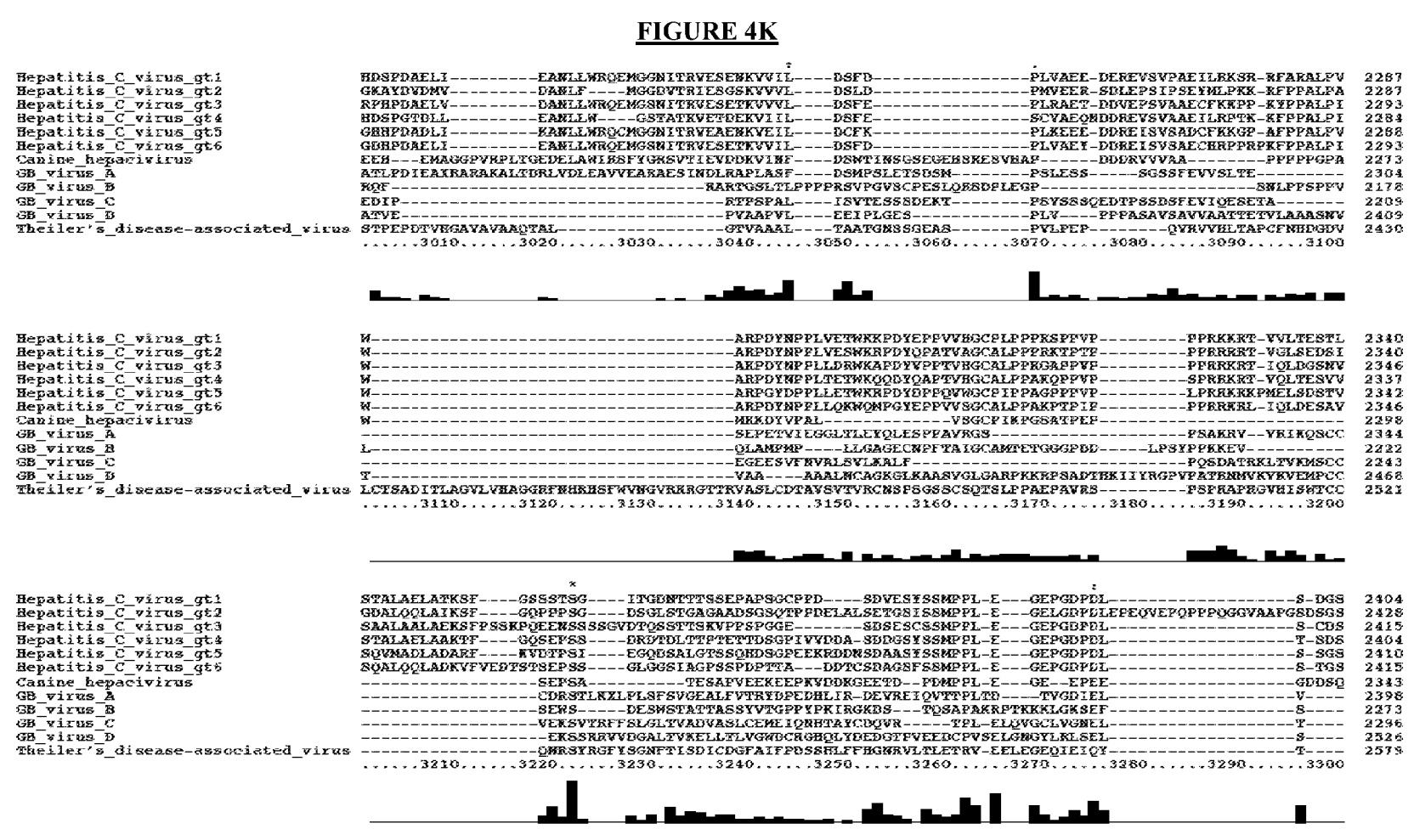
Figure 4L:
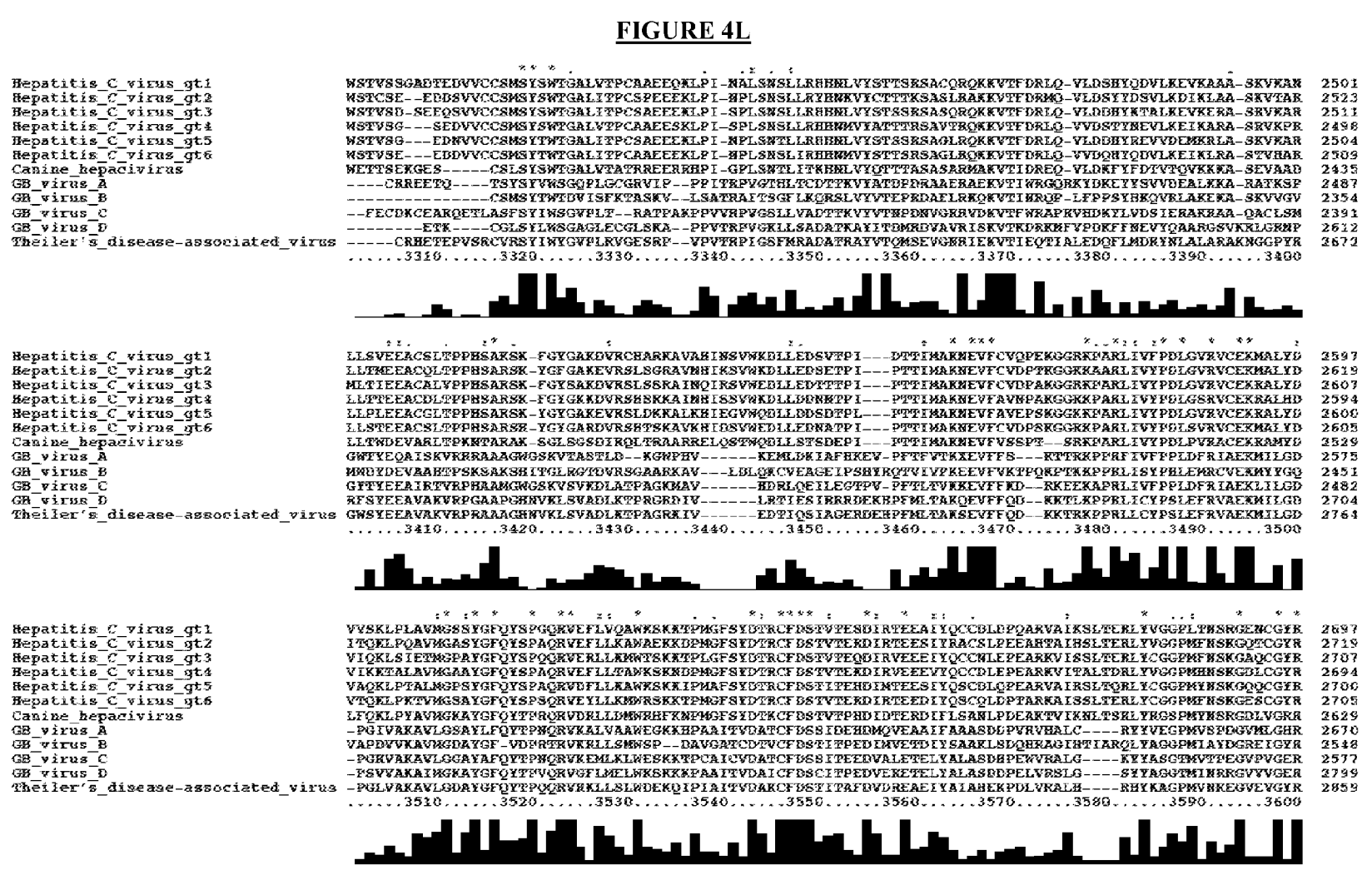
Figure 4M:
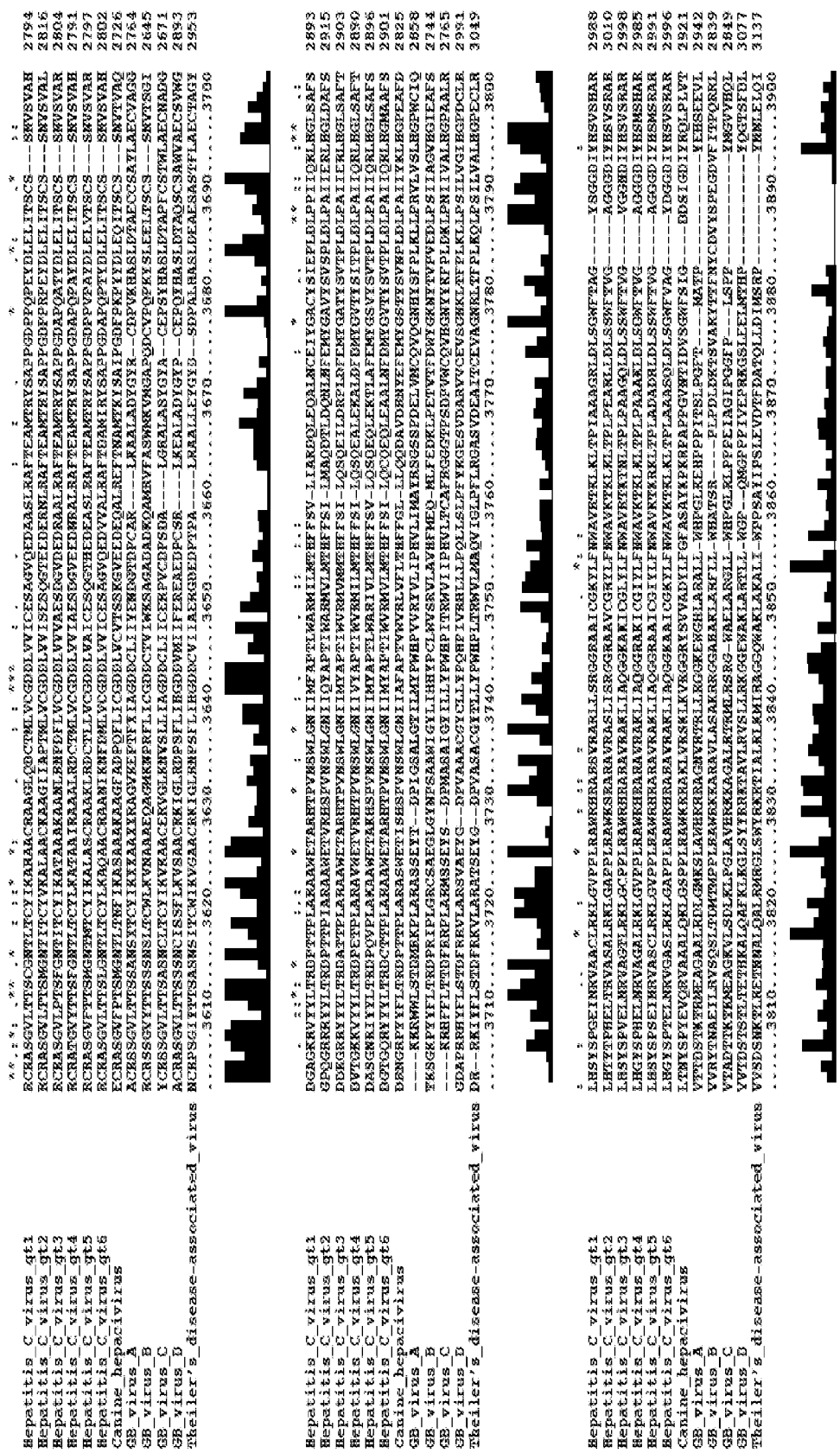
Figure 4N:

All RefSeq Flaviviridae polyprotein sequences, in addition to the polyprotein sequences from the recently-discovered non-primate hepaciviruses (NPHVs) (FIGS. 4A-N; Table 2), were aligned with the TDAV polyprotein sequence using MUSCLE. The multiple sequence alignment was imported into MEGA5, and a Neighbor-Joining phylogenetic tree was constructed with 100 bootstrap replications and viewed as a radiation tree (FIG. 3).

7. Physical Recovery and Validation of TDAV Sequence

The TDAV genome assembly was validated by recovering and sequencing ten overlapping RT-PCR amplicons that span positions 57-10127 (see below). Successful recovery of each amplicon required optimization of the RT and PCR conditions. Two different reverse transcription (RT) approaches were used in combination with 4 different PCR conditions to recover the 10 overlapping TDAV clones shown in FIG. 2D. Amplicons for each primer pair were cloned into the TOPO T/A pCR4.0 vector (Life Technologies) and the forward and reverse strands of at least three independent clones were sequenced (Elim Biopharma). A summary of the TDAV coordinates for each of the 10 amplicons, their corresponding reverse transcription conditions, PCR conditions, and PCR primer pairs that yielded specific products is described below. For reverse transcription, SuperScript III First-Strand Synthesis System (Life Technologies) was used according to manufacturer's protocol for random hexamers (RT condition 1) or gene-specific primers (RT condition 2) with a pool of the following primers: EVT-151, -155, -157, -163, -171, -175, -177, -183, -187, and -189 (Table 3). For PCR conditions 1-3, a standard Klentaq LA polymerase PCR reaction mix (cDNA template, 200 nM PCR primers, 200 μM dNTP, 0.1 U/μl Klentaq LA DNA polymerase (Sigma-Aldrich) in 1× Klentaq buffer) was

TABLE 2

GIs of Flaviviridae sequences referenced

| Virus name | GI | Label | Virus name | GI | Label |
|---|---|---|---|---|---|
| Aedes flavivirus | 254688377 | 37 | Kamiti River virus | 33620714 | 38 |
| Alkhurma virus | 24432114 | 30 | Karshi virus | 62326810 | 28 |
| Apoi virus | 20178607 | 27 | Kedougou virus | 226377836 | 13 |
| Bagaza virus | 226377838 | 7 | Kokobera virus | 126010839 | 11 |
| Border disease virus | 20198946 | 41 | Langat virus | 20260782 | 31 |
| Bovine viral diarrhea virus 1 | 9626650 | 45 | Louping ill virus | 9629457 | 33 |
| Bovine viral diarrhea virus 2 | 9629507 | 46 | Modoc virus | 20177456 | 26 |
| Bovine viral diarrhea virus 3 | 240114605 | 44 | Montana myotis leukoencephalitis virus | 22550316 | 24 |
| Bussuquara virus | 126010843 | 10 | Murray Valley encephalitis virus | 9633623 | 2 |
| Canine hepacivirus | 330722930 | 64 | NPHV #1 (AFJ20709.1) | 386686662 | 60 |
| Cell fusing agent virus | 9627243 | 39 | NPHV #2 (AFJ20708.1) | 386686660 | 61 |
| Classical swine fever virus | 12657942 | 42 | NPHV #3 (AFJ20707.1) | 386686657 | 58 |
| Culex flavivirus | 166159178 | 35 | NPHV #4 (AFJ20706.1) | 386686655 | 62 |
| Dengue virus 1 | 9626686 | 17 | NPHV #5 (AFJ20705.1) | 386686653 | 63 |
| Dengue virus 2 | 159024209 | 15 | NPHV #6 (AFJ20704.1) | 386686651 | 59 |
| Dengue virus 3 | 163644369 | 16 | NPHV #7 (AFJ20703.1) | 386686649 | 65 |
| Dengue virus 4 | 12084823 | 14 | Omsk hemorrhagic fever virus | 33589254 | 32 |
| Donggang virus | 380877199 | 18 | Pestivirus giraffe 1 | 20178633 | 43 |
| Duck flavivirus TA | 379764914 | 9 | Powassan virus | 20260780 | 29 |
| Entebbe bat virus | 119952255 | 20 | Quang Binh virus | 229904920 | 36 |
| Theiler's disease-associated virus | [TBD] | 47 | Rio Bravo virus | 20178609 | 25 |
| GB virus A | 9629719 | 49 | Sepik virus | 119952253 | 23 |
| GB virus B | 9628102 | 51 | St Louis encephalitis virus | 123205972 | 5 |
| GB virus C | 9628706 | 50 | Tamana bat virus | 21397175 | 40 |
| GB virus D | 300431402 | 48 | Tembusu virus | 340034687 | 8 |
| Hepatitis C virus gt1 | 22129793 | 53 | Tick-borne encephalitis virus | 9628432 | 34 |
| Hepatitis C virus gt2 | 157781213 | 57 | Usutu virus | 56692442 | 1 |
| Hepatitis C virus gt3 | 157781217 | 56 | Wesselsbron virus | 238801615 | 22 |
| Hepatitis C virus gt4 | 157781209 | 54 | West Nile virus | 158516888 | 4 |
| Hepatitis C virus gt5 | 157781211 | 55 | Yellow fever virus | 9627245 | 21 |
| Hepatitis C virus gt6 | 157781215 | 52 | Yokose virus | 33112011 | 19 |
| Ilheus virus | 126010841 | 6 | Zika virus | 226377834 | 12 |
| Japanese encephalitis virus | 9626461 | 3 | | | | cycled under the following 3 different conditions: (1) 94° C. for 60 s, 32 cycles of 94° C. for 30 s, 55° C. for 30 s, 68° C. for 1 min 45 s, followed by 68° C. for 7 min; (2) 94° C. for 60 s, 32 cycles of 94° C. for 30 s, 59.5° C. for 30 s, 68° C. for 1 min 45 s, followed by 68° C. for 7 min; or (3) 94° C. for 60 s, then 1 cycle of 94° C. for 30 s, 65° C. for 30 s, and 68° C. for 1 min 45 s, followed by 9 additional cycles with a 1° C. decrease in annealing temperature, then 25 cycles of 94° C. for 30 s, 55° C. for 30 s, 68° C. for 1 min 45 s, then 68° C. for 7 min. For PCR condition 4, a modified Phusion DNA polymerase PCR reaction mix (cDNA template, 500 nM PCR primers, 200 uM dNTP and 0.1 U/ul Phusion DNA polymerase (New England Biolabs) in 1× Phusion HF buffer supplemented with 3% DMSO) was cycled under the following conditions: 94° C. for 60 s, then 1 cycle of 94° C. for 30 s, 65° C. for 30 s, and 68° C. for 1 min 45 s, followed by 9 additional cycles with a 1° C. decrease in annealing temperature, then 25 cycles of 94° C. for 30 s, 55° C. for 30 s, 68° C. for 1 min 45 s, followed by 68° C. for 7 min (Table 4). Ultimately, one of two RT conditions and one of four PCR conditions produced a specific amplicon for each primer pair that was TOPO-cloned according to the manufacturer's protocol (Life Technologies, San Diego, Calif.). At least three independent TOPO cloned inserts were sequenced by Elim Biopharma (Hayward, Calif.).

TABLE 3

Oligonucleotides Used

| Primer | SEQ ID NO.: | Sequence (5'-3') | Use* | Source† | Primer Target | Primer Coordinates |
|---|---|---|---|---|---|---|
| EVT-144 | 36 | CGTAAGGGCGCGTAGTGG | 1 | a | TDAV | 57-74 |
| EVT-145 | 37 | CCGAAGCATCAAGGAACC | 4 | a | TDAV | 494-477 |
| EVT-146 | 4 | AGGGTTCTTCGGGTAAATCC | 2, 3 | a | TDAV | 171-190 |
| EVT-147 | 5 | CCCTCGGACTGAATTATAGGC | 2, 3, 4 | a | TDAV | 336-316 |
| EVT-151 | 38 | ACACATTGCAAGGTCTGTCG | 1 | a | TDAV | 1023-1004 |
| EVT-152 | 39 | GGCAGCCTTTAACATCTTCG | 1 | a | TDAV | 1115-1134 |
| EVT-153 | 40 | AACACCGCCAATTACAGAGC | 1 | a | TDAV | 1518-1499 |
| EVT-154 | 6 | GCTTTCCCTTTGCACTATGG | 2 | a | TDAV | 1674-1693 |
| EVT-155 | 7 | CAAGCCGATGCAACTAAAGC | 2 | a | TDAV | 1829-1810 |
| EVT-157 | 41 | AACCGAGAGTAGCACCAAGC | 1 | a | TDAV | 2917-2898 |
| EVT-158 | 8 | GGCTCTTTGGATTCACTTGC | 1, 2 | a | TDAV | 2144-2163 |
| EVT-159 | 9 | CCAGTGACCAGCATAATTCG | 1, 2 | a | TDAV | 2309-2290 |
| EVT-160 | 42 | CAAATCCTGATCTGGGAAGG | 1 | a | TDAV | 3100-3119 |
| EVT-161 | 43 | CCCAAGGATAAGGACATTGC | 1 | a | TDAV | 3557-3538 |
| EVT-162 | 10 | ATGCCATGGGTATGTTGACC | 2, 3 | a | TDAV | 3892-3911 |
| EVT-163 | 11 | CTCCTCGTAGTTGCCTTTGC | 1, 2, 3 | a | TDAV | 4046-4027 |
| EVT-164 | 44 | TTTGTGATGAGTGCCACAGC | 1 | a | TDAV | 4324-4343 |
| EVT-165 | 45 | GCGAAGAGAAATGGTGAAGG | 1 | a | TDAV | 4808-4789 |
| EVT-166 | 46 | GTTCTGAACCCGTCTGTTGC | 1 | a | TDAV | 4128-4147 |
| EVT-167 | 47 | CAGCAACTGCTTATGCTTGG | 1 | a | TDAV | 4304-4285 |
| EVT-169 | 48 | ACCCAAGTTGTTGAGCAAGG | 1 | a | TDAV | 5822-5803 |
| EVT-170 | 12 | TGGGAGTGTCTGGATTATTGC | 1, 2 | a | TDAV | 5607-5627 |
| EVT-171 | 13 | CAAGGTGTCCGAGAGGTAGG | 2 | a | TDAV | 5784-5765 |
| EVT-172 | 49 | TACACTGGACCTTGGGTTGG | 1 | a | TDAV | 6555-6574 |
| EVT-173 | 50 | CACCAGAACCGTAAATCATGG | 1 | a | TDAV | 6966-6946 |
| EVT-174 | 14 | TGGTACTGGTACCGTCACTGG | 2 | a | TDAV | 6572-6592 |
| EVT-175 | 15 | GCGAGGACCTGAAGTAGTGC | 2 | a | TDAV | 6734-6715 |
| EVT-177 | 51 | GAGCAGTCAAGTGCACAACC | 1 | a | TDAV | 7881-7862 |

TABLE 3-continued

Oligonucleotides Used

| Primer | SEQ ID NO.: | Sequence (5'-3') | Use* | Source† | Primer Target | Primer Coordinates |
|---|---|---|---|---|---|---|
| EVT-178 | 16 | CTCCTGTGCTCCCTGAACC | 1, 2 | a | TDAV | 7834-7852 |
| EVT-179 | 17 | AACACCATTGACCCAGAAGC | 1, 2 | a | TDAV | 8000-7981 |
| EVT-180 | 52 | TTGCCATCTTTCCAGACTCC | 1 | a | TDAV | 8245-8264 |
| EVT-181 | 53 | ATAAGACCAGCCCCGATACG | 1 | a | TDAV | 8645-8626 |
| EVT-183 | 54 | GTCAACCGTGATAGCAATGG | 1 | a | TDAV | 9035-9016 |
| EVT-186 | 18 | CTTCTGCCTACATCCCATCG | 2 | a | TDAV | 9931-9950 |
| EVT-187 | 19 | TGCATACCTTTCGGCTAAGG | 2 | a | TDAV | 10127-10108 |
| EVT-189 | 55 | ACTCCCCCTGTTAACCTTGC | 1 | a | TDAV | 10409-10390 |
| EVT-192 | 20 | ATGCGGCGGCGTTATTCC | 2, 3 | b | equine 18S rRNA (AJ311673) | 1079-1096 |
| EVT-193 | 21 | GCTATCAATCTGTCAATCCTGTCC | 2, 3 | b | equine 18S rRNA (AJ311673) | 1282-1259 |
| EVT-194 | 22 | CGGGTAAACGGCGGGAGTAAC | 2 | b | equine 28S rRNA (EU554425) | 4-24 |
| EVT-195 | 23 | TAGGTAGGGACAGTGGGAATCTCG | 2 | b | equine 28S rRNA (EU554425) | 112-89 |
| EVT-196 | 24 | CACCACACCTTCTACAAC | 2 | b | equine b-actin (AF035774) | 259-276 |
| EVT-197 | 25 | ATCTGGGTCATCTTCTCG | 2 | b | equine b-actin (AF035774) | 365-348 |
| EVT-200 | 26 | GCCATCACCATCTTCCAG | 2 | b | equine GAPDH (AF157626) | 85-103 |
| EVT-201 | 27 | GACTCCACAACATATTCAGC | 2 | b | equine GAPDH (AF157626) | 162-143 |
| 3Sol_N | 56 | GCTCTTCCGATCTNNNNNN | 5 | c | Illumina library adapters | n.a. |
| 3_Sol | 57 | GCTCTTCCGATCT | 5 | c | Illumina library adapters | n.a. |
| SolM1 | 58 | AATGATACGGCGACCACCGAGATCTACACTCTTTCCCTACACGACGCTCTTCCGATCT | 5 | c | Illumina library adapters | n.a. |
| SolM2 | 59 | CAAGCAGAAGACGGCATACGAGATNNNNNNNGTGACTGGAGTTCAGACGTGTGCTCTTCCGATCT‡ | 5 | c | Illumina library adapters | n.a. |
| 5SolM1_18** | 60 | AATGATACGGCGACCACC | 5 | c | Illumina library adapters | n.a. |
| 5SolM2_19** | 61 | CAAGCAGAAGACGGCATAC | 5 | c | Illumina library adapters | n.a. |
| 1.1 | 62 | AATGATACGGCGACCACCGAGAT | 6 | a | Illumina library adapters | n.a. |
| 2.1 | 63 | CAAGCAGAAGACGGCATACGA | 6 | a | Illumina library adapters | n.a. |

*Use 1 = physical recovery of TDAV amplicons for genome sequence validation, Use 2 = TDAV qRT-PCR assay development, Use 3 = qRT-PCR assay used in the study, Use 4 = TDAV 5' RACE, Use 5 = Illumina sequencing library preparation, Use 6 = quantitative PCR assay for Illumina sequencing library preparations.
†Source a = This study, Source b = Zhang YW, Davis EG and Bai J, 2009. Determination of internal control for gene expression studies in equine tissue and cell culture using quantitative RT-PCR. Veterinary Immunology and Immunopathology 130, 114-119; Source c = Runckel C, Flenniken, ML, Engel JC, Ruby JG, Ganem D, Andino R, and DeRisi JL, 2011. Temporal analysis of the honey bee microbiome reveals four novel viruses and seasonal prevalence of known viruses, Nosema and Crithidia. PLoS One. 6(6): e20656. Epub 2011 Jun 7.
‡The X in the sequence indicates base positions of barcode sequences in Illumina library adapters used in this study.
**DNA oligo manufactured with the CleanAmp Precision ™ modification (TriLink BioTechnologies, San Diego, CA).

TABLE 4

RT-PCR conditions for physical recovery of TDAV sequence

| TDAV Amplicon Coordinates | RT Condition* | PCR Condition* | PCR primers† |
|---|---|---|---|
| 1-336 | 5'RACE (see below) | 5'RACE (see below) | 5'RACE adapter, EVT147 |
| 57-1518 | 2 | 1 | EVT-144, -153 |
| 1115-2309 | 1 | 1 | EVT-152, -159 |
| 2144-3557 | 2 | 1 | EVT-158, -161 |
| 3100-4304 | 1 | 1 | EVT-160, -167 |
| 4128-4808 | 2 | 4 | EVT-166, -165 |
| 4324-5822 | 2 | 3 | EVT-164, -169 |
| 5607-6966 | 1 | 2 | EVT-170, -173 |

TABLE 4-continued

RT-PCR conditions for physical recovery of TDAV sequence

| TDAV Amplicon Coordinates | RT Condition* | PCR Condition* | PCR primers† |
|---|---|---|---|
| 6555-8000 | 1 | 2 | EVT-172, -179 |
| 7834-8645 | 2 | 2 | EVT-178, -181 |
| 8245-10127 | 1 | 2 | EVT-180, -187 |

*See Materials and Methods for detailed description of conditions listed.

†See Table 3 for PCR primer sequences.

The 5'-most sequence of TDAV was recovered by performing 5' Rapid Amplification of cDNA Ends (5'-RACE) according to the manufacturer's protocol (Life Technologies. Briefly, 2 μl of RNA from two subjects (Horse A1 and Horse A2) and Antitoxin 2 were used as input to the initial RT step. Reverse transcription was primed by EVT-145 (Table 3). Purified cDNAs were subjected to a tailing reaction with dCTP. dCTP-tailed cDNA was used as a template for PCR with EVT-147 (Table 3) and the manufacturer-supplied Abridged Anchor Primer. PCR was performed according to the Taq polymerase manufacturer's protocol (New England BioLabs) with the following cycling conditions: 94° C. for 2 min, then 32 cycles of 94° C. for 30 s, 55° C. for 30 s, 72° C. for 1 min, followed by 72° C. for 7 min. PCR products were purified and concentrated by column purification (DNA Clean & Concentrator™-5, Zymo Research) according to the manufacturer's protocol. Purified 5' RACE products were size selected (292-438 bp) using the LabChip XT (DNA 750 assay kit, Caliper/Perkin Elmer).

8. PCR-Based TDAV Diagnostic Assay

The TDAV qRT-PCR diagnostic assay used RNA isolated from 300 μL equine serum or plasma, as described above. Two microliters of RNA were used for random-primed reverse transcription performed according to the manufacturer's protocol (SuperScript III First-Strand Synthesis System, Life Technologies). Diluted cDNA (1:10) was added to qPCR reactions with Fast SYBR Green Master Mix (Life Technologies) and one of the following primer pairs: EVT-162/-163 (TDAV), EVT-146/147 (TDAV) and EVT-192/-193 (equine 18S rRNA). All samples were blinded and reactions were performed at least in triplicate. The qRT-PCR TDAV assay was designed to separate known positive and known negative samples by at least 9 $C_t$s in initial pilot experiments. Pre-defined $C_t$ threshold values for TDAV positivity could not be set because of small day-to-day variability in the assay; thus positivity was defined as i) detecting equine 18S rRNA with $C_t$s substantially lower than in blinded samples predicted to be $H_2O$ and ii) detecting viral RNA with both TDAV primer sets with $C_t$s substantially lower than in blinded samples predicted to be negative controls.

B. Results

1. Outbreak Summary

An outbreak of Theiler's disease that occurred on a horse farm in the western United States following prophylactic treatment of the animals for botulinum toxin poisoning was investigated. The farm (Farm A) housed a population of 75 horses, of which four were diagnosed with signs of botulism poisoning after consumption of contaminated feed. Two of the horses presented with a rapid onset of paralysis and were euthanized. The other two horses displayed milder symptoms, were treated with equine botulinum antitoxin plasma, and made a full recovery. As a prophylactic measure, botulinum antitoxin treatment was then administered to 21 other horses suspected of exposure to the contaminated feed. Because quantities of the initial antitoxin batch were limited, the first four horses were provided the same antitoxin used to treat the two symptomatic horses ('Antitoxin 1') and 17 horses were administered an independently sourced botulinum antitoxin ('Antitoxin 2'). The remaining horses on the farm went untreated. One of the horses that was treated with Antitoxin 1 upon presentation with mild symptoms of botulism was removed from the farm and was unavailable for further monitoring, leaving a total of 22 horses that were treated with Antitoxin 1 (N=5) or Antitoxin 2 (N=17) for continued observation and testing. Within eight weeks, two of the horses treated with Antitoxin 2 (Horse A1 and Horse A2) displayed signs of Theiler's disease, including lethargy, poor appetite, photodermatitis, and jaundice. Serum levels of liver enzymes were also markedly elevated in both horses. All horses that received antitoxin treatment were subsequently monitored for overt symptoms of hepatitis and weekly serum samples were tested for signs of liver injury (elevated levels of aspartate amino transferase (AST), gamma glutamyl transferase (GGT), sorbitol dehydrogenase (SDH), glutamate dehydrogenase (GLDH or GD), and bilirubin). In total, eight of the 22 horses that received antitoxin treatment developed hepatitis over the following several weeks (FIG. 1). All eight cases occurred in horses that had been treated with Antitoxin 2, raising the possibility that this preparation might harbor a causal chemical or infectious agent. To address the latter possibility, we extracted RNA and prepared sequencing libraries from serum specimens of the two index cases (Horse A1 and Horse A2), as well as from Antitoxin 2 itself.

2. Viral Sequence Detection Leads to Assembly of a Novel Flaviviridae Genome

Massively parallel sequencing of libraries from Horse A1, Horse A2, and Antitoxin 2 resulted in an average of 22 million 100 nucleotide (nt) sequence reads for each sample. For the two serum specimens, complexity and host filtering of the raw sequence data removed approximately 95% of the reads from downstream analyses. For the Antitoxin 2 sample, complexity and host filtering removed approximately 50% of the reads. The remaining reads were mapped to all viral protein sequences in RefSeq. For Horses A1 and A2 approximately 0.01% of sequence reads (2954 and 3522 reads, respectively) mapped to members of the Flaviviridae; 0.06% (9116) of Antitoxin 2 reads mapped to the same virus family. In addition to the abundance of Flaviviridae reads in each sample, Horse A1 had a single read pair mapping to Baculoviridae, a family of insect viruses, and another read pair derived from Adenoviridae, mapping to the region found in laboratory recombination vectors; Horse A2 contained 80 read pairs deriving from a 298 nt contiguous region in Pepper Mild Mottle virus, a plant virus from the Virgaviridae family. These reads likely represent artifactual contamination introduced during sample collection and library preparation. Horse A2 additionally contained four read pairs derived from Equid herpesvirus 2, a common virus associated with mild respiratory disease in horses. No additional viral reads were detected in the Antitoxin 2 specimen. Sequence reads mapping to members of the Flaviviridae were used as the starting point for de novo genome assemblies using the assembly algorithm PRICE. A 10.5 kilobase (kb) contig corresponding to a previously unknown and divergent genome of the Flaviviridae family was assembled from the Horse A1 sequences, and long contigs from an essentially identical (>99% nucleotide sequence identity) genome were assembled from the Horse A2 and Antitoxin 2 samples (FIG. 2A). Mapping the reads from each sample back to the assembled genome revealed that the true viral sequence coverage was two orders of magnitude greater than initially perceived: 0.8% of reads from Horse A1, 1.4% of reads from Horse A2, and 2.4% of reads from Antitoxin 2 mapped to the recovered genome (FIG. 2B). This novel genome (Theiler's disease-associated virus (TDAV)) is provided in SEQ ID NO.: 1, the amino acid coding sequence of SEQ ID NO.: 1 is presented as SEQ ID NO.: 2, and the amino acid sequence encoded by SEQ ID NO.: 1 and SEQ ID NO.: 2 is presented as SEQ ID NO.: 3.

3. Genome Features of Theiler's Disease-Associated Virus (TDAV)

Figure 8:
FIG. 8. Thirty-five high quality sequences from the RACE clones were analyzed to determine the true 5' end of the TDAV genome. Polyguanine (or polycytosine for clones in the reverse orientation) stretches generated during the 5' RACE procedure were identified preceding the putative 5' end of the genome and were removed. Positions 1-7 (labeled) were included in the assembly as the consensus sequence, TGATACC, while the position labeled '?' represents a potential polymorphic 'T' seen in five clones. Sequence logo was generated using WebLogo (http://weblogo.berkeley.edu).

In order to validate the computer-generated genome assembly, the presence of artificial structural rearrangements was first investigated. In an assembly free of artifacts, the computed amplicon sizes across the genome should match the amplicon size selected during library preparation. This was evaluated by calculating the distance between read pairs mapping back to the TDAV genome, and by plotting the median value of all calculated amplicon sizes at each position. The calculated amplicon sizes based on the Horse A1 data closely matched the experimentally-generated insert size of 300±30 nucleotides (nt) (FIG. 2C). To obtain empirical support for the presence of the predicted TDAV sequence in clinical samples, RT-PCR was performed. RNA prepared from Horse A1 serum was amplified with primers pairs predicted to yield ten overlapping amplicons encompassing nearly the complete TDAV genome assembly (FIG. 2D). All ten amplicons were successfully recovered. Cloning and Sanger sequencing of three independent clones for each amplicon revealed >99% nucleotide identity with the in silico-generated TDAV assembly. The extreme 5' and 3' ends of the TDAV genome assembly were underrepresented in the initial library (FIG. 2B). The 5' end was investigated by 5' RACE (rapid amplification of cDNA ends) using RNA samples from Horse A1, Horse A2 and Antitoxin 2. This method extended the initial sequence assembly by 24 nucleotides. The reported 5' terminal nucleotide ('T') was found in 21 of 35 clones, while nine clones contained a different terminal nucleotide in that position, and five clones contained a single additional upstream nucleotide ('T') (FIG. 8). The sequence of the 3' end was not extended beyond the sequencing read assembly.

Figure 2:
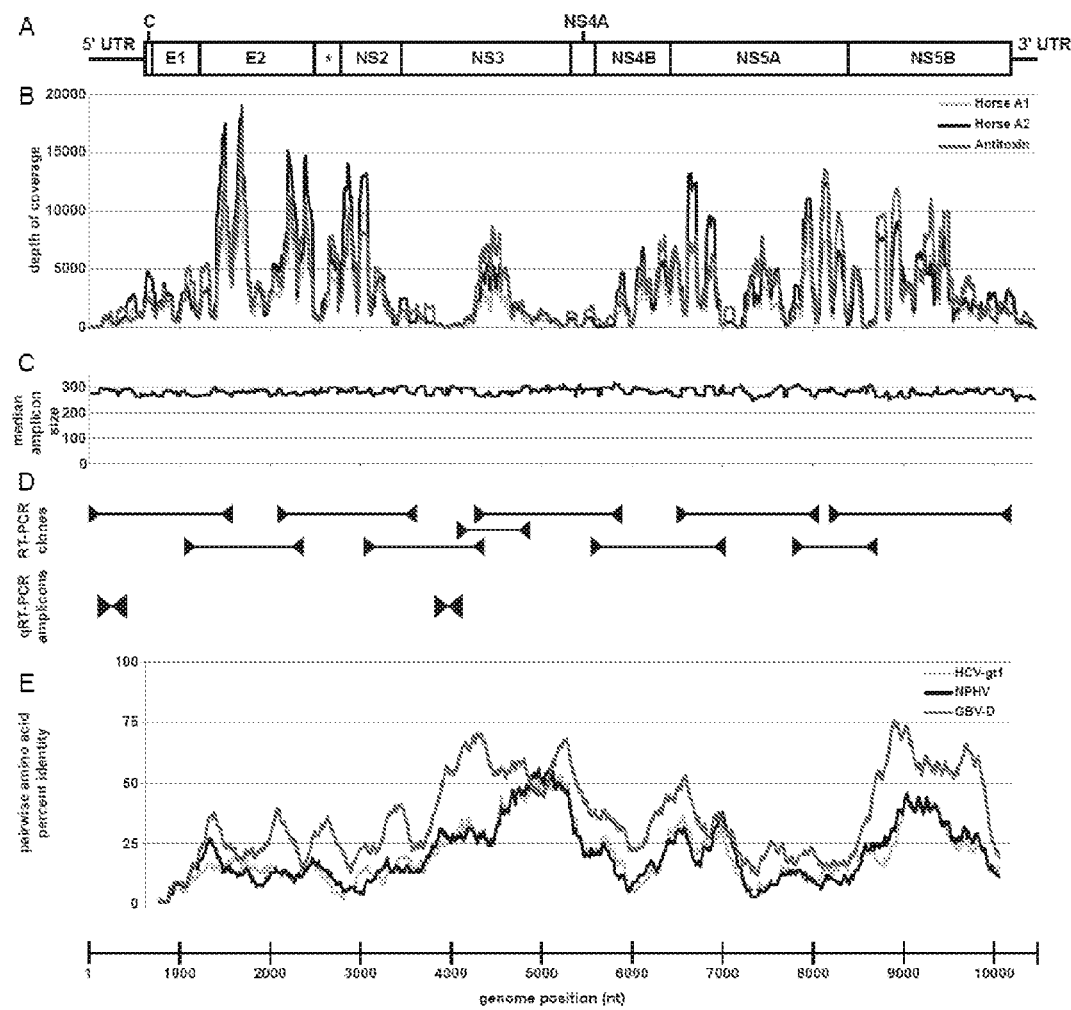
FIG. 2. Genome of Theiler's disease-associated virus (TDAV). (A) Schematic of the TDAV genome. Protein cleavage sites are putative and were annotated based on homologous inference from HCV (FIG. 4). (*) gene corresponding to HCV p7, GBV-B p13, GBV-D X, and GBV-A 21 kDa protein. (B) Coverage map of sequencing reads from Horse A1, Horse A2, and Antitoxin 2. (C) Median calculated amplicon size based on the distance between the 5' ends of paired end sequencing reads mapping to each nucleotide. (D) Overlapping clones recovered and sequenced to confirm the genome assembly (above) and the location of amplicons used in TDAV diagnosis and quantification (below). (E) Pairwise amino acid percent identity plot (100 aa windows) of TDAV compared to HCV-gt1, NPHV, and GBV-D. Genome position scale (bottom) refers to panels A-E.
Figure 9A:
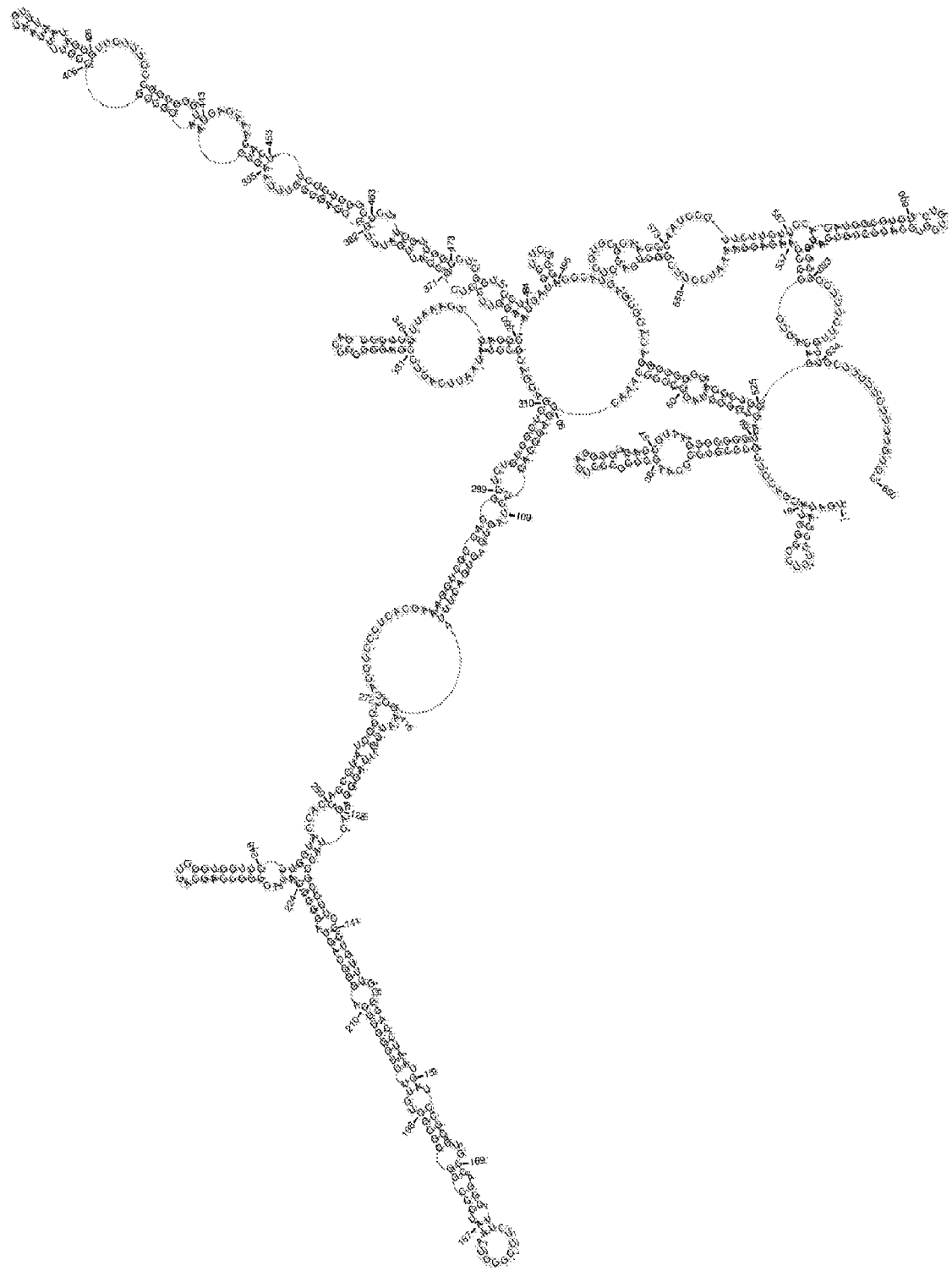
FIGS. 9A-B. Predicted structures for 5' UTR and 3' UTR. RNA secondary structure for (A) 5' UTR and (B) 3' UTR sequences was predicted using CONTRAfold and viewed using PseudoViewer3. Approximately 30 nucleotides downstream of the translation initiation codon ('AUG', bold in (A)) and 30 nucleotides upstream of translation stop codon ('UGA', bold in (B)) were folded in addition to the UTRs. Coordinates in (B) are relative and offset by 10,154 nt (position 1=nt 10155 in TDAV; position 325=nt 10479 in TDAV).
Figure 9B:
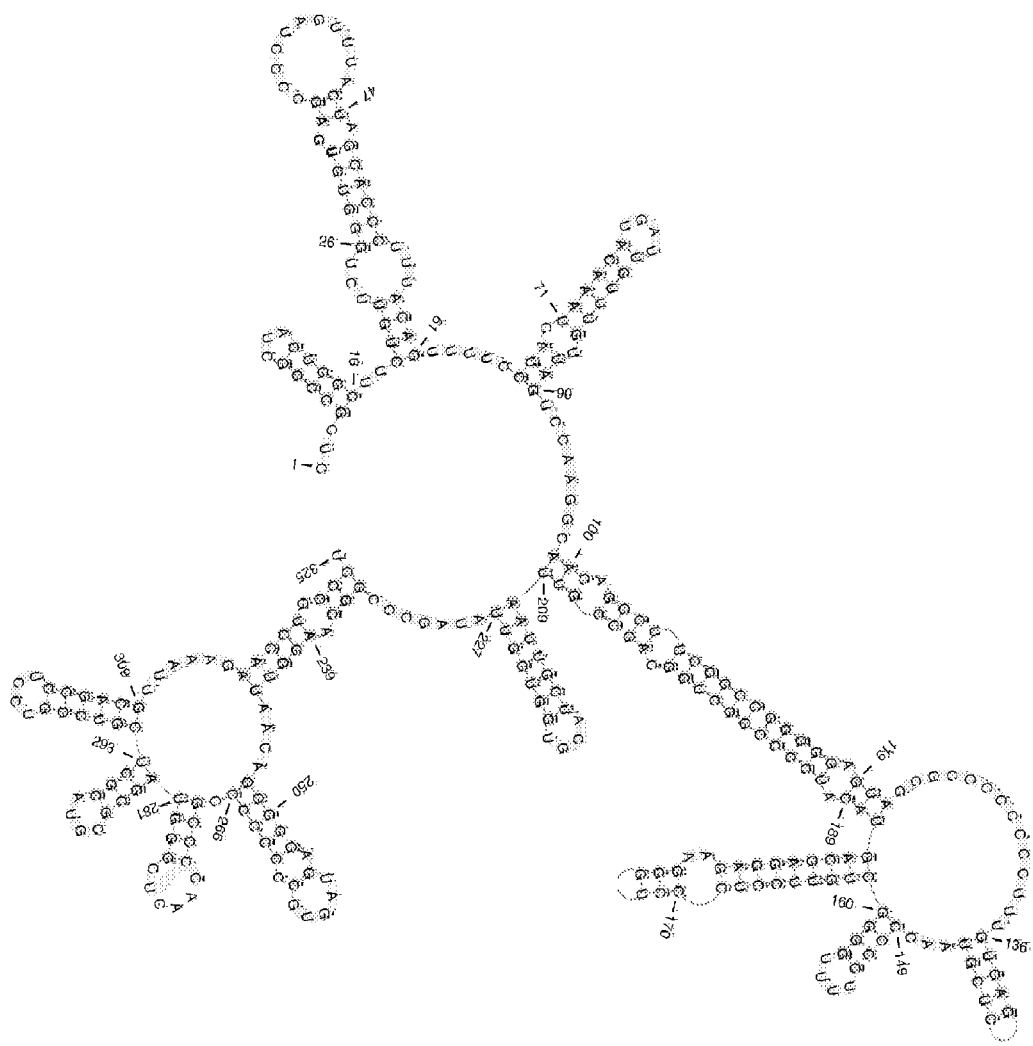

The TDAV genome assembly is approximately 10,479 nt in length, encompassing the 5' untranslated region (UTR), a single open reading frame (ORF) initiating from an AUG at position 618 and encoding a putative polyprotein 3189 amino acid (aa) residues in length, and 292 nt of the 3'UTR. By comparison to related Flaviviridae, the TDAV genome encodes three putative structural (core, E1, E2) and seven non-structural (a gene product of variable length mapping between E2 and NS2, NS2, NS3, NS4A, NS4B, NS5A, and NS5B) proteins (FIGS. 2 and 9).

Although TDAV appears most closely related to the GB viruses and hepaciviruses in the Flaviviridae phylogeny (FIGS. 3 and 4A-N), it is highly divergent from both groups. TDAV shares only 35.3% amino acid sequence identity over the length of the entire polyprotein with its nearest relative, GB virus D (GBV-D), 20.5% identity with hepatitis C virus (genotype 1; HCV-gt1), and 20.4% identity with the most closely related member of the Flaviviridae recently identified in horses, non-primate hepacivirus (NPHV). Pairwise sequence identity between TDAV and these species varies dramatically (FIG. 2E, FIGS. 4A-N). The putative serine protease, NS3, and the RNA-dependent RNA polymerase, NS5B, are the most conserved regions of the polyprotein, with some regions exceeding 75% amino acid identity to GBV-D (FIG. 2E). At 617 nt and 292 nt, the TDAV 5' UTR and (possibly partial) 3' UTR are longer than those found in the hepaciviruses (approximately 340 nt and 200-235 nt, respectively). Though there appears to be significant potential for secondary structure predicted in each UTR, canonical IRES or other RNA structural motifs typical of other Flaviviridae are not readily apparent (FIG. 9). The core protein, which serves as the nucleocapsid for HCV, is truncated or absent in GBV-A, GBV-C and GBV-D (15). In TDAV, its predicted size is also small (26 aa), with a putative signal peptidase cleavage site between amino acids 15 and 16. Likewise, the fourth predicted TDAV protein, which lies between E2 and NS2, appears more similar to GB viruses than hepaciviruses. In HCV, this region encodes p'7, a 7 kDa (63 aa) protein that is important for virus assembly and release. In GB viruses, the protein varies from 6 kDa (in GBV-C) to 21 kDa (in GBV-A), and its role in the virus life cycle is not clear. The corresponding TDAV protein has a predicted molecular weight of approximately 10.8 kDa. Finally, unlike the GB and hepaciviruses, the TDAV NS5A protein contains three putative insertions spanning approximately 160 aa not found in any related member of the Flaviviridae, including a large insertion of nearly 100 aa in domain 1b of NS5A, and two shorter insertions in domain 2 (FIGS. 4A-N). The functional role of these insertions is unknown.

4. PCR-Based Diagnostic Assay

Upon validation of TDAV genome sequence, a PCR-based diagnostic assay was developed to screen for the presence of TDAV in clinical specimens (e.g., serum). Eight candidate primer pairs targeting 130-200 nt products from across the TDAV genome were designed (Tables 3, 5). These and four previously described qRT-PCR primers for equine housekeeping genes were tested for performance in a SYBR green-based qPCR assay on samples collected from the outbreak. RNA prepared from the following sources were used to test these 1 primer pairs: three samples in which TDAV was identified by Illumina sequencing (the first samples collected from horses A1 and A2, and Antitoxin 2; these serve as confirmed positives for TDAV assays and suspected positives for equine housekeeping gene assays), three water samples (these serve as negative controls for both TDAV and equine housekeeping gene assays), eight specimens from horses treated with Antitoxin 1 (two available samples collected from horses A19, A20, A21 and A22; these serve as suspected negatives for TDAV assays, and expected positives for equine housekeeping gene assays), and two specimens from horses treated with Antitoxin 2 (two available samples collected from horse A18; these serve as suspected positives for TDAV assays and expected positive for equine housekeeping targets). Total RNA was extracted from 300 µl of serum specimen provided for the study as described in the Materials and Methods section of the manuscript. An aliquot of each sample was transferred to fresh tubes and provided to a second investigator to process in a blinded manner as follows: 2 µl of sample were used as template in random hexamer-primed 20 µl reaction with the Superscript III First Strand Synthesis System for RT-PCR kit (Life Technologies), according to the manufacturer's protocol. Resulting cDNAs were diluted 1:3 with nuclease-free $H_2O$, and 2 µl were used as input template for SYBR green qPCR assays with each of the 12 primer pairs in a reaction mix containing 7.8 µl $H_2O$, 0.2 µl 10 µM mix of qPCR primer pair, and 10 µl FAST SYBR Green Master mix (Life Technologies). The qPCR was performed on an ABI 7900HT Fast Real-Time PCR System Instrument as per manufacturer's recommended cycling parameters (95° C., 20 s denaturation step, 40 cycles of 95° C., 1 s, 60° C., 20 s), followed by dissociation analysis. The following criteria were used to identify primer pairs for calls on the presence or absence of viral RNA and equine host RNA prior to unmasking sample identifiers: a single peak in post-qPCR dissociation curve analysis and a single product of expected size in confirmatory agarose gel electrophoresis analyses; $C_t$ values for suspected positive signals <30; $C_t$ values for suspected negative signals >35; $C_t$ values for suspected $H_2O$ samples >39; a minimum difference of 9 $C_t$s between lowest $C_t$ value for negative calls and highest $C_t$ value for positive calls. A summary of results is provided in Table 6. TDAV primer pairs EVT146/147, EVT154/155, EVT162/163 and the equine housekeeping primers EVT192/193 met the above criteria. Using any one of these TDAV primers in combination with the EVT192/193 housekeeping primer pair yielded 100% accuracy in identification of the different sample types (TDAV+, TDAV−, or $H_2O$) tested in this assay.

TABLE 5

Primer pairs utilized in TDAV qRT-PCR diagnostic assay development

| Primer Pair Target (GenBank Identifier) | Forward Primer (Target coordinates) | Primer Sequence (5'-3') | Reverse Primer (Target Coordinates) | Primer Sequence (5'-3') | Amplicon Coordinates | Amplicon Length (bp) |
|---|---|---|---|---|---|---|
| TDAV | EVT-146 (171-190) | AGGGTTCTTCGGGTAAA TCC (SEQ ID NO.: 4) | EVT-147 (336-316) | CCCTCGGACTGAATTATA GGC (SEQ ID NO.: 5) | 171-336 (SEQ ID NO.: 28) | 166 |
| TDAV | EVT-154 (1674-1693) | GCTTTCCCTTTGCACTAT GG (SEQ ID NO.: 6) | EVT-155 (1829-1810) | CAAGCCGATGCAACTAA AGC (SEQ ID NO.: 7) | 1674-1829 (SEQ ID NO.: 29) | 156 |
| TDAV | EVT-158 (2144-2163) | GGCTCTTTGGATTCACTT GC (SEQ ID NO.: 8) | EVT-159 (2309-2290) | CCAGTGACCAGCATAAT TCG (SEQ ID NO.: 9) | 2144-2309 (SEQ ID NO.: 30) | 166 |
| TDAV | EVT-162 (3892-3911) | ATGCCATGGGTATGTTG ACC (SEQ ID NO.: 10) | EVT-163 (4046-4027) | CTCCTCGTAGTTGCCTTT GC (SEQ ID NO.: 11) | 3892-4046 (SEQ ID NO.: 31) | 155 |
| TDAV | EVT-170 (5607-5627) | TGGGAGTGTCTGGATTA TTGC (SEQ ID NO.: 12) | EVT-171 (5784-5765) | CAAGGTGTCCGAGAGGT AGG (SEQ ID NO.: 13) | 5607-5784 (SEQ ID NO.: 32) | 178 |
| TDAV | EVT-174 (6572-6592) | TGGTACTGGTACCGTCA CTGG (SEQ ID NO.: 14) | EVT-175 (6734-6715) | GCGAGGACCTGAAGTAG TGC (SEQ ID NO.: 15) | 6572-6734 (SEQ ID NO.: 33) | 163 |
| TDAV | EVT-178 (7834-7852) | CTCCTGTGCTCCCTGAAC C (SEQ ID NO.: 16) | EVT-179 (8000-7981) | AACACCATTGACCCAGA AGC (SEQ ID NO.: 17) | 7834-8000 (SEQ ID NO.: 34) | 167 |
| TDAV | EVT-186 (9931-9950) | CTTCTGCCTACATCCCAT CG (SEQ ID NO.: 18) | EVT-187 (10127-10108) | TGCATACCTTTCGGCTAA GG (SEQ ID NO.: 19) | 9931-10127 (SEQ ID NO.: 35) | 197 |
| equine 18S rRNA (AJ311673) | EVT-192 (1079-1096)* | ATGCGGCGGCGTTATTC C (SEQ ID NO.: 20) | EVT-193 (1282-1259)* | GCTATCAATCTGTCAATC CTGTCC (SEQ ID NO.: 21) | 1079-1282 | 204 |
| equine 28S rRNA (EU554425) | EVT-194 (4-24)* | CGGGTAAACGGCGGGAG TAAC (SEQ ID NO.: 22) | EVT-195 (112-89)* | TAGGTAGGGACAGTGGG AATCTCG (SEQ ID NO.: 23) | 4-112 | 109 |
| equine b-actin (AF035774) | EVT-196 (259-276)* | CACCACACCTTCTACAA C (SEQ ID NO.: 24) | EVT-197 (365-348)* | ATCTGGGTCATCTTCTCG (SEQ ID NO.: 25) | 259-365 | 107 |
| equine GAPDH (AF157626) | EVT-200 (86-103)* | GCCATCACCATCTTCCA G (SEQ ID NO.: 26) | EVT-201 (162-143)* | GACTCCACAACATATTCA GC (SEQ ID NO.: 27) | 86-162 | 77 |

*Zhang, et al. Determination of internal control for gene expression studies in equine tissue and cell culture using quantitative RT-PCR. Veterinary Immunology and Immunopathology 130, 114-119 (2009)

TABLE 6

Summary of TDAV primer pair performance in qRT-PCR diagnostic assay development experiments

| | PrimerPair | | | | | | | |
|---|---|---|---|---|---|---|---|---|
| | EVT146/147 | EVT154/155 | EVT158/159 | EVT162/163 | EVT170/171 | EVT174/175 | EVT178/179 | EVT186/187 |
| Expected Product size | 166 | 156 | 166 | 155 | 178 | 163 | 167 | 197 |
| Single peak in dissociation curve? | Yes | Yes | Yes | Yes | Yes | Yes | Yes | Yes |

TABLE 6-continued

Summary of TDAV primer pair performance in qRT-PCR diagnostic assay development experiments

| | PrimerPair | | | | | | | |
|---|---|---|---|---|---|---|---|---|
| | EVT146/147 | EVT154/155 | EVT158/159 | EVT162/163 | EVT170/171 | EVT174/175 | EVT178/179 | EVT186/187 |
| Single band by agarose gel electrophoresis? | Yes | Yes | Yes | Yes | Yes | Yes | Yes | Yes |
| positive Ct ave | 23.9998272 | 22.816635 | 24.073905 | 23.3769656 | 24.445335 | 22.9622892 | 24.0450046 | 25.262662 |
| positive Ct std | 1.952790687 | 1.845523611 | 2.071521833 | 1.949123321 | 1.882648998 | 1.772919767 | 1.97674361 | 1.803558843 |
| % stdev | 8.136686448 | 8.08850039 | 8.604843432 | 8.337794368 | 7.701465323 | 7.721006175 | 8.221015729 | 7.139227225 |
| positive Ct min | 22.629717 | 21.35401 | 22.62725 | 21.807777 | 22.744625 | 21.629707 | 22.624638 | 23.30096 |
| positive Ct max | 27.373388 | 25.947899 | 27.68374 | 26.708012 | 27.652481 | 26.053658 | 27.513517 | 27.984766 |
| negative Ct ave | 40 | 39.55607 | 32.94639491 | 40 | 37.97325245 | 36.52777509 | 38.88814582 | 39.49451136 |
| negative Ct std | 0 | 1.472349243 | 0.63249358 | 0 | 2.635299417 | 2.884971089 | 3.687603143 | 1.676516143 |
| % stdev | 0 | 3.722182823 | 1.919765673 | 0 | 6.93988333 | 7.898020293 | 9.48258927 | 4.24493451 |
| negative Ct min | 40 | 35.11677 | 32.020447 | 40 | 33.91935 | 33.245102 | 27.769604 | 34.439625 |
| negative Ct max | 40 | 40 | 33.749054 | 40 | 40 | 40 | 40 | 40 |
| pos Ct ave - neg Ct ave | 16.0001728 | 16.739435 | 8.872489909 | 16.6230344 | 13.52791745 | 13.56548589 | 14.84314122 | 14.23184936 |
| pos Ct max - neg Ct min | 12.626612 | 9.168871 | 4.336707 | 13.291988 | 6.266869 | 7.191444 | 0.256087 | 6.454859 |

5. Epidemiological Survey for the Presence of TDAV

An epidemiological survey was conducted to understand the prevalence of TDAV in horses, to investigate the correlation between clinical symptoms and viremia, and to determine whether there is natural animal-to-animal transmission. A qRT-PCR-based TDAV assay was developed (see above) and employed to screen serum or plasma from 60 horses from three geographically distant facilities. Farm A, on which the Theiler's disease outbreak took place, provided samples from 37 horses. Some grazed common fields or were housed in common stables. Horses from Farm A stratified into three sub-groups: 15 horses had not been treated with botulinum antitoxin, 17 horses (including Horse A1 and Horse A2) had received the contaminated Antitoxin 2, and 5 horses had received the untainted Antitoxin 1. Farm B was located in a different state than Farm A and serum was analyzed from 20 Farm B horses with no history of exposure to antitoxin from either source. Farm D (donor) was the facility in which the botulinum Antitoxin 2 had been prepared by pooling plasma from three botulinal toxin-immunized horses; samples from the three donor horses were provided.

The results of the TDAV qRT-PCR detection assay are displayed as $C_t$ values plotted on an inverted y-axis (FIG. 5A). Of the 17 horses exposed to Antitoxin 2 on Farm A, 15 displayed low $C_t$ values, indicating TDAV positively. The two Antitoxin 2 treated horses (A7 and A11) that were seemingly negative by the qRT-PCR assay using primers EVT-146/-147 displayed a positive signal in some of the qPCR replicates in a parallel analysis of these samples with the EVT-162/-163 primer set; this suggests that these animals may have developed an infection with TDAV titers hovering around the detection limit of the assay. Not a single replicate qPCR from an animal that was not exposed to Antitoxin 2 displayed a positive signal in either TDAV diagnostic assay. All (40/40) untreated or Antitoxin 1 treated horses from Farms A and B were negative for TDAV. Of the three donor horses from Farm D, two animals were TDAV negative, while one was positive; this animal is presumably the source of the contamination in Antitoxin 2. These results establish a strong association of TDAV infection with Antitoxin 2 exposure, and additionally suggest the virus is not highly prevalent in untreated horses. Furthermore, the fact that TDAV was not detected in horses on Farm A that did not receive Antitoxin 2, despite contact with TDAV-infected horses for 1 year, suggests that TDAV was not readily spread between horses.

During the Theiler's disease outbreak on Farm A, animals were broadly classified as either having hepatitis not having hepatitis. Horses with hepatitis were further stratified into horses that were "clinical" and "subclinical." The clinical cases displayed significant elevation of liver enzymes in the serum along with common clinical signs of disease such as jaundice, lethargy, poor appetite and photodermatitis. The subclinical cases displayed varying degrees of elevation of liver enzymes in the serum, but with no overt clinical manifestations of liver disease. To investigate the correlation between viral load and clinical presentation, the qRT-PCR assay data from the Antitoxin 2 exposed animals were stratified by hepatitis status and symptom level (FIG. 5B). Since the range of $C_t$ values (representing a viral load of $10^6$-$10^8$ genomes/ml; SI Materials and Methods) was similar for both hepatitis-positive and hepatitis-negative horses, a correlation between hepatitis status or clinical symptoms and viral load was not apparent. Moreover, within each group (hepatitis-positive and hepatitis-negative) a single horse (A7 and A11, respectively) with a viral load that fell below this range was observed, which further supported the conclusion that the viral load is not predictive of the extent of hepatic injury.

6. Experimental Inoculation Study

To better understand the dynamics of TDAV infection and the role of the virus in disease progression, a small experimental inoculation study was performed. Four horses that were healthy and free of clinical or biochemical evidence of liver disease according to initial evaluations were administered standard doses of Antitoxin 2 (same lot as involved in Farm A outbreak). For the next 10-14 weeks, the animals were monitored daily for overt signs of illness. Serum specimens were collected on a weekly basis and tested for biochemical signs of liver injury and quantification of TDAV serum levels.

Over the course of the study, only 1 of the 4 animals (Horse C1) displayed clinical signs of illness. The symptoms, which arose approximately 7 to 9 weeks after inoculation, included a brief period of mild lethargy and diminished appetite, and appeared to resolve within <1 week. Consistent with the observation of clinical signs, Horse C1 had elevated liver enzyme levels in the serum that peaked within the week prior to the onset of illness (FIGS. 6B-E). Serum liver enzymes for Horses C2-C4 remained largely unchanged over the course of the study, with the exception of a transient elevation in GLDH and SDH levels at week 7 in horse C3.

The dynamics of TDAV infection were remarkably diverse among the four inoculated animals (FIG. 6A), paralleling the differences in viral loads detected following the initial outbreak (FIG. 5A). In Horses C1 and C3, TDAV levels climbed rapidly and remained elevated from week 4 for the duration of the study. Importantly, the near maximal viral load in Horse C1 pre-dated the onset of peak clinical symptoms by at least 5 weeks. Indeed, there were three weeks (week 4-week 7) during which viral load was maximal but no signs of hepatic injury were evident, as judged by AST, GGT, SDH or GLDH levels. In Horse C4, viral load gradually increased and peaked later (week 8) and at lower levels than for Horses C1 or C3. In Horse C2, TDAV was detected from week 2 onward; however, the viral load was very low relative to the other animals and did not rise substantially over of the course of the study.

7. Acute TDAV Infection can Become Chronic

Figure 7:
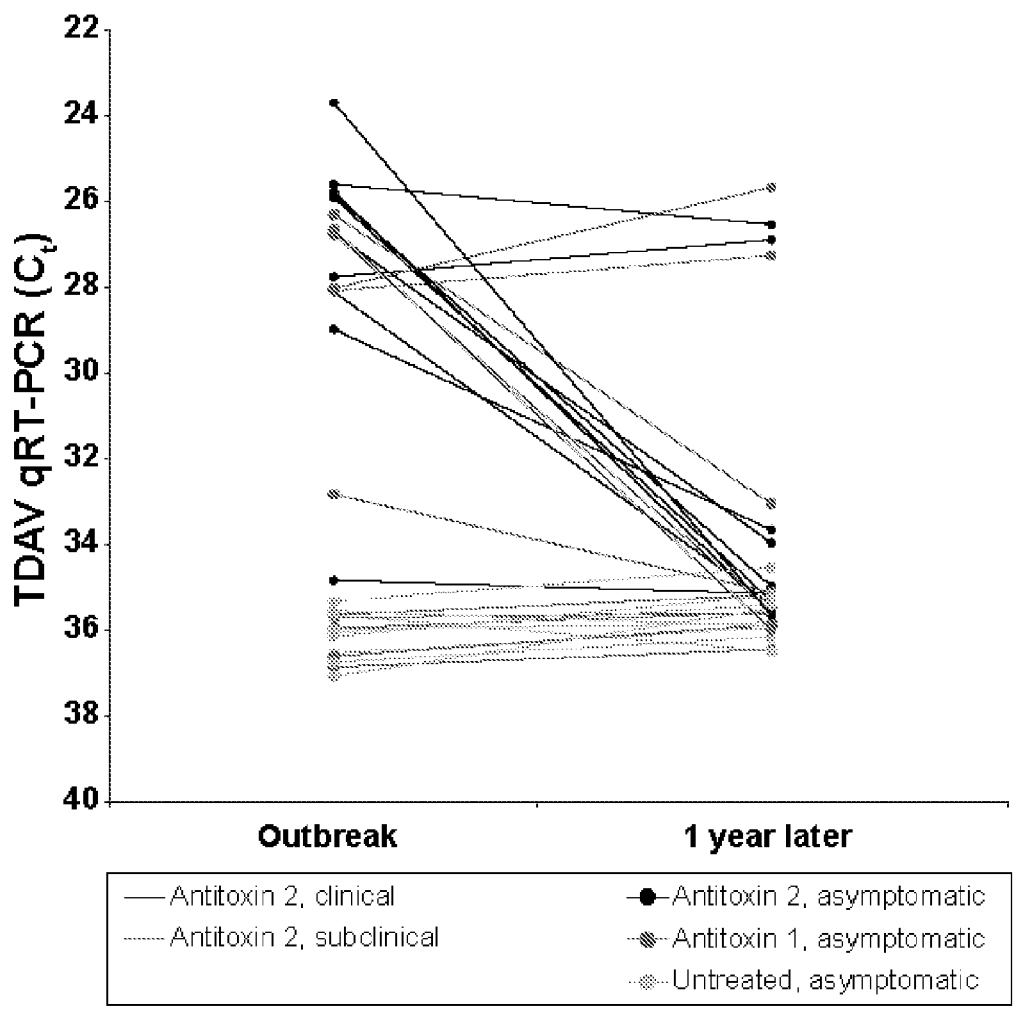

GB and hepaciviruses are known to cause chronic infection in some individuals. To examine the potential of TDAV to progress to chronicity, serum samples from thirty animals on Farm A were collected approximately one year after the initial Theiler's disease outbreak. In both index cases (Horses A1 and A2), which were TDAV positive and displayed clinical signs of illness during the outbreak, the virus was not detectable one year later (FIG. 7). Similarly, 10 other animals that had been TDAV-positive during the outbreak (including Horses A7 and A11, which had a very low viral load during the outbreak) were unequivocally negative for the virus after one year. In contrast, four horses without overt clinical symptoms during the outbreak continued to harbor TDAV one year later, demonstrating that TDAV can establish chronic infection in some, but not all exposed animals. Finally, all horses that were TDAV-negative during the outbreak continued to be negative at one year, indicating inefficient, if any, horizontal transmission from infected animals on the same farm.

Figure 5:
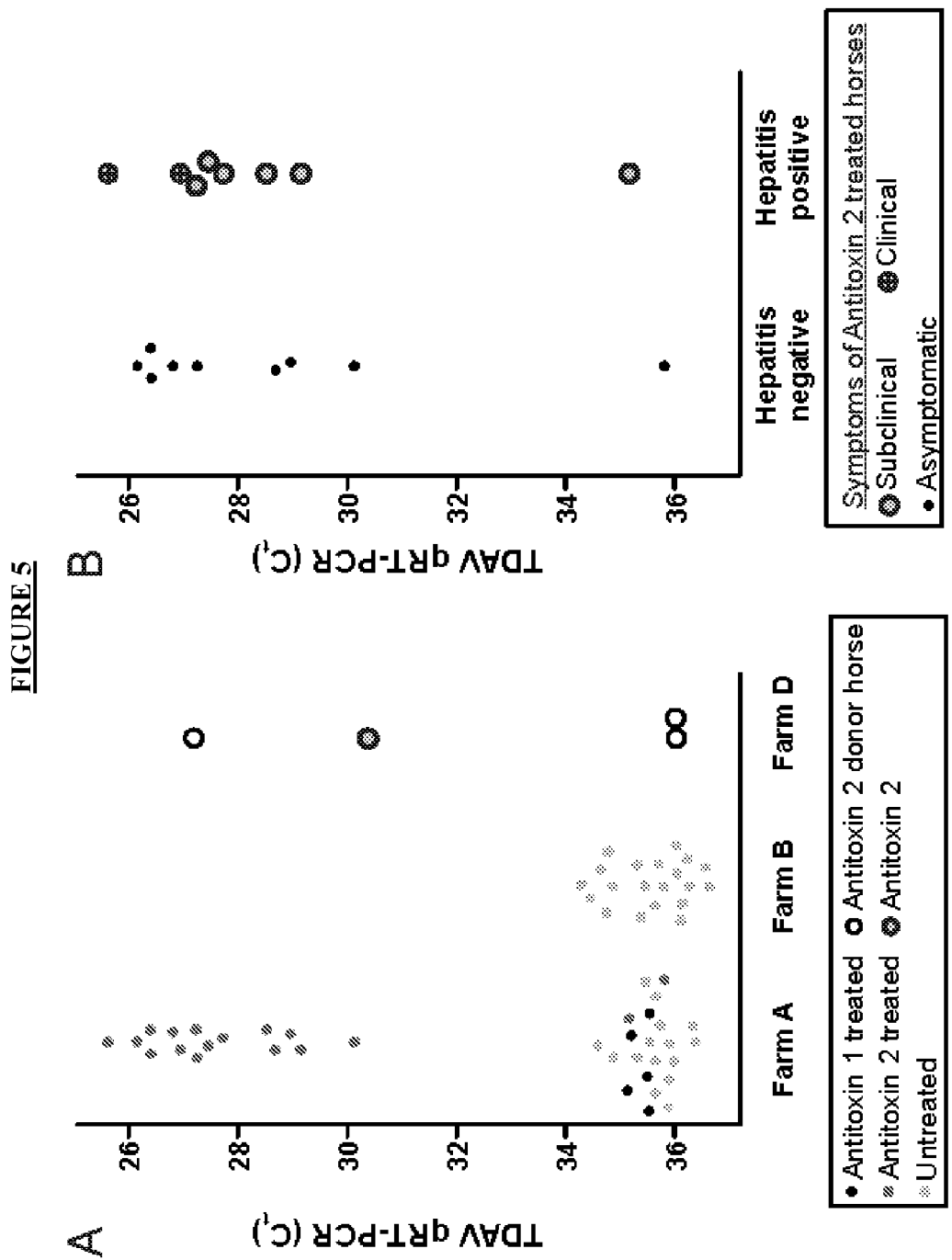
FIG. 5. A quantitative PCR-based diagnostic assay to detect TDAV in different cohorts. Cycles to threshold ($C_t$) from the qRT-PCR TDAV diagnostic assay (primers EVT-146/147) are plotted on an inverted y-axis; a lower $C_t$ value represents a greater viral load. (A) Serum/plasma from horses on Farms A, B and D with antitoxin treatment status indicated. (B) Results from Farm A, Antitoxin 2 treated animals only are segregated by whether the horse displayed signs of hepatitis. The severity of symptoms (clinical and subclinical) is indicated.
Figure 6:
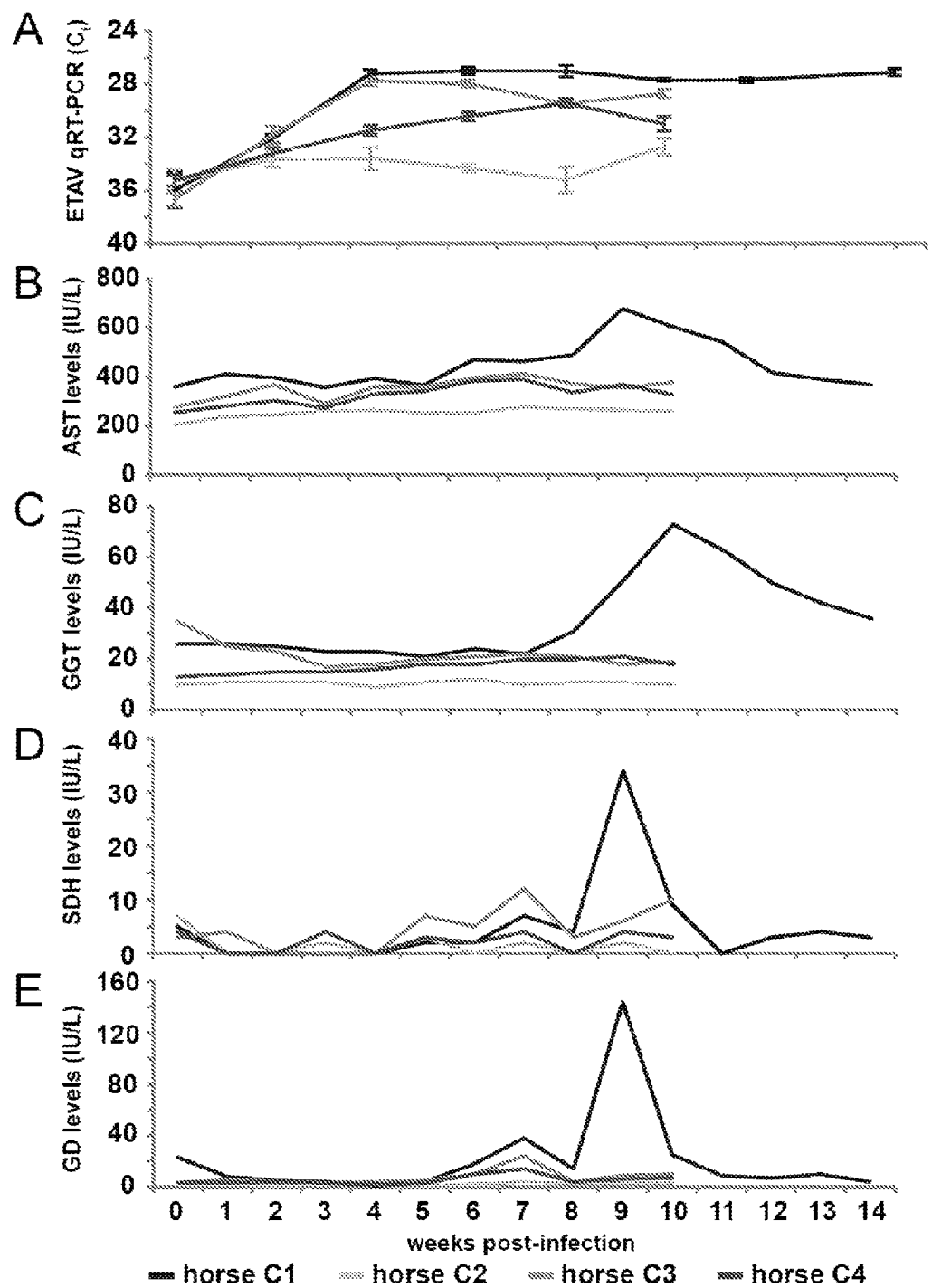
FIGS. 6A-E. TDAV viral load and liver enzyme function in animals experimentally inoculated with Antitoxin 2. (A) qRT-PCR quantification of TDAV RNA. (B-E) Biochemical tests for aspartate amino transferase (AST), gamma gluatamyl transferase (GGT), sorbitol dehydrogenase (SDH), and glutamate dehydrogenase (GLDH or GD). Samples were taken at time 0 and 10-14 weeks after inoculation with 500 mL of the same lot of Antitoxin 2 linked to the serum hepatitis outbreak. One horse became mildly symptomatic at week 9 post inoculation (Horse C1, black), while the other three did not (Horse C2, light gray; Horse C3, gray; and Horse C4, dark gray).

The above-described TDAV diagnostic assay provides for the detection and/or identification and/or quantification of TDAV in a biological sample (e.g., serum). The TDAV qPCR-based diagnostic assay was employed to screen serum or plasma from an 60 horses from three geographically distant facilities (FIG. 5). None of the 20 animals from the Farm B cohort had received botulinum antitoxin from either source. Botulinum Antitoxin 2 was prepared by pooling plasma from three botulinum toxin-immunized horses on Farm D; these three donor horses comprise the Farm D cohort. Finally, Farm A, on which the hepatitis outbreak was detected, provided samples from 37 horses. Some of the 37 Farm A animals grazed common fields or were housed in common stables. These horses may be stratified into three sub-groups: 1) fifteen of these Farm A horses had not been treated with botulinum antitoxin from either source and serve as the Farm A, untreated sub-cohort; 2) seventeen horses (inclusive of horses A1 and A2) from Farm A had received the contaminated Antitoxin 2 and comprise the Farm A, Antitoxin 2 treated sub-cohort; and, 3) the remaining five horses were from animals that had received Antitoxin 1 and comprise the Farm A, Antitoxin 1 treated sub-cohort. Thus, the diagnostic assay described herein may be used to, for example, determine: i) how widespread TDAV infections in horse populations; ii) to detect natural animal-to-animal transmission; iii) to determine the correlation, if any, between clinical symptoms and viremia; and, iv) whether TDAV infections are cleared and/or established as chronic long term infections As described herein, massively parallel sequencing and subsequent nucleic acid-based screening was utilized to identify a previously unknown, highly divergent member of the Flaviviridae and link it to an outbreak of Theiler's disease in horses. This virus, which we have termed Theiler's disease-associated virus (TDAV), is the first infectious agent to be unambiguously associated with equine acute serum hepatitis since the first description of the disease in 1918. Several lines of evidence implicate TDAV as the causative agent in this outbreak of Theiler's disease in horses. First, TDAV was the only virus common to all of the index cases, and there were few non-TDAV viral sequences detected in any of the samples. Second, although not all TDAV-positive horses had hepatitis, TDAV was detectable in every animal in the outbreak with clinical or biochemical evidence of hepatitis. Third, TDAV positivity was exclusively associated with antecedent exposure to Antitoxin 2, supporting the hypothesis that it was an infectious contaminant of the serum product and not a virus routinely found in farm horses. Fourth, the inoculation study indicated that TDAV infection precedes liver injury, excluding the possibility that the association of virus with hepatitis on Farm A reflects preferential infection of animals with antecedent liver injury. Finally, sequencing of the TDAV genome revealed a member of the Flaviviridae, which encompasses other blood-borne viruses linked to liver injury, including HCV. It is noted that this inoculation study does not formally fulfill Koch's postulates, as the TDAV in the inoculum was not first purified by cultivation in vitro (since we have yet to develop suitable culture systems). As such, the association of TDAV with Theiler's disease, while very strong, remains inferential. Similarly, it remains to be determined whether TDAV is the sole etiologic agent of Theiler's disease or one of several causative agents—as is the case in human hepatitis, which is linked to at least five unrelated viruses (hepatitis viruses A-E). In this regard, we note that we have been unable to link NPHV, the only known hepaci-like virus detected in horses, to hepatitis in this outbreak. Parallel qRT-PCR assays for NPHV RNA performed in this study identified the virus in only three horses: one TDAV-negative untreated, asymptomatic horse (Farm A), one asymptomatic TDAV-positive horse (Farm A), and one TDAV-negative horse with no history of antitoxin treatment (Farm B) (Table 7). Of course, this does not exclude a role for NPHV in hepatic (or extrahepatic) disease in other epidemiologic settings.

TABLE 7

| NPHV qPCR screening* | | |
|---|---|---|
| Horse ID[†] | Average $C_t$ (S.D.)[‡] | NPHV Call |
| A1 | Undetermined | Negative |
| A2 | Undetermined | Negative |
| A3 | Undetermined | Negative |
| A4 | Undetermined | Negative |
| A5 | Undetermined | Negative |
| A6 | Undetermined | Negative |
| A7 | Undetermined | Negative |

TABLE 7-continued

NPHV qPCR screening*

| Horse ID[†] | Average $C_t$ (S.D.)[‡] | NPHV Call |
|---|---|---|
| A8 | Undetermined | Negative |
| A9 | Undetermined | Negative |
| A10 | Undetermined | Negative |
| A11 | 34.122558 (0.269914587) | Positive |
| A12 | Undetermined | Negative |
| A13 | undetermined | Negative |
| A14 | undetermined | Negative |
| A15 | 28.177337 (0.221504356) | Positive |
| A16 | undetermined | Negative |
| A17 | undetermined | Negative |
| A18 | undetermined | Negative |
| A19 | undetermined | Negative |
| A20 | undetermined | Negative |
| A21 | undetermined | Negative |
| A22 | undetermined | Negative |
| A23 | undetermined | Negative |
| A24 | undetermined | Negative |
| A25 | undetermined | Negative |
| A26 | undetermined | Negative |
| A27 | undetermined | Negative |
| A28 | undetermined | Negative |
| A29 | undetermined | Negative |
| A30 | undetermined | Negative |
| A31 | undetermined | Negative |
| A32 | undetermined | Negative |
| A33 | undetermined | Negative |
| A34 | undetermined | Negative |
| A35 | undetermined | Negative |
| A36 | undetermined | Negative |
| A37 | undetermined | Negative |
| B1 | undetermined | Negative |
| B2 | undetermined | Negative |
| B3 | undetermined | Negative |
| B4 | undetermined | Negative |
| B5 | undetermined | Negative |
| B6 | undetermined | Negative |
| B7 | undetermined | Negative |
| B8 | undetermined | Negative |
| B9 | undetermined | Negative |
| B10 | undetermined | Negative |
| B11 | undetermined | Negative |
| B12 | undetermined | Negative |
| B13 | 33.9393255 (0.791101946) | Positive |
| B14 | undetermined | Negative |
| B15 | undetermined | Negative |
| B16 | undetermined | Negative |
| B17 | undetermined | Negative |
| B18 | undetermined | Negative |
| B19 | undetermined | Negative |
| B20 | undetermined | Negative |
| D1 | undetermined | Negative |
| D2 | undetermined | Negative |
| D3 | undetermined | Negative |
| positive control (plasmid) | 8.85176075 (0.453810734) | Positive |

*Burbelo, P.D., et al., 2012. Serology-Enabled Discovery of Genetically Diverse Hepaciviruses in a New Host. Journal of Virology. 86(11): 6171.
[†]Horse identifiers are coded according to farm location and a unique number assigned to each horse sampled for this study (A, Farm A where the outbreak occurred; B, non-outbreak Farm B located in a different state; D, donor horses whose serum was pooled to make the ETAV-contaminated Antitoxin 2 serum linked to the Theiler's disease outbreak on Farm A.
[‡]$C_t$ = cycle threshold.
S.D. = standard deviation, n = 4.

The closest relatives of TDAV appear to be the GB viruses. GB viruses are a group of highly prevalent Flaviviridae species that produce persistent but typically subclinical infections in their host species. GB viruses A, B, and C were first identified in studies of non-A non-B serum hepatitis in humans and non-human primates in the early 1990s, though none have been unequivocally linked to human liver injury in subsequent epidemiological investigations (*Proc. Natl. Acad. Sci. USA*, 19; 100(17):9962-7. Epub 2003 Aug. 7, Chronic hepatitis associated with GB virus B persistence in a tamarin after intrahepatic inoculation of synthetic viral RNA).

GBV-D, also thus far unlinked to disease, was recently identified in a serum survey of frugivorous bats native to south central Asia. Based on observed similarities in genome organization and sequence, tissue tropism, lack of detectable pathogenicity in humans, and the persistent nature of infection, it has been proposed to classify GBV-A, GBV-C, and GBV-D together in a new Flaviviridae genus termed pegivirus (persistent GB or G virus). At present, based on sequence features, TDAV would likely be considered a member of the proposed pegivirus genus, though it would be the first member for which a disease association has been identified. Membership of a virus in a given genus doesn't necessarily connote its natural host. While TDAV has been discovered in horses, the natural reservoirs and hosts of this virus are unknown; it could be an exclusively equine virus, or an agent introduced into the equine population from another source and amplified there by the practice of transfusion.

Divergence from Flaviviridae family members is evident in several interesting features of the TDAV genome. First, the virus harbors three amino acid insertions in the NS5A protein spanning approximately 160 amino acids not found in any of the related hepacivirus or GB virus species. HCV NS5A is a phosphoprotein with no known enzymatic activity but an essential, though poorly understood, role in the viral life cycle. NS5A is required for RNA replication, infectious HCV assembly, and interactions with a variety of cellular proteins; the protein is also the target of the most potent anti-HCV inhibitors discovered to date. The largest TDAV NS5A insertion resides in the equivalent of HCV NS5A domain I, a zinc-binding region with RNA-binding activity; the relevance of the insertions in the TDAV life cycle is not known. Second, TDAV lacks a microRNA (miR)-122 binding site in the 5' UTR that has been detected in the hepaciviruses. In humans, miR-122 is an abundant liver-specific miRNA, which is essential for HCV replication. The role, if any, that miRNAs play in TDAV replication remains to be determined.

While genetically distinct from the hepaciviruses, TDAV resembles HCV in several elements of its biology, including the ability to engender both acute and chronic infections that can present with symptomatic or asymptomatic infection. TDAV is a blood-borne virus that showed no evidence of horizontal transmission via normal contact between uninfected and infected horses on Farm A over one year. This also resembles HCV, which is rarely transmitted by casual nonparenteral human contact and is inefficiently transmitted by sexual contact; indeed, for HCV as for TDAV, parenteral exposure appears to be the most efficient route of transmission. Of course, the absence of horizontal TDAV transmission observed in this study does not entirely preclude its occurrence, and vertical transmission also remains a possibility. As observed for HCV, TDAV-positive individuals may be asymptomatic for prolonged periods. Furthermore, as in HCV, TDAV serum RNA levels are not strongly correlated with the severity of clinical disease. This may indicate that viral replication itself is not cytocidal, and that damage to hepatocytes, where present, may result from secondary immune or inflammatory mechanisms. Finally, acute HCV infections can clear without any intervention in some individuals, although approximately 70% can progress to chronicity; in this study, we observed an TDAV chronicity rate of 4 of 17 (23.5%) animals after one year.

The availability of a qRT-PCR-based TDAV diagnostic assay and the future development of serology-based assays will permit screening of equine biologic products, as well as further investigations of TDAV prevalence and exposure. These studies provide insight into the expanding world of non-primate Flaviviridae, open opportunities to investigate an important pathogen of horses, and provide critical information for the control and potential eradication of equine serum hepatitis.

For the purposes of interpreting this specification, the following definitions apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended. It is noted that, as used in this specification and the appended claims, the singular forms "a," "an," and "the," include plural referents unless expressly and unequivocally limited to one referent. The use of "or" means "and/or" unless stated otherwise. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of." The section headings used herein are for organizational purposes only and are not to be construed as limiting the subject matter described. All documents, or portions of documents, cited in this application, including but not limited to patents, patent applications, articles, books, and treatises are hereby expressly incorporated by reference in their entirety for any purpose. In the event that one or more of the incorporated documents defines a term that contradicts that term's definition in this application, this application controls. All references cited herein, including patents, patent applications, papers, text books, and the like, and the references cited therein, to the extent that they are not already, are hereby incorporated by reference in their entirety. In the event that one or more of the incorporated literature and similar materials differs.

SEQUENCE LISTING

```
TDAV nucleotide 120618
                                                    SEQ ID NO.: 1
TGATACCGTGTCCCGGTACGACCTCGCGCGTCCCCAAGCTCGCCCTGAGGGGGAGCGT

AAGGGCGCGTAGTGGGGTAGCCCCCCAAACCGAGCCACCCTAGTGAGTGACTTTAGAAT

GGTTAGGGAGACTACCGCCTTCGCTGTTTGGGGACCTAATGATCCGCGTGCCAGGGTTC

TTCGGGTAAATCCCGGCGCGGTGTTTTGGGTTCAGGGCAGTAGGGGCAGACGGGCCAGC

AGTCGCTGGTTCCTGGTACCACCACCCTATCCGGACGACCTCCCTCACGAAAGGTCGCC

ACGGTCTGTGGCTCGACGACGCCTATAATTCAGTCCGAGGGCGCAGCCCTCGTTAAAC

TTAGGCAAGGTTCCTCGCCATTGATTTGGCCAGGGGTTTAAGTGAACGCCGCCCTTTTA

ATGTTTAATAGGGTTCTTTCCCGGCGGGTTGACAAACACTTCCCTGGGCTCTTCGTTGG

CCTCGGTTCCTTGATGCTTCGGCACCCATGAGCGCACAGGGGGGGGACCCTGCGACAGT

CCGCCAAGAGGAAAATCCTTCGGGTGACCTCGTGCGCAACCCAATCCCTTCTTCTTCCA

CATGGCGTGTCTGTGGTGCATGCTGTGATGGCGCCTTTCTTGTTGCTGGTTCTTTTGTG

CGGGGCCGGTGCTATCCGCGCCCCGCCTCACACAAATGTTCCTTCAAAGGCCGGTTTT

ATCTGTCAAACTGCTGTGATCCAAAGGACATACTGCTCTGCACTTACGACTTCTGCGTT

ACCCGCGTTGGTTGTCATGTGTGCACAGAAGTTTGTTGGAACGTCTCTCGTCCTGGCAT

TTCTGTTCGACCCGGTTCAGGTGATGTGGAGCCCGACCTTAAGGGGTTCTTCTCGGTCG

CTGCGGTGGGTGGCTATGCTGCCTCCCTCATCGGCCTCGGAGAGCCTTTTTCTGTCGGC

TTGCTTGGCCTCACCATCCTTTACCGGGTTGATACTGGGGTTCCTGACGGGTTGCGTTG

CGACAGACCTTGCAATGTGTCAGTTCCCGTTTGGCCCTCGTCCCTCGAGGGGATGCGGG

TCTTGTGGGAAGTTGTCTGGGGTTTGCTGTACCGCATTCCGCACATGATTTGGGCAGCC

TTTAACATCTTCGATGTGTGGTTGTTGGGTCTAGTCATCCTCCTTACCCTGGAGGGTCG

CTGGCACCTGGCGATCATGCTCGTCCTTGCCGCTGGCTTGTCTACTTCTAGTGCTGAAC

TTGTTGGGGAGCCATGGGACTCATGCACCTGTAAGGGTGTTGTGGGTCTTAGGCACCTT

AACGAGACTACTTCTCCATGTCTCTGTGAAAATGGCCCTTGGTACTATGATGCTGGTAC

GCCAGGCCTCACCTCTTTCGAGAGGGGGGTGGCTACTGTCCTTCCCGATCGGTCCGCA
```

```
GGTCCGGATGCTCGCTGTGGTGCCAGTGGGGATCGTGGGTTACTATCTACCCTCCCTCC
TGGCCTAACGGCCGGCATTCTTGGCTCTGTAATTGGCGGTGTTGGTGCAATGGTCGCCG
ATGCTGGATTACCTGCCTCGTTGACGCACGTCGACATTGGTGTGGTTCCTGCGTCCGCG
ATTGTTGGGCTGAGACCGCTGATGATTCTCTTACCTTCGGGAACTGTGGCACTGGCCCT
CGCGTCACTGCTAACTTAACCGCTTTCCCTTTGCACTATGGTCAGAAATCTACTGTTGC
TTTGGCTACTAAAATGGTCTTGACTGCTAAATTACAACCCTTGTGGAGGAATCTTAACA
CTACCATTATGTGCTCAGTTATTCGGACTTCTGTCCATTGCTTTAGTTGCATCGGCTTG
CCGTCGCCTCCCGCGGGTTTGTGGGAGCGTGTCCCGGGCGAACCCATTTCTGATTGTGA
AGGCGTGCAGGTTTCCACTGGTAAGCGGACTCCCACATGCCCAACCAAGCAGAGGTGGA
ATGCTACTGTGCACGTCTGCCCCGGTTACGCCTTCTACTCTCCCGCGTATGATGATGGC
GAGCTTCATGTTGCTGGCTACTGGCAGTGGCTTTTGGCCGGACGCACTATTCACTTTTG
GTTTCTTGTAGATTTCCTGCTTGTTTACTTGTTCTTGATGCACCTCTCTGGTGCGCGCA
TCACCCCCTTTTTAGCCTTGGCTCTTTGGATTCACTTGCGGGGGGGGGTCTTTGGATCC
CCCACTCCGATACCTGGCTGCAAAAATAAGAATGAAGCCATCCACAACTACACACACTG
TGTCCAGGCTCTTGGTCACGCCATTAGCGTGGTTGGTGAGGCGAGTGCGAATTATGCTG
GTCACTGGCTGCTACAGGGCCCGTTTACCGGTCTCTCGTGGATAGTCAACGCCACGTCG
TCCGCATTCAATATCACCTCCCATGCCTTGACCACTGTCGGCTCTACACTGTCATCACT
GGCTGAGGCTTGGATTCCCTTGGGCGGGGCCTCACATCCCCTCGCTCCTTCCACAGGCA
GTTTAGCGGCGGCGATCCTAGCGCCGTGCGCCTCTTGTGCTCCTGCCGCTTGGTTTAGC
GCAGCTCCCATGCTAGGCTGGGCGTTTCGCTATCCCACTTGGCACGAGTCCATTATGGC
TCTGCTTTTGGTCCTGATTTACATGAGGTTCGCCGGGGTCGCTCGGCTTGCCGCTCTGG
TTACTTGGAAGTTGACTCGCAACTTCGGCGCTGTTGGTGTGCTCGTCCTCCTAGTGCTT
GCGCGTAGGAAGACCAGTGCTTTGGGGTACGAGATCTGTATTTCCCTTACGGGCGAGGC
TGATTGGGACTGGTTGGATTTTTCCTCCTGGCTCCTCTCGCTTCTGTTCGCTTGGGCAG
TGCTTGCTCTCGCGTCCCTTACACCAGCAATGAAGAAGCGTAAGCTCCGATGGTACTCT
CGCTGGGCTTGGTGCTACTCTCGGTTCATCTCGTGGGTCGACCACACTCCATTCAACGG
TGTAGATCCCCTTTCTCGGAAGGCTTCCTACTACTGGCTGTTTGCGGGTCTGGTTTGGC
CTAACGAGGTTGCCGTTGTGGTTGCCTCGTACGTCTTGATTGCCGTCGTGGTTGACTTG
ACTGACATTTTACTAGAGACCCTCTTGTTGTCAAATCCTGATCTGGGAAGGCTCGCGGT
GTTGTGTGACACCATCGCGGGTCTCAGGTCTCCCTGGTTCCTCCATTGGGTTCTGGAGC
GCGCAGCTAGGCGTGGCATTTACCTCTATCACCACCAGGGGCATTTGTCCGCACGGCTC
GCACAGTATCTCAGGGAGTTGGATGGTGCCTTGGAGCCGGCGCGGGTTACGCCGCAGGA
CTGCGAGTTTGTGCGCGACGCTCAGCGGATTCTTGAGTGTGGCCGCAATTATCGCGGGA
AGGCGGTTGTTGCCCGCAACGGTGACACTGTCATCATTGGCGCCGTTCGCGGGGCCTGG
GAGCTCCCCCCCGGGTTCGTGCTTACGGCCCCCCTCATGCTTCGAAGCGTTGGCCGTGG
AGTCTGGCAGACGCTAGTGACGAGCATGATGGGGAAGGACAAGGAAGATCACACAGGCA
ATGTCCTTATCCTTGGGACCGCTGCCACCCGGTCAATGGGGACGTGCGTCGGGGGGGTG
GTTTACACCACATTCCACTCCTCCAACGGTCGGACTTTGGCTGGGCCAACTGGGCCCCT
AAATCCTCGGTGGTGGTCGCCCTCGGACGACACCGCCGTGTACCCAATGCCTGTAGGCT
GCAGAAGTCTAGAGATTTGTGGATGTGGAGCCCGGAGCGCATGGGTACTGCGCAAGGAT
GGTGCTCTAGTCCACGGTGAACTGTTTCCTGGACGTGAGATTAGACTGGATGTCGCTGG
```

-continued

```
TCGTGTTGCAGACTTTAAGGGCGCATCAGGTTCACCCATACTCTGTGACCAGGGTCATG
CCATGGGTATGTTGACCGCGGTGTCGCATCGGGGGCCGGAAGTACACTCGGCCCTCTTT
GTCAAGCCGTGGGACAGCGTTCCCAGGGATGCCCAAACGGTTACGGACGTGGGTGCACC
TCCTGCGGTACCTGGCAAAGGCAACTACGAGGAGCGATCCTTGTTCTTGCCCACTGGCA
CTGGCAAGTCCACCCTTGTCCCTGCCAATTATGCCAAGTCAGGCCACAAGACCTTGGTT
CTGAACCCGTCTGTTGCCACTGTTGCCGCCATGGGTCCTTACATGAAGGACAAAATGGG
CATTACACCGTCCATCTTTGCTGGCCATGGGCCCACCGCTATCTCGCGCAACACTGGGT
CTAACCTGGTGTACGCGACTTACGGTCGTTTCTTGGCCAAGCATAAGCAGTTGCTGGAC
GGTGTCTCTGTTATTCTTTGTGATGAGTGCCACAGCTCAGACCCGACAGTATTGTTGGG
TATTGGGCTGGTGCGCTCTGAAGCGAAGAAGGCCGGAGTGAACTTAGTTCTCTTCGGTA
CAGCTACACCACCTGGCTATGCTACAGTCCCTCATAAGAACATCACGGAGGCACCGGTT
GGGACGGATGGTGACATTCCATTCTATGGTTTCTACTTGAAGTCCACTAACTACACCAC
TGGCAGACATCTGATCTTTGTCCACTCTAAGAGTGAGGCGGAGCGCGTCGCCTCCGCTC
TTACTGCTAAGGGCGTCAAAGCTATGTTCCACTACTCAGGTCGGGATCCAACCGCAATC
CCCACCACTGGTAGTTTGACCGTAGTAGCCACCGATGCCCTTAACACAGGATACACAGG
TGACTTTGATACGGTGACGGACTGCAATGTGGCTGTGCAGGAAGAAGTTACCGTTGATC
TTGAACCTACCTTCACCATTTCTCTTCGCACTCGGCCAGCTACGGCTGATCTGCGTGCC
CAGAGGAGGGGGCGTTGCGGTCGCGGCAGGCCTGGCCTGTACCGTTACTGTATAGCCTC
TTCCCCGCCTTGTGGCACGGTCCCATCCGGGGCCGTTTGGGCCGCTTTTGACGCTGCGC
TGACTTGGTACGATATTCAGCCCGCCGCCGCTGCGCGGTTGATTGGACTTTTTGCAGAG
TGCCCTTACACCGGGCACATTGGCGTAAACTTGCAGGACCCCCAGCGGGTCTATGAGGT
CCTCGCTCCGTTTGCGCTGACGCCAGACGTAGTGAGAGCAAGGAACGCCGGGGTCAGCT
GGCCCCTCCTCGTTGGAGTCCAACGGTCAGAGTGCAAGCGCTGCGCCTCAGGTCCTCCT
TCCAACGCCCCCCACTGGCAGGGTTTGGTCGGCGATTGTGCCGTTCCGCTGCTTTACGC
CTTGGAGACTCAGAGGCCCGAGAGGGTAATCCGATCTCCATTGGTCGATCAATTGGCTG
CGGCCTTGGGCGACTCTGTTACAGAGACGTCCTCTGGCCCCATCCTTTTGGCCGGCTTG
GCGTTGGCTGCGGCCGCTGCTATTGCTGACTACACCGGGACTTTGGTGGTCGTTGGGAC
CTTTGACGTGCGCCCTGGGGGGGCTCCGCGGCCTCCCCAATCGCGCGATCTGCCCGGCG
GATTATCATCAGGACAGCCACAGAGTGATGGCGAGGGGCCTCCCCCTCCCCGTCGCACT
GACCAGCTGACAGACTCCCAAACTTTGGACGCACTCCAGGATGTGATGACCCAGACATC
GTGGGAGTGTCTGGATTATTGCTACCGGGTAGCGACCGGTACCCTGGCTCCTAGAACCG
CCGACGCGCTGGAAAGCGGGGCGCGTTGGCTTCGGGAGGCGTGCTGTGGGACTAACCCT
CCCACTAGTCCATTCCCAGGTGGGTGGGGGGTCACCCAACCCCTACCTCTCGGACACCT
TGCTGTGAAGGCTTGGCAAACCTTGCTCAACAACTTGGGTACTGCTATTTCCCTGGTCA
CCGCGGCCTGGGCCGCTGGTAGTTCTCCTCCGCTTGCTTGTATCGCCTCAGCGTTGCTT
GGGTTGCAAAGCGCGTTGCCGCTCGACGTGCGCCTCCCGGCCGCTCTCCTTGCTGGTGC
CGGTGGCACTCTCTTCGGAGATGCCGCCACTGGCTTGGGGATGGCCGCGTCGTTCATGT
TGGGTGGCACGGTTGGAACCGCTGGCCCTTTCATGTTCCTACTTGAAGTCTTGGGGGGG
TATGAGTCGACGGTGGTCGGCGCCTCCCTTGCATTTGACCTTTTTTCTGGAAACGCTTC
TATGTCAGACTTGGTTTACCTAATCCCTGCTCTCGGCTCACCTGGGCCCGCAGTCGCTG
```

```
GCTTTGCCGTTGGCTTTGTTCTCCACTTGGCTCTCGGTAAGGCTCCGTCTCGGGCCTGG

TTGAACCGACTTCTTACTCTTTTACCTCGCTCGGTCGCTTTACCTCAGGACTTCTTTTT

GGAGGAGGACGTGAGGGCTCGAGCTTCTGAGCTCCTGCGTTCCCTTTCTATTAGTCGTT

CTGTGTCTAAGCTCCTGGCTTCTGTTGGTGACAAGTACATCACTCGTACCTCTGGCAGC

CTCTTCTGGGAGGTCGCAGCCACTGTGATCTCCTGGTTTAGGCGCCTGTTGGACTGGGT

CACCTCCTGCGTGAAGGACCGGATGCCCTCTGTTCCTGTGCCTATGTTGACCTGCCAGG

CCGCTTACACTGGACCTTGGGTTGGTACTGGTACCGTCACTGGCCGTTGCGGCTGTGGC

GCTGCCATCTCTGCTGACTTCGAGGAGGGTGTTCGCGTTCGCTGGCACACTACTTCATA

TTTCTGCCGTGGGTACTTTGCCCGCGGCATTCCTCTGAATACTCTTGGCACTACTTCAG

GTCCTCGCCCGGCCCCCAAGCTCGTGGGTCACCGGGCTATCCATCCCGTGGGCTTACT

GGCTACGTTGAGGTTTTGCGCGCGGAAACTGGTGAGGTAACAATCACTAGGACTACCGA

GCATGATCTCACTCGTGACCAACTTCTCCACGCCTTACGCCAGCCGCCCTACCAGGTGG

ATGGTGTGGTCTGTTCTCTCCGCTATTCGGCTTCACTCATTGCCATGATTTACGGTTCT

GGTGCCGTTGTTGATTACGAAGGTCGGGCCATTACCCTCCCTCACACCGTCCCCGGAGA

TGGCGTCAATCCCGAGTATATCGGGACGGTCGCCCTCGAAGGGGATGCTGTCCGGGAGG

CTATGGCTGAACCAGAGGTTTGGCATGACACCACTGACCGTTTTTCTGACAGTGTTGAG

CCGGAAGAGCTTGAGCGCTTGACTCTCGGCTCCGAGGTTGAGTTGCCTCCGTTGGATCC

GGAGGGACCAGGGGTCGTTCCGTCTGAGCGTACCTTCTTTGTGGCTTCCAATCCGCAAG

GTGAGGTCGCCATCGAGAGGGACGTTGAGACGCTTACTCCCCCTATTCCTCCTGTTCCC

CCGTTGGCTCCTTTGCCCACGAGGCCGGTGGTCTTGCCTCCACCTCCTTCTGATTCTGG

CCCTTTGGGTACATCCGACTACCCAGCTACCTACTCTGACACCGGCTCTATGCCGCCGT

TGGAGGGTGAGCTCCGTGGTTCGGGTGCATCCACTCCTATTTTCTGGCAGGAACCTACT

CGTTTCTCCCATGTGCCTACATCTATTAGCATTGAGTCTACTGACAGGTCTATCGCTCA

GGGGTTGCTCGACTCCGTCGGTTCTTCGGCTGAGGCATTGGCCGTTGCTACTGAAGTTG

TTAATCGCAGCTTTCTCACACCTGCTCTTTGCCATGAAGCGCTCCATGGTTCTGGCGCC

TTGGTGGCTTCACTCCCGCCGCCGGACCCCGAGGTTGCCTCGGTCGCTTCCACACCCGA

GCCTGACACTGTTCATGGCGCGGTTGCGGTGGCGGCCCAGACGGCGTTGGGGACTGTTG

CGGCGGCCTTGACGGCTGCCACTGGCAATAGTTCCGGGGAGGCTTCTCCTGTGCTCCCT

GAACCCCAGGTGCGGGTTGTGCACTTGACTGCTCCTTGTTTCAATCATGATGGGGATGT

TCTTTGTACTTCGGCTGACATCACCTTGGCCGGAGTTTTGGTGCATGCCGGGGGCGTT

TTAACCACCGGCACAGCTTCTGGGTCAATGGTGTTAGGCGCAGGGGCACCACTCGCGTG

GCGTCCCTGTGTGACACTGCTGTCTCAGTTACTGTTAGGTGCAATTCTCCCTCGGGCTC

TTCTTGCAGCCAAACATCACTTCCTCCTGCTGAACCTGCTGTGCGGAGCCCTAGCCCTA

GGGCCCCGCGCGGCGTGCACATCAGTTGGACTTGCTGCCAAAATCGTTCCTACCGTGGT

TTTTACTCAGGAAACTTTACCATTTCTGACATTTGTGATGGGTTTGCCATCTTTCCAGA

CTCCTCCCACCTCTTCTTCCATGGGAACCGGGTGTTGACACTCGAGACTCGTGTTGAGG

AACTGGAGGGAGAACAGATTGAGATTCAGTACACCTGCAGACATGAGACCGAACCCGTC

TCTCGCTGCGTGAGGTCGTACATTTGGTACGGTGTTCCGCTACGGGTCGGTGAGAGCCG

CCCTGTACCGGTCACCCGCCCAATTGGATCCTTCATGCGCGCGGACGCTACTCGTGCTT

ACGTCACGCAGATGTCTGAAGTTGGGAACCGTATTGAGAAAGTCACCATTGAGCAGACG

ATTGCCTTGGAGGATCAGTTCCTTATGGATCGCTACAACTTGGCCCTTGCCAGGGCTAA
```

-continued

```
GAATGGCGGTCCGTATCGGGGCTGGTCTTATGAAGAGGCTGTGGCCAAGGTTCGCCCTC

GGGCTGCCGCTGGCCATAACGTCAAGCTCTCTGTTGCCGATCTCAAAACGCCTGCGGGT

CGGAAAATCGTGGAGGACACCATCCAGTCTATTGCTGGTGAGCGTGATGAACATCCTTT

CATGCTTACAGCTAAGTCTGAGGTGTTTTTCCAAGATAAGAAGACTCGCAAGCCACCTC

GGCTGCTCTGTTACCCCTCATTGGAGTTTAGAGTGGCTGAGAAAATGATCCTAGGCGAC

CCTGGCTTGGTAGCCAAGGCCGTCCTGGGTGATGCATATGGTTTCCAGTACACCCCCCA

ACAACGGGTTAGAAAACTACTCTCTCTGGGATGAGAAGCAAATACCCATTGCTATCA

CGGTTGACGCCAAGTGCTTTGATTCCACCATCACGGCGTTTGATGTCGACCGAGAAGCT

GAAATCTATGCCATTGCCCATGAGAAACCAGATCTGGTTCGCGCTCTCCATCGGCACTA

TAAGGCAGGTCCTATGGTGAACCGTGAGGGCGTTGAGGTTGGTTACCGTAACTGCCGCC

CATCTGGCATTTACACCACTTCTGCTTCTAATTCCATTACTTGCTGGATCAAGGTGGGT

GCCGCCTGTCGTAAGATAGGCCTTAGGAATCCTTCCTTCCTCATCCACGGTGATGACTG

TGTCATTATCGCGGAGAGGGGAGACGAGGACCCTACACCTGCTTTGCGTGCAGCTTTGC

TGGAATATGGGTATGACTCAGATCCTGCACTCCACGCTTCGCTGGACGAGGCGGAGTCA

GCTTCCACTTTCTTGGCTGAGTGCACGGCGGGTTACGACCGCCGTAAGATTTATTTCCT

TTCCACTGACTTCCGGAAGGTACTTGCGAGGGCTACGTCTGAGTACGGAGACCCGGTCG

CTTCTGCGTGTGGTTACACCTTGCTCTATCCGTGGCACCCTTTGACTAGGTGGGTCCTA

ATGGCGCAGGTCATTGGACTCCCCTTTTTAAGGGGTGCCTCGGTGGACGAGGCAATCAC

GTGCGAGGTGGCTGGTAACCGTCTCACGTTTCCTCTCAAGCAGCTGCCATCCATCCTGG

TGGCCCTGCATGGCCCGGAGTGCTTGCGCGTCGTCTCTGACTCCAATAAGACCCTCAGG

GAGACAAACAATGCGCTTCAGGCCCTCAGAATGCGGGGCTTTCCTGGTACCGGAAGAG

GACTATTGCTCTCAGGCTTAAAATGATCAGAGCTGGTGGGCAGTGGGCGAAGTTGGCCA

AGGCTCTCATCTGGCCTCCTTCTGCCTACATCCCATCGTTGGAGGTTGACACCTTCGAC

GCAACCCAGCTTTTGGACATTATGAGCAGGCCCTATAACAACCTTGAGCTCCAGATTGG

CAAGCCGATTCGTCGGTCGCTGACTGGACTCTTTGTGTCTAGGATCTGTTCTTTTTTTG

GTTCTGACATTCCTGCTACCTTAGCCGAAAGGTATGCACTTGGTCTTGTTTTGGTCGGT

TGGGCTCTCGCCGGCTACTGGCTTCTGTTCTGGGTGTGAGCCCCTAGTTTACTAGCACC

CTTTACAGTTTTCCTACTAAACATGATTGTTTGTTAGTCCAAGGCAACAGGCTTCGGCC

GGGGGAGTAGCGCCCCCCCCTTTGTGAGCTCGTAACCCCCTTTTGGGGCTGTTCCTCCC

TGGGAAGAGGAGCAGTACATCCCCGGCTGGCAGCCGTTAATTGCTACGTGGTGGTTATA

GCCCGGCAAGGTTAACAGGGGAGTAGTGCCCCCCCCGCCCCAACTCGGGTAGCGCGTA

CGCTCGTCGGTCCTCCGACGTTAAAGAACCTGGCCT
```

Coding sequence of SEQ ID NO.: 1

SEQ ID NO.: 2

```
ATGGCGCCTTTCTTGTTGCTGGTTCTTTTGTGCGGGGCCGGTGCTATCCGCGCCCCCGC

CTCACACAAATGTTCCTTCAAAGGCCGGTTTTATCTGTCAAACTGCTGTGATCCAAAGG

ACATACTGCTCTGCACTTACGACTTCTGCGTTACCCGCGTTGGTTGTCATGTGTGCACA

GAAGTTTGTTGGAACGTCTCTCGTCCTGGCATTTCTGTTCGACCCGGTTCAGGTGATGT

GGAGCCCGACCTTAAGGGGTTCTTCTCGGTCGCTGCGGTGGGTGGCTATGCTGCCTCCC

TCATCGGCCTCGGAGAGCCTTTTTCTGTCGGCTTGCTTGGCCTCACCATCCTTTACCGG

GTTGATACTGGGGTTCCTGACGGGTTGCGTTGCGACAGACCTTGCAATGTGTCAGTTCC
```

-continued

```
CGTTTGGCCCTCGTCCCTCGAGGGGATGCGGGTCTTGTGGGAAGTTGTCTGGGGTTTGC

TGTACCGCATTCCGCACATGATTTGGGCAGCCTTTAACATCTTCGATGTGTGGTTGTTG

GGTCTAGTCATCCTCCTTACCCTGGAGGGTCGCTGGCACCTGGCGATCATGCTCGTCCT

TGCCGCTGGCTTGTCTACTTCTAGTGCTGAACTTGTTGGGGAGCCATGGGACTCATGCA

CCTGTAAGGGTGTTGTGGGTCTTAGGCACCTTAACGAGACTACTTCTCCATGTCTCTGT

GAAAATGGCCCTTGGTACTATGATGCTGGTACGCCAGGCCTCACCTCTTTCGAGAGGGG

GGGTGGCTACTGTCCTTCCCGATCGGTCCGCAGGTCCGGATGCTCGCTGTGGTGCCAGT

GGGGATCGTGGGTTACTATCTACCCTCCCTCCTGGCCTAACGGCCGGCATTCTTGGCTC

TGTAATTGGCGGTGTTGGTGCAATGGTCGCCGATGCTGGATTACCTGCCTCGTTGACGC

ACGTCGACATTGGTGTGGTTCCTGCGTCCGCGATTGTTGGGCTGAGACCGCTGATGATT

CTCTTACCTTCGGGAACTGTGGCACTGGCCCTCGCGTCACTGCTAACTTAACCGCTTTC

CCTTTGCACTATGGTCAGAAATCTACTGTTGCTTTGGCTACTAAAATGGTCTTGACTGC

TAAATTACAACCCTTGTGGAGGAATCTTAACACTACCATTATGTGCTCAGTTATTCGGA

CTTCTGTCCATTGCTTTAGTTGCATCGGCTTGCCGTCGCCTCCCGCGGGTTTGTGGGAG

CGTGTCCCGGGCGAACCCATTTCTGATTGTGAAGGCGTGCAGGTTTCCACTGGTAAGCG

GACTCCCACATGCCCAACCAAGCAGAGGTGGAATGCTACTGTGCACGTCTGCCCCGGTT

ACGCCTTCTACTCTCCCGCGTATGATGATGGCGAGCTTCATGTTGCTGGCTACTGGCAG

TGGCTTTTGGCCGGACGCACTATTCACTTTTGGTTTCTTGTAGATTTCCTGCTTGTTTA

CTTGTTCTTGATGCACCTCTCTGGTGCGCGCATCACCCCCTTTTTAGCCTTGGCTCTTT

GGATTCACTTGCGGGGGGGGTCTTTGGATCCCCCACTCCGATACCTGGCTGCAAAAAT

AAGAATGAAGCCATCCACAACTACACACACTGTGTCCAGGCTCTTGGTCACGCCATTAG

CGTGGTTGGTGAGGCGAGTGCGAATTATGCTGGTCACTGGCTGCTACAGGGCCCGTTTA

CCGGTCTCTCGTGGATAGTCAACGCCACGTCGTCCGCATTCAATATCACCTCCCATGCC

TTGACCACTGTCGGCTCTACACTGTCATCACTGGCTGAGGCTTGGATTCCCTTGGGCGG

GGCCTCACATCCCCTCGCTCCTTCCACAGGCAGTTTAGCGGCGGCGATCCTAGCGCCGT

GCGCCTCTTGTGCTCCTGCCGCTTGGTTTAGCGCAGCTCCCATGCTAGGCTGGGCGTTT

CGCTATCCCACTTGGCACGAGTCCATTATGGCTCTGCTTTTGGTCCTGATTTACATGAG

GTTCGCCGGGGTCGCTCGGCTTGCCGCTCTGGTTACTTGGAAGTTGACTCGCAACTTCG

GCGCTGTTGGTGTGCTCGTCCTCCTAGTGCTTGCGCGTAGGAAGACCAGTGCTTTGGGG

TACGAGATCTGTATTTCCCTTACGGGCGAGGCTGATTGGGACTGGTTGGATTTTTCCTC

CTGGCTCCTCTCGCTTCTGTTCGCTTGGGCAGTGCTTGCTCTCGCGTCCCTTACACCAG

CAATGAAGAAGCGTAAGCTCCGATGGTACTCTCGCTGGGCTTGGTGCTACTCTCGGTTC

ATCTCGTGGGTCGACCACACTCCATTCAACGGTGTAGATCCCCTTTCTCGGAAGGCTTC

CTACTACTGGCTGTTTGCGGGTCTGGTTTGGCCTAACGAGGTTGCCGTTGTGGTTGCCT

CGTACGTCTTGATTGCCGTCGTGGTTGACTTGACTGACATTTTACTAGAGACCCTCTTG

TTGTCAAATCCTGATCTGGGAAGGCTCGCGGTGTTGTGTGACACCATCGCGGGTCTCAG

GTCTCCCTGGTTCCTCCATTGGGTTCTGGAGCGCGCAGCTAGGCGTGGCATTTACCTCT

ATCACCACCAGGGGCATTTGTCCGCACGGCTCGCACAGTATCTCAGGGAGTTGGATGGT

GCCTTGGAGCCGGCGCGGGTTACGCCGCAGGACTGCGAGTTTGTGCGCGACGCTCAGCG

GATTCTTGAGTGTGGCCGCAATTATCGCGGGAAGGCGGTTGTTGCCCGCAACGGTGACA

CTGTCATCATTGGCGCCGTTCGCGGGGCCTGGGAGCTCCCCCCCGGGTTCGTGCTTACG
```

-continued

```
GCCCCCCTCATGCTTCGAAGCGTTGGCCGTGGAGTCTGGCAGACGCTAGTGACGAGCAT

GATGGGAAGGACAAGGAAGATCACACAGGCAATGTCCTTATCCTTGGGACCGCTGCCA

CCCGGTCAATGGGGACGTGCGTCGGGGGGGTGGTTTACACCACATTCCACTCCTCCAAC

GGTCGGACTTTGGCTGGGCCAACTGGGCCCCTAAATCCTCGGTGGTGGTCGCCCTCGGA

CGACACCGCCGTGTACCCAATGCCTGTAGGCTGCAGAAGTCTAGAGATTTGTGGATGTG

GAGCCCGGAGCGCATGGGTACTGCGCAAGGATGGTGCTCTAGTCCACGGTGAACTGTTT

CCTGGACGTGAGATTAGACTGGATGTCGCTGGTCGTGTTGCAGACTTTAAGGGCGCATC

AGGTTCACCCATACTCTGTGACCAGGGTCATGCCATGGGTATGTTGACCGCGGTGTCGC

ATCGGGGCCGGAAGTACACTCGGCCCTCTTTGTCAAGCCGTGGGACAGCGTTCCCAGG

GATGCCCAAACGGTTACGGACGTGGGTGCACCTCCTGCGGTACCTGGCAAAGGCAACTA

CGAGGAGCGATCCTTGTTCTTGCCCACTGGCACTGGCAAGTCCACCCTTGTCCCTGCCA

ATTATGCCAAGTCAGGCCACAAGACCTTGGTTCTGAACCCGTCTGTTGCCACTGTTGCC

GCCATGGGTCCTTACATGAAGGACAAAATGGGCATTACACCGTCCATCTTTGCTGGCCA

TGGGCCCACCGCTATCTCGCGCAACACTGGGTCTAACCTGGTGTACGCGACTTACGGTC

GTTTCTTGGCCAAGCATAAGCAGTTGCTGGACGGTGTCTCTGTTATTCTTTGTGATGAG

TGCCACAGCTCAGACCCGACAGTATTGTTGGGTATTGGGCTGGTGCGCTCTGAAGCGAA

GAAGGCCGGAGTGAACTTAGTTCTCTTCGGTACAGCTACACCACCTGGCTATGCTACAG

TCCCTCATAAGAACATCACGGAGGCACCGGTTGGGACGGATGGTGACATTCCATTCTAT

GGTTTCTACTTGAAGTCCACTAACTACACCACTGGCAGACATCTGATCTTTGTCCACTC

TAAGAGTGAGGCGGAGCGCGTCGCCTCCGCTCTTACTGCTAAGGGCGTCAAAGCTATGT

TCCACTACTCAGGTCGGGATCCAACCGCAATCCCCACCACTGGTAGTTTGACCGTAGTA

GCCACCGATGCCCTTAACACAGGATACACAGGTGACTTTGATACGGTGACGGACTGCAA

TGTGGCTGTGCAGGAAGAAGTTACCGTTGATCTTGAACCTACCTTCACCATTTCTCTTC

GCACTCGGCCAGCTACGGCTGATCTGCGTGCCCAGAGGAGGGGGCGTTGCGGTCGCGGC

AGGCCTGGCCTGTACCGTTACTGTATAGCCTCTTCCCCGCCTTGTGGCACGGTCCCATC

CGGGGCCGTTTGGGCCGCTTTTGACGCTGCGCTGACTTGGTACGATATTCAGCCCGCCG

CCGCTGCGCGGTTGATTGGACTTTTTGCAGAGTGCCCTTACACCGGGCACATTGGCGTA

AACTTGCAGGACCCCCAGCGGGTCTATGAGGTCCTCGCTCCGTTTGCGCTGACGCCAGA

CGTAGTGAGAGCAAGGAACGCCGGGGTCAGCTGGCCCCTCCTCGTTGGAGTCCAACGGT

CAGAGTGCAAGCGCTGCGCCTCAGGTCCTCCTTCCAACGCCCCCACTGGCAGGGTTTG

GTCGGCGATTGTGCCGTTCCGCTGCTTTACGCCTTGGAGACTCAGAGGCCCGAGAGGGT

AATCCGATCTCCATTGGTCGATCAATTGGCTGCGGCCTTGGGCGACTCTGTTACAGAGA

CGTCCTCTGGCCCCATCCTTTTGGCCGGCTTGGCGTTGGCTGCGGCCGCTGCTATTGCT

GACTACACCGGGACTTTGGTGGTCGTTGGGACCTTTGACGTGCGCCCTGGGGGGCTCC

GCGGCCTCCCCAATCGCGCGATCTGCCCGGCGGATTATCATCAGGACAGCCACAGAGTG

ATGGCGAGGGGCCTCCCCCTCCCCGTCGCACTGACCAGCTGACAGACTCCCAAACTTTG

GACGCACTCCAGGATGTGATGACCCAGACATCGTGGGAGTGTCTGGATTATTGCTACCG

GGTAGCGACCGGTACCCTGGCTCCTAGAACCGCCGACGCGCTGGAAAGCGGGGCGCGTT

GGCTTCGGGAGGCGTGCTGTGGGACTAACCCTCCCACTAGTCCATTCCCAGGTGGGTGG

GGGGTCACCCAACCCCTACCTCTCGGACACCTTGCTGTGAAGGCTTGGCAAACCTTGCT
```

-continued

```
CAACAACTTGGGTACTGCTATTTCCCTGGTCACCGCGGCCTGGGCCGCTGGTAGTTCTC
CTCCGCTTGCTTGTATCGCCTCAGCGTTGCTTGGGTTGCAAAGCGCGTTGCCGCTCGAC
GTGCGCCTCCCGGCCGCTCTCCTTGCTGGTGCCGGTGGCACTCTCTTCGGAGATGCCGC
CACTGGCTTGGGGATGGCCGCGTCGTTCATGTTGGGTGGCACGGTTGGAACCGCTGGCC
CTTTCATGTTCCTACTTGAAGTCTTGGGGGGGTATGAGTCGACGGTGGTCGGCGCCTCC
CTTGCATTTGACCTTTTTTCTGGAAACGCTTCTATGTCAGACTTGGTTTACCTAATCCC
TGCTCTCGGCTCACCTGGGCCCGCAGTCGCTGGCTTTGCCGTTGGCTTTGTTCTCCACT
TGGCTCTCGGTAAGGCTCCGTCTCGGGCCTGGTTGAACCGACTTCTTACTCTTTTACCT
CGCTCGGTCGCTTTACCTCAGGACTTCTTTTTGGAGGAGGACGTGAGGGCTCGAGCTTC
TGAGCTCCTGCGTTCCCTTTCTATTAGTCGTTCTGTGTCTAAGCTCCTGGCTTCTGTTG
GTGACAAGTACATCACTCGTACCTCTGGCAGCCTCTTCTGGGAGGTCGCAGCCACTGTG
ATCTCCTGGTTTAGGCGCCTGTTGGACTGGGTCACCTCCTGCGTGAAGGACCGGATGCC
CTCTGTTCCTGTGCCTATGTTGACCTGCCAGGCCGCTTACACTGGACCTTGGGTTGGTA
CTGGTACCGTCACTGGCCGTTGCGGCTGTGGCGCTGCCATCTCTGCTGACTTCGAGGAG
GGTGTTCGCGTTCGCTGGCACACTACTTCATATTTCTGCCGTGGGTACTTTGCCCGCGG
CATTCCTCTGAATACTCTTGGCACTACTTCAGGTCCTCGCCCGGCCCCAAGCTCGTGG
GTCACCGGGCTATCCATCCCGTGGGGCTTACTGGCTACGTTGAGGTTTTGCGCGCGGAA
ACTGGTGAGGTAACAATCACTAGGACTACCGAGCATGATCTCACTCGTGACCAACTTCT
CCACGCCTTACGCCAGCCGCCCTACCAGGTGGATGGTGTGGTCTGTTCTCTCCGCTATT
CGGCTTCACTCATTGCCATGATTTACGGTTCTGGTGCCGTTGTTGATTACGAAGGTCGG
GCCATTACCCTCCCTCACACCGTCCCCGGAGATGGCGTCAATCCCGAGTATATCGGGAC
GGTCGCCCTCGAAGGGGATGCTGTCCGGGAGGCTATGGCTGAACCAGAGGTTTGGCATG
ACACCACTGACCGTTTTTCTGACAGTGTTGAGCCGGAAGAGCTTGAGCGCTTGACTCTC
GGCTCCGAGGTTGAGTTGCCTCCGTTGGATCCGGAGGGACCAGGGGTCGTTCCGTCTGA
GCGTACCTTCTTTGTGGCTTCCAATCCGCAAGGTGAGGTCGCCATCGAGAGGGACGTTG
AGACGCTTACTCCCCCTATTCCTCCTGTTCCCCCGTTGGCTCCTTTGCCCACGAGGCCG
GTGGTCTTGCCTCCACCTCCTTCTGATTCTGGCCCTTTGGGTACATCCGACTACCCAGC
TACCTACTCTGACACCGGCTCTATGCCGCCGTTGGAGGGTGAGCTCCGTGGTTCGGGTG
CATCCACTCCTATTTTCTGGCAGGAACCTACTCGTTTCTCCCATGTGCCTACATCTATT
AGCATTGAGTCTACTGACAGGTCTATCGCTCAGGGGTTGCTCGACTCCGTCGGTTCTTC
GGCTGAGGCATTGGCCGTTGCTACTGAAGTTGTTAATCGCAGCTTTCTCACACCTGCTC
TTTGCCATGAAGCGCTCCATGGTTCTGGCGCCTTGGTGGCTTCACTCCCGCCGCCGGAC
CCCGAGGTTGCCTCGGTCGCTTCCACACCCGAGCCTGACACTGTTCATGGCGCGGTTGC
GGTGGCGGCCCAGACGGCGTTGGGGACTGTTGCGGCGGCCTTGACGGCTGCCACTGGCA
ATAGTTCCGGGGAGGCTTCTCCTGTGCTCCCTGAACCCCAGGTGCGGGTTGTGCACTTG
ACTGCTCCTTGTTTCAATCATGATGGGGATGTTCTTTGTACTTCGGCTGACATCACCTT
GGCCGGAGTTTTGGTGCATGCCGGGGGCGTTTTAACCACCGGCACAGCTTCTGGGTCA
ATGGTGTTAGGCGCAGGGGCACCACTCGCGTGGCGTCCCTGTGTGACACTGCTGTCTCA
GTTACTGTTAGGTGCAATTCTCCCTCGGGCTCTTCTTGCAGCCAAACATCACTTCCTCC
TGCTGAACCTGCTGTGCGGAGCCCTAGCCCTAGGGCCCCGCGCGGCGTGCACATCAGTT
GGACTTGCTGCCAAAATCGTTCCTACCGTGGTTTTTACTCAGGAAACTTTACCATTTCT
```

-continued

```
GACATTTGTGATGGGTTTGCCATCTTTCCAGACTCCTCCCACCTCTTCTTCCATGGGAA

CCGGGTGTTGACACTCGAGACTCGTGTTGAGGAACTGGAGGGAGAACAGATTGAGATTC

AGTACACCTGCAGACATGAGACCGAACCCGTCTCTCGCTGCGTGAGGTCGTACATTTGG

TACGGTGTTCCGCTACGGGTCGGTGAGAGCCGCCCTGTACCGGTCACCCGCCCAATTGG

ATCCTTCATGCGCGCGGACGCTACTCGTGCTTACGTCACGCAGATGTCTGAAGTTGGGA

ACCGTATTGAGAAAGTCACCATTGAGCAGACGATTGCCTTGGAGGATCAGTTCCTTATG

GATCGCTACAACTTGGCCCTTGCCAGGGCTAAGAATGGCGGTCCGTATCGGGGCTGGTC

TTATGAAGAGGCTGTGGCCAAGGTTCGCCCTCGGGCTGCCGCTGGCCATAACGTCAAGC

TCTCTGTTGCCGATCTCAAAACGCCTGCGGGTCGGAAAATCGTGGAGGACACCATCCAG

TCTATTGCTGGTGAGCGTGATGAACATCCTTTCATGCTTACAGCTAAGTCTGAGGTGTT

TTTCCAAGATAAGAAGACTCGCAAGCCACCTCGGCTGCTCTGTTACCCCTCATTGGAGT

TTAGAGTGGCTGAGAAAATGATCCTAGGCGACCCTGGCTTGGTAGCCAAGGCCGTCCTG

GGTGATGCATATGGTTTCCAGTACACCCCCCAACAACGGGTTAGAAAACTACTCTCTCT

CTGGGATGAGAAGCAAATACCCATTGCTATCACGGTTGACGCCAAGTGCTTTGATTCCA

CCATCACGGCGTTTGATGTCGACCGAGAAGCTGAAATCTATGCCATTGCCCATGAGAAA

CCAGATCTGGTTCGCGCTCTCCATCGGCACTATAAGGCAGGTCCTATGGTGAACCGTGA

GGGCGTTGAGGTTGGTTACCGTAACTGCCGCCCATCTGGCATTTACACCACTTCTGCTT

CTAATTCCATTACTTGCTGGATCAAGGTGGGTGCCGCCTGTCGTAAGATAGGCCTTAGG

AATCCTTCCTTCCTCATCCACGGTGATGACTGTGTCATTATCGCGGAGAGGGGAGACGA

GGACCCTACACCTGCTTTGCGTGCAGCTTTGCTGGAATATGGGTATGACTCAGATCCTG

CACTCCACGCTTCGCTGGACGAGGCGGAGTCAGCTTCCACTTTCTTGGCTGAGTGCACG

GCGGGTTACGACCGCCGTAAGATTTATTTCCTTTCCACTGACTTCCGGAAGGTACTTGC

GAGGGCTACGTCTGAGTACGGAGACCCGGTCGCTTCTGCGTGTGGTTACACCTTGCTCT

ATCCGTGGCACCCTTTGACTAGGTGGGTCCTAATGGCGCAGGTCATTGGACTCCCCTTT

TTAAGGGGTGCCTCGGTGGACGAGGCAATCACGTGCGAGGTGGCTGGTAACCGTCTCAC

GTTTCCTCTCAAGCAGCTGCCATCCATCCTGGTGGCCCTGCATGGCCCGGAGTGCTTGC

GCGTCGTCTCTGACTCCAATAAGACCCTCAGGGAGACAAACAATGCGCTTCAGGCCCTC

AGAATGCGGGGCTTTCCTGGTACCGGAAGAGGACTATTGCTCTCAGGCTTAAAATGAT

CAGAGCTGGTGGGCAGTGGGCGAAGTTGGCCAAGGCTCTCATCTGGCCTCCTTCTGCCT

ACATCCCATCGTTGGAGGTTGACACCTTCGACGCAACCCAGCTTTTGGACATTATGAGC

AGGCCCTATAACAACCTTGAGCTCCAGATTGGCAAGCCGATTCGTCGGTCGCTGACTGG

ACTCTTTGTGTCTAGGATCTGTTCTTTTTTTGGTTCTGACATTCCTGCTACCTTAGCCG

AAAGGTATGCACTTGGTCTTGTTTTGGTCGGTTGGGCTCTCGCCGGCTACTGGCTTCTG

TTCTGGGTG
```

TDAV polyprotein 120618
encoded by SEQ ID NO.: 2

SEQ ID NO.: 3

MAPFLLLVLLCGAGAIRAPASHKCSFKGRFYLSNCCDPKDILLCTYDFCVTRVGCHVCT

EVCWNVSRPGISVRPGSGDVEPDLKGFFSVAAVGGYAASLIGLGEPFSVGLLGLTILYR

VDTGVPDGLRCDRPCNVSVPVWPSSLEGMRVLWEVVWGLLYRIPHMIWAAFNIFDVWLL

GLVILLTLEGRWHLAIMLVLAAGLSTSSAELVGEPWDSCTCKGVVGLRHLNETTSPCLC

ENGPWYYDAGTPGLTSFERGGGYCPSRSVRRSGCSLWCQWGSWVTIYPPSWPNGRHSWL

-continued

```
CNWRCWCNGRRCWITCLVDARRHWCGSCVRDCWAETADDSLTFGNCGTGPRVTANLTAF
PLHYGQKSTVALATKMVLTAKLQPLWRNLNTTIMCSVIRTSVHCFSCIGLPSPPAGLWE
RVPGEPISDCEGVQVSTGKRTPTCPTKQRWNATVHVCPGYAFYSPAYDDGELHVAGYWQ
WLLAGRTIHFWFLVDFLLVYLFLMHLSGARITPFLALALWIHLRGGVFGSPTPIPGCKN
KNEAIHNYTHCVQALGHAISVVGEASANYAGHWLLQGPFTGLSWIVNATSSAFNITSHA
LTTVGSTLSSLAEAWIPLGGASHPLAPSTGSLAAAILAPCASCAPAAWFSAAPMLGWAF
RYPTWHESIMALLLVLIYMRFAGVARLAALVTWKLTRNFGAVGVLVLLVARRKTSALG
YEICISLTGEADWDWLDFSSWLLSLLFAWAVLALASLTPAMKKRKLRWYSRWAWCYSRF
ISWVDHTPFNGVDPLSRKASYYWLFAGLVWPNEVAVVVASYVLIAVVVDLTDILLETLL
LSNPDLGRLAVLCDTIAGLRSPWFLHWVLERAARRGIYLYHHQGHLSARLAQYLRELDG
ALEPARVTPQDCEFVRDAQRILECGRNYRGKAVVARNGDTVIIGAVRGAWELPPGFVLT
APLMLRSVGRGVWQTLVTSMMGKDKEDHTGNVLILGTAATRSMGTCVGGVVYTTFHSSN
GRTLAGPTGPLNPRWWSPSDDTAVYPMPVGCRSLEICGCGARSAWVLRKDGALVHGELF
PGREIRLDVAGRVADFKGASGSPILCDQGHAMGMLTAVSHRGPEVHSALFVKPWDSVPR
DAQTVTDVGAPPAVPGKGNYEERSLFLPTGTGKSTLVPANYAKSGHKTLVLNPSVATVA
AMGPYMKDKMGITPSIFAGHGPTAISRNTGSNLVYATYGRFLAKHKQLLDGVSVILCDE
CHSSDPTVLLGIGLVRSEAKKAGVNLVLFGTATPPGYATVPHKNITEAPVGTDGDIPFY
GFYLKSTNYTTGRHLIFVHSKSEAERVASALTAKGVKAMFHYSGRDPTAIPTTGSLTVV
ATDALNTGYTGDFDTVTDCNVAVQEEVTVDLEPTFTISLRTRPATADLRAQRRGRCGRG
RPGLYRYCIASSPPCGTVPSGAVWAAFDAALTWYDIQPAAAARLIGLFAECPYTGHIGV
NLQDPQRVYEVLAPFALTPDVVRARNAGVSWPLLVGVQRSECKRCASGPPSNAPHWQGL
VGDCAVPLLYALETQRPERVIRSPLVDQLAAALGDSVTETSSGPILLAGLALAAAAAIA
DYTGTLVVVGTFDVRPGGAPRPPQSRDLPGGLSSGQPQSDGEGPPPPRRTDQLTDSQTL
DALQDVMTQTSWECLDYCYRVATGTLAPRTADALESGARWLREACCGTNPPTSPFPGGW
GVTQPLPLGHLAVKAWQTLLNNLGTAISLVTAAWAAGSSPPLACIASALLGLQSALPLD
VRLPAALLAGAGGTLFGDAATGLGMAASFMLGGTVGTAGPFMFLLEVLGGYESTVVGAS
LAFDLFSGNASMSDLVYLIPALGSPGPAVAGFAVGFVLHLALGKAPSRAWLNRLLTLLP
RSVALPQDFFLEEDVRARASELLRSLSISRSVSKLLASVGDKYITRTSGSLFWEVAATV
ISWFRRLLDWVTSCVKDRMPSVPVPMLTCQAAYTGPWVGTGTVTGRCGCGAAISADFEE
GVRVRWHTTSYFCRGYFARGIPLNTLGTTSGPRPAPKLVGHRAIHPVGLTGYVEVLRAE
TGEVTITRTTEHDLTRDQLLHALRQPPYQVDGVVCSLRYSASLIAMIYGSGAVVDYEGR
AITLPHTVPGDGVNPEYIGTVALEGDAVREAMAEPEVWHDTTDRFSDSVEPEELERLTL
GSEVELPPLDPEGPGVVPSERTFFVASNPQGEVAIERDVETLTPPIPPVPPLAPLPTRP
VVLPPPPSDSGPLGTSDYPATYSDTGSMPPLEGELRGSGASTPIFWQEPTRFSHVPTSI
SIESTDRSIAQGLLDSVGSSAEALAVATEVVNRSFLTPALCHEALHGSGALVASLPPPD
PEVASVASTPEPDTVHGAVAVAAQTALGTVAAALTAATGNSSGEASPVLPEPQVRVVHL
TAPCFNHDGDVLCTSADITLAGVLVHAGGRFNHRHSFWVNGVRRRGTTRVASLCDTAVS
VTVRCNSPSGSSCSQTSLPPAEPAVRSPSPRAPRGVHISWTCCQNRSYRGFYSGNFTIS
DICDGFAIFPDSSHLFFHGNRVLTLETRVEELEGEQIEIQYTCRHETEPVSRCVRSYIW
YGVPLRVGESRPVPVTRPIGSFMRADATRAYVTQMSEVGNRIEKVTIEQTIALEDQFLM
```

-continued

DRYNLALARAKNGGPYRGWSYEEAVAKVRPRAAAGHNVKLSVADLKTPAGRKIVEDTIQ

SIAGERDEHPFMLTAKSEVFFQDKKTRKPPRLLCYPSLEFRVAEKMILGDPGLVAKAVL

GDAYGFQYTPQQRVRKLLSLWDEKQIPIAITVDAKCFDSTITAFDVDREAEIYAIAHEK

PDLVRALHRHYKAGPMVNREGVEVGYRNCRPSGIYTTSASNSITCWIKVGAACRKIGLR

NPSFLIHGDDCVIIAERGDEDPTPALRAALLEYGYDSDPALHASLDEAESASTFLAECT

AGYDRRKIYFLSTDFRKVLARATSEYGDPVASACGYTLLYPWHPLTRWVLMAQVIGLPF

LRGASVDEAITCEVAGNRLTFPLKQLPSILVALHGPECLRVVSDSNKTLRETNNALQAL

RMRGLSWYRKRTIALRLKMIRAGGQWAKLAKALIWPPSAYIPSLEVDTFDATQLLDIMS

RPYNNLELQIGKPIRRSLTGLFVSRICSFFGSDIPATLAERYALGLVLVGWALAGYWLL

FWV

SEQ ID NO.: 4
AGGGTTCTTCGGGTAAATCC

SEQ ID NO.: 5
CCCTCGGACTGAATTATAGGC

SEQ ID NO.: 6
GCTTTCCCTTTGCACTATGG

SEQ ID NO.: 7
CAAGCCGATGCAACTAAAGC

SEQ ID NO.: 8
GGCTCTTTGGATTCACTTGC

SEQ ID NO.: 9
CCAGTGACCAGCATAATTCG

SEQ ID NO.: 10
ATGCCATGGGTATGTTGACC

SEQ ID NO.: 11
CTCCTCGTAGTTGCCTTTGC

SEQ ID NO.: 12
TGGGAGTGTCTGGATTATTGC

SEQ ID NO.: 13
CAAGGTGTCCGAGAGGTAGG

SEQ ID NO.: 14
TGGTACTGGTACCGTCACTGG

SEQ ID NO.: 15
GCGAGGACCTGAAGTAGTGC

SEQ ID NO.: 16
CTCCTGTGCTCCCTGAACC

SEQ ID NO.: 17
AACACCATTGACCCAGAAGC

SEQ ID NO.: 18
CTTCTGCCTACATCCCATCG

SEQ ID NO.: 19
TGCATACCTTTCGGCTAAGG

SEQ ID NO.: 20
ATGCGGCGGCGTTATTCC

SEQ ID NO.: 21
GCTATCAATCTGTCAATCCTGTCC

SEQ ID NO.: 22
CGGGTAAACGGCGGGAGTAAC

SEQ ID NO.: 23
TAGGTAGGGACAGTGGGAATCTCG

```
                                                      SEQ ID NO.: 24
CACCACACCTTCTACAAC

SEQ ID NO.: 25
ATCTGGGTCATCTTCTCG

SEQ ID NO.: 26
GCCATCACCATCTTCCAG

SEQ ID NO.: 27
GACTCCACAACATATTCAGC

SEQ ID NO.: 28
AGGGTTCTTCGGGTAAATCCCGGCGCGGTGTTTTGGGTTCAGGGCAGTAGGGGCAGACG

GGCCAGCAGTCGCTGGTTCCTGGTACCACCACCCTATCCGGACGACCTCCCTCACGAAA

GGTCGCCACGGTCTGTGGCTCGACGACGCCTATAATTCAGTCCGAGGG

SEQ ID NO.: 29
GCTTTCCCTTTGCACTATGGTCAGAAATCTACTGTTGCTTTGGCTACTAAAATGGTCTT

GACTGCTAAATTACAACCCTTGTGGAGGAATCTTAACACTACCATTATGTGCTCAGTTA

TTCGGACTTCTGTCCATTGCTTTAGTTGCATCGGCTTG

SEQ ID NO.: 30
GGCTCTTTGGATTCACTTGCGGGGGGGGTCTTTGGATCCCCACTCCGATACCTGGCT

GCAAAAATAAGAATGAAGCCATCCACAACTACACACACTGTGTCCAGGCTCTTGGTCAC

GCCATTAGCGTGGTTGGTGAGGCGAGTGCGAATTATGCTGGTCACTGG

SEQ ID NO.: 31
ATGCCATGGGTATGTTGACCGCGGTGTCGCATCGGGGGCCGGAAGTACACTCGGCCCTC

TTTGTCAAGCCGTGGGACAGCGTTCCCAGGGATGCCCAAACGGTTACGGACGTGGGTGC

ACCTCCTGCGGTACCTGGCAAAGGCAACTACGAGGAG

SEQ ID NO.: 32
TGGGAGTGTCTGGATTATTGCTACCGGGTAGCGACCGGTACCCTGGCTCCTAGAACCGC

CGACGCGCTGGAAAGCGGGGCGCGTTGGCTTCGGGAGGCGTGCTGTGGGACTAACCCTC

CCACTAGTCCATTCCCAGGTGGGTGGGGGTCACCCAACCCCTACCTCTCGGACACCTT

G

SEQ ID NO.: 33
TGGTACTGGTACCGTCACTGGCCGTTGCGGCTGTGGCGCTGCCATCTCTGCTGACTTCG

AGGAGGGTGTTCGCGTTCGCTGGCACACTACTTCATATTTCTGCCGTGGGTACTTTGCC

CGCGGCATTCCTCTGAATACTCTTGGCACTACTTCAGGTCCTCGC

SEQ ID NO.: 34
CTCCTGTGCTCCCTGAACCCCAGGTGCGGGTTGTGCACTTGACTGCTCCTTGTTTCAAT

CATGATGGGGATGTTCTTTGTACTTCGGCTGACATCACCTTGGCCGGAGTTTTGGTGCA

TGCCGGGGGCGTTTTAACCACCGGCACAGCTTCTGGGTCAATGGTGTT

SEQ ID NO.: 35
CTTCTGCCTACATCCCATCGTTGGAGGTTGACACCTTCGACGCAACCCAGCTTTTGGAC

ATTATGAGCAGGCCCTATAACAACCTTGAGCTCCAGATTGGCAAGCCGATTCGTCGGTC

GCTGACTGGACTCTTTGTGTCTAGGATCTGTTCTTTTTTGGTTCTGACATTCCTGCTA

CCTTAGCCGAAAGGTATGCA

SEQ ID NO.: 36
CGTAAGGGCGCGTAGTGG

SEQ ID NO.: 37
CCGAAGCATCAAGGAACC

SEQ ID NO.: 38
ACACATTGCAAGGTCTGTCG
```

-continued

| | |
|---|---|
| ACACATTGCAAGGTCTGTCG | SEQ ID NO.: 39 |
| AACACCGCCAATTACAGAGC | SEQ ID NO.: 40 |
| AACCGAGAGTAGCACCAAGC | SEQ ID NO.: 41 |
| CAAATCCTGATCTGGGAAGG | SEQ ID NO.: 42 |
| CCCAAGGATAAGGACATTGC | SEQ ID NO.: 43 |
| TTTGTGATGAGTGCCACAGC | SEQ ID NO.: 44 |
| GCGAAGAGAAATGGTGAAGG | SEQ ID NO.: 45 |
| GTTCTGAACCCGTCTGTTGC | SEQ ID NO.: 46 |
| CAGCAACTGCTTATGCTTGG | SEQ ID NO.: 47 |
| ACCCAAGTTGTTGAGCAAGG | SEQ ID NO.: 48 |
| TACACTGGACCTTGGGTTGG | SEQ ID NO.: 49 |
| CACCAGAACCGTAAATCATGG | SEQ ID NO.: 50 |
| GAGCAGTCAAGTGCACAACC | SEQ ID NO.: 51 |
| TTGCCATCTTTCCAGACTCC | SEQ ID NO.: 52 |
| ATAAGACCAGCCCCGATACG | SEQ ID NO.: 53 |
| GTCAACCGTGATAGCAATGG | SEQ ID NO.: 54 |
| ACTCCCCCTGTTAACCTTGC | SEQ ID NO.: 55 |
| GCTCTTCCGATCTNNNNNN | SEQ ID NO.: 56 |
| GCTCTTCCGATCT | SEQ ID NO.: 57 |
| AATGATACGGCGACCACCGAGATCTACACTCTTTCCCTACACGACGCTCTTCCGATCT | SEQ ID NO.: 58 |
| CAAGCAGAAGACGGCATACGAGATNNNNNNNNGTGACTGGAGTTCAGACGTGTGCTCTTCCGATCT | SEQ ID NO.: 59 |
| AATGATACGGCGACCACC | SEQ ID NO.: 60 |
| CAAGCAGAAGACGGCATAC | SEQ ID NO.: 61 |
| AATGATACGGCGACCACCGAGAT | SEQ ID NO.: 62 |
| CAAGCAGAAGACGGCATACGA | SEQ ID NO.: 63 |

What is claimed is:

1. A primer pair selected from the group consisting of SEQ ID NOS.: 4 and 5; SEQ ID NOS.: 6 and 7; SEQ ID NOS.: 8 and 9; SEQ ID NOS.: 10 and 11; SEQ ID NOS.: 12 and 13; SEQ ID NOS.: 14 and 15; SEQ ID NOS.: 16 and 17; and SEQ ID NOS.: 18 and 19;
   wherein at least one primer of the pair comprises a detectable label.

2. A method for detecting a virus in a sample, comprising amplifying from the sample a nucleic acid using the primer pair of claim 1.

3. The method of claim 2 further comprising detecting the amplified nucleic acid.

4. A kit for the detection of nucleic acid of a virus in a sample, the kit comprising the primer pair of claim 1; and one or more amplification reagents.

5. The kit of claim 4 wherein the primer pair is fixably attached to a solid support.

6. The kit of claim 4 further comprising a labeled oligonucleotide probe for detecting the amplified nucleic acid.

7. A solid support comprising fixably bound thereto at least one primer of the primer pair of claim 1.

8. A method for detecting Theiler's disease-associated virus (TDAV) in a sample, comprising amplifying from the sample a nucleic acid using a primer pair selected from the group consisting of SEQ ID NOS.: 4 and 5; SEQ ID NOS.: 6 and 7; SEQ ID NOS.: 8 and 9; SEQ ID NOS.: 10 and 11; SEQ ID NOS.: 12 and 13; SEQ ID NOS.: 14 and 15; SEQ ID NOS.: 16 and 17; and SEQ ID NOS.: 18 and 19.

* * * * *

SEQUENCE LISTING

<160> NUMBER OF SEQ ID NOS: 63

<210> SEQ ID NO 1
<211> LENGTH: 10479
<212> TYPE: DNA
<213> ORGANISM: Theiler's disease-associated virus

<400> SEQUENCE: 1

```
tgataccgtg tcccggtacg acctcgcgcg tccccaagct cgccctgagg ggggagcgta     60
agggcgcgta gtggggtagc cccccaaacc gagccaccct agtgagtgac tttagaatgg    120
ttagggagac taccgccttc gctgtttggg gacctaatga tccgcgtgcc agggttcttc    180
gggtaaatcc cggcgcggtg ttttgggttc agggcagtag gggcagacgg gccagcagtc    240
gctggttcct ggtaccacca ccctatccgg acgacctccc tcacgaaagg tcgccacggt    300
ctgtggctcg acgacgccta taattcagtc cgaggggcgc agccctcgtt aaacttaggc    360
aaggttcctc gccattgatt tggccagggg tttaagtgaa cgccgccctt ttaatgttta    420
atagggttct ttcccggcgg gttgacaaac acttccctgg gctcttcgtt ggcctcggtt    480
ccttgatgct tcggcaccca tgagcgcaca ggggggggac cctgcgacag tccgccaaga    540
ggaaaatcct tcgggtgacc tcgtgcgcaa cccaatccct tcttcttcca catggcgtgt    600
ctgtggtgca tgctgtgatg gcgcctttct tgttgctggt tcttttgtgc ggggccggtg    660
ctatccgcgc ccccgcctca cacaaatgtt ccttcaaagg ccggttttat ctgtcaaact    720
gctgtgatcc aaaggacata ctgctctgca cttacgactt ctgcgttacc cgcgttggtt    780
gtcatgtgtg cacagaagtt tgttggaacg tctctcgtcc tggcatttct gttcgacccg    840
gttcaggtga tgtggagccc gaccttaagg ggttcttctc ggtcgctgcg gtgggtggct    900
atgctgcctc cctcatcggc ctcggagagc ctttttctgt cggcttgctt ggcctcacca    960
tcctttaccg ggttgatact ggggttcctg acgggttgcg ttgcgacaga ccttgcaatg   1020
tgtcagttcc cgtttggccc tcgtccctcg aggggatgcg ggtcttgtgg gaagttgtct   1080
ggggtttgct gtaccgcatt ccgcacatga tttgggcagc ctttaacatc ttcgatgtgt   1140
ggttgttggg tctagtcatc ctccttaccc tggagggtcg ctggcacctg gcgatcatgc   1200
tcgtccttgc cgctggcttg tctacttcta gtgctgaact tgttggggag ccatgggact   1260
catgcacctg taagggtgtt gtgggtctta ggcaccttaa cgagactact tctccatgtc   1320
tctgtgaaaa tggcccttgg tactatgatg ctggtacgcc aggcctcacc tctttcgaga   1380
gggggggtgg ctactgtcct tcccgatcgg tccgcaggtc cggatgctcg ctgtggtgcc   1440
agtggggatc gtgggttact atctaccctc cctcctggcc taacggccgg cattcttggc   1500
tctgtaattg gcggtgttgg tgcaatggtc gccgatgctg gattacctgc ctcgttgacg   1560
cacgtcgaca ttggtgtggt tcctgcgtcc gcgattgttg ggctgagacc gctgatgatt   1620
ctcttacctt cgggaactgt ggcactggcc ctcgcgtcac tgctaactta accgctttcc   1680
ctttgcacta tggtcagaaa tctactgttg ctttggctac taaaatggtc ttgactgcta   1740
aattacaacc cttgtggagg aatcttaaca ctaccattat gtgctcagtt attcggactt   1800
ctgtccattg ctttagttgc atcggcttgc cgtcgcctcc cgcgggtttg tgggagcgtg   1860
tcccgggcga acccatttct gattgtgaag gcgtgcaggt ttccactggt aagcggactc   1920
ccacatgccc aaccaagcag aggtggaatg ctactgtgca cgtctgcccc ggttacgcct   1980
tctactctcc cgcgtatgat gatggcgagc ttcatgttgc tggctactgg cagtggcttt   2040
tggccggacg cactattcac ttttggtttc ttgtagattt cctgcttgtt tacttgttct   2100
```

```
tgatgcacct ctctggtgcg cgcatcaccc ccttttttagc cttggctctt tggattcact    2160
tgcggggggg ggtctttgga tcccccactc cgatacctgg ctgcaaaaat aagaatgaag    2220
ccatccacaa ctacacacac tgtgtccagg ctcttggtca cgccattagc gtggttggtg    2280
aggcgagtgc gaattatgct ggtcactggc tgctacaggg cccgtttacc ggtctctcgt    2340
ggatagtcaa cgccacgtcg tccgcattca atatcacctc ccatgccttg accactgtcg    2400
gctctacact gtcatcactg gctgaggctt ggattccctt gggcggggcc tcacatcccc    2460
tcgctccttc cacaggcagt ttagcggcgg cgatcctagc gccgtgcgcc tcttgtgctc    2520
ctgccgcttg gtttagcgca gctcccatgc taggctgggc gtttcgctat cccacttggc    2580
acgagtccat tatggctctg cttttggtcc tgatttacat gaggttcgcc ggggtcgctc    2640
ggcttgccgc tctggttact tggaagttga ctcgcaactt cggcgctgtt ggtgtgctcg    2700
tcctcctagt gcttgcgcgt aggaagacca gtgctttggg gtacgagatc tgtatttccc    2760
ttacgggcga ggctgattgg gactggttgg atttttcctc ctggctcctc tcgcttctgt    2820
tcgcttgggc agtgcttgct ctcgcgtccc ttacaccagc aatgaagaag cgtaagctcc    2880
gatggtactc tcgctgggct tggtgctact ctcggttcat ctcgtgggtc gaccacactc    2940
cattcaacgg tgtagatccc cttctcgga aggcttccta ctactggctg tttgcgggtc    3000
tggtttggcc taacgaggtt gccgttgtgg ttgcctcgta cgtcttgatt gccgtcgtgg    3060
ttgacttgac tgacatttta ctagagaccc tcttgttgtc aaatcctgat ctgggaaggc    3120
tcgcggtgtt gtgtgacacc atcgcgggtc tcaggtctcc ctggttcctc cattgggttc    3180
tggagcgcgc agctaggcgt ggcatttacc tctatcacca ccaggggcat ttgtccgcac    3240
ggctcgcaca gtatctcagg gagttggatg gtgccttgga gccggcgcgg gttacgccgc    3300
aggactgcga gtttgtgcgc gacgctcagc ggattcttga gtgtggccgc aattatcgcg    3360
ggaaggcggt tgttgcccgc aacggtgaca ctgtcatcat ggcgccgttc gcgggggcct    3420
gggagctccc ccccgggttc gtgcttacgg ccccctcat gcttcgaagc gttggccgtg    3480
gagtctggca gacgctagtg acgagcatga tggggaagga caaggaagat cacacaggca    3540
atgtccttat ccttgggacc gctgccaccc ggtcaatggg gacgtgcgtc ggggggtgg    3600 tttacaccac attccactcc tccaacggtc ggactttggc tgggccaact gggcccctaa    3660
atcctcggtg gtggtcgccc tcggacgaca ccgccgtgta cccaatgcct gtaggctgca    3720
gaagtctaga gatttgtgga tgtggagccc ggagcgcatg ggtactgcgc aaggatggtg    3780
ctctagtcca cggtgaactg tttcctggac gtgagattag actggatgtc gctggtcgtg    3840
ttgcagactt taagggcgca tcaggttcac ccatactctg tgaccagggt catgccatgg    3900
gtatgttgac cgcggtgtcg catcggggc cggaagtaca ctcggccctc tttgtcaagc    3960
cgtgggacag cgttcccagg gatgcccaaa cggttacgga cgtgggtgca cctcctgcgg    4020
tacctggcaa aggcaactac gaggagcgat ccttgttctt gcccactggc actggcaagt    4080 ccaccccttgt ccctgccaat tatgccaagt caggccacaa gaccttggtt ctgaacccgt    4140
ctgttgccac tgttgccgcc atgggtcctt acatgaagga caaaatgggc attacaccgt    4200
ccatctttgc tggccatggg cccaccgcta tctcgcgcaa cactgggtct aacctggtgt    4260
acgcgactta cggtcgtttc ttggccaagc ataagcagtt gctggacggt gtctctgtta    4320
ttctttgtga tgagtgccac agctcagacc cgacagtatt gttgggtatt gggctggtgc    4380
gctctgaagc gaagaaggcc ggagtgaact tagttctctt cggtacagct acaccacctg    4440
```

```
gctatgctac agtccctcat aagaacatca cggaggcacc ggttgggacg gatggtgaca    4500
ttccattcta tggtttctac ttgaagtcca ctaactacac cactggcaga catctgatct    4560
ttgtccactc taagagtgag gcggagcgcg tcgcctccgc tcttactgct aagggcgtca    4620
aagctatgtt ccactactca ggtcgggatc caaccgcaat ccccaccact ggtagtttga    4680
ccgtagtagc caccgatgcc cttaacacag gatacacagg tgactttgat acggtgacgg    4740
actgcaatgt ggctgtgcag gaagaagtta ccgttgatct tgaacctacc ttcaccattt    4800
ctcttcgcac tcggccagct acggctgatc tgcgtgccca gaggaggggg cgttgcggtc    4860
gcggcaggcc tggcctgtac cgttactgta tagcctcttc cccgccttgt ggcacggtcc    4920 catccgggc cgtttgggcc gcttttgacg ctgcgctgac ttggtacgat attcagcccg    4980
ccgccgctgc gcggttgatt ggactttttg cagagtgccc ttacaccggg cacattggcg    5040
taaacttgca ggaccccag cgggtctatg aggtcctcgc tccgtttgcg ctgacgccag    5100
acgtagtgag agcaaggaac gccggggtca gctggcccct cctcgttgga gtccaacggt    5160
cagagtgcaa gcgctgcgcc tcaggtcctc cttccaacgc cccccactgg cagggtttgg    5220
tcggcgattg tgccgttccg ctgctttacg ccttggagac tcagaggccc gagagggtaa    5280
tccgatctcc attggtcgat caattggctg cggccttggg cgactctgtt acagagacgt    5340
cctctggccc catccttttg gccggcttgg cgttggctgc ggccgctgct attgctgact    5400
acaccgggac tttggtggtc gttgggacct ttgacgtgcg ccctgggggg gctccgcggc    5460
ctccccaatc gcgcgatctg cccggcggat tatcatcagg acagccacag agtgatggcg    5520
agggccctcc ccctccccgt cgcactgacc agctgacaga ctcccaaact ttggacgcac    5580
tccaggatgt gatgacccag acatcgtggg agtgtctgga ttattgctac cgggtagcga    5640
ccggtaccct ggctcctaga accgccgacg cgctggaaag cggggcgcgt tggcttcggg    5700
aggcgtgctg tgggactaac cctcccacta gtccattccc aggtgggtgg ggggtcaccc    5760 aaccctacc tctcggacac cttgctgtga aggcttggca aaccttgctc aacaacttgg    5820
gtactgctat ttccctggtc accgcggcct gggccgctgg tagttctcct ccgcttgctt    5880
gtatcgcctc agcgttgctt gggttgcaaa gcgcgttgcc gctcgacgtg cgcctcccgg    5940
ccgctctcct tgctggtgcc ggtggcactc tcttcggaga tgccgccact ggcttgggga    6000
tggccgcgtc gttcatgttg ggtggcacgg ttggaaccgc tggcccttt atgttcctac    6060 ttgaagtctt gggggggtat gagtcgacgg tggtcggcgc ctcccttgca tttgacctt    6120 tttctggaaa cgcttctatg tcagacttgg tttacctaat ccctgctctc ggctcacctg    6180
ggcccgcagt cgctggcttt gccgttggct tgttctcca cttggctctc ggtaaggctc    6240
cgtctcgggc ctggttgaac cgacttctta ctctttacc tcgctcggtc gctttacctc    6300
aggacttctt tttggaggag gacgtgaggg ctcgagcttc tgagctcctg cgttcccttt    6360
ctattagtcg ttctgtgtct aagctcctgg cttctgttgg tgacaagtac atcactcgta    6420
cctctggcag cctcttctgg gaggtcgcag ccactgtgat ctcctggttt aggcgcctgt    6480
tggactgggt cacctcctgc gtgaaggacc ggatgccctc tgttcctgtg cctatgttga    6540
cctgccaggc cgcttacact ggaccttggg ttggtactgg taccgtcact ggccgttgcg    6600
gctgtggcgc tgccatctct gctgacttcg aggagggtgt tcgcgttcgc tggcacacta    6660
cttcatattt ctgccgtggg tactttgccc gcggcattcc tctgaatact cttggcacta    6720
cttcaggtcc tcgcccggcc cccaagctcg tgggtcaccg gctatccat cccgtggggc    6780 ttactggcta cgttgaggtt ttgcgcgcgg aaactggtga ggtaacaatc actaggacta    6840
```

```
ccgagcatga tctcactcgt gaccaacttc tccacgcctt acgccagccg ccctaccagg    6900
tggatggtgt ggtctgttct ctccgctatt cggcttcact cattgccatg atttacggtt    6960
ctggtgccgt tgttgattac gaaggtcggg ccattaccct ccctcacacc gtccccggag    7020
atggcgtcaa tcccgagtat atcgggacgg tcgccctcga aggggatgct gtccgggagg    7080
ctatggctga accagaggtt tggcatgaca ccactgaccg ttttctgac agtgttgagc     7140
cggaagagct tgagcgcttg actctcggct ccgaggttga gttgcctccg ttggatccgg    7200
agggaccagg ggtcgttccg tctgagcgta ccttctttgt ggcttccaat ccgcaaggtg    7260
aggtcgccat cgagagggac gttgagacgc ttactccccc tattcctcct gttccccgt     7320
tggctccttt gcccacgagg ccggtggtct tgcctccacc tccttctgat tctggccctt    7380
tgggtacatc cgactaccca gctacctact ctgacaccgg ctctatgccg ccgttggagg    7440
gtgagctccg tggttcgggt gcatccactc ctattttctg gcaggaacct actcgtttct    7500
cccatgtgcc tacatctatt agcattgagt ctactgacag gtctatcgct caggggttgc    7560
tcgactccgt cggttcttcg gctgaggcat tggccgttgc tactgaagtt gttaatcgca    7620
gctttctcac acctgctctt tgccatgaag cgctccatgg ttctggcgcc ttggtggctt    7680
cactcccgcc gccggacccc gaggttgcct cggtcgcttc cacacccgag cctgacactg    7740
ttcatggcgc ggttgcggtg gcggcccaga cggcgttggg gactgttgcg gcggccttga    7800
cggctgccac tggcaatagt tccggggagg cttctcctgt gctccctgaa ccccaggtgc    7860
gggttgtgca cttgactgct ccttgtttca atcatgatgg ggatgttctt tgtacttcgg    7920
ctgacatcac cttggccgga gttttggtgc atgccggggg gcgttttaac caccggcaca    7980
gcttctgggt caatggtgtt aggcgcaggg gcaccactcg cgtggcgtcc ctgtgtgaca    8040
ctgctgtctc agttactgtt aggtgcaatt ctccctcggg ctcttcttgc agccaaacat    8100
cacttcctcc tgctgaacct gctgtgcgga gccctagccc taggccccg cgcggcgtgc     8160
acatcagttg gacttgctgc caaaatcgtt cctaccgtgg ttttactca ggaaacttta     8220
ccatttctga catttgtgat gggtttgcca tcttttccaga ctcctcccac ctcttcttcc    8280
atgggaaccg ggtgttgaca ctcgagactc gtgttgagga actggaggga gaacagattg    8340
agattcagta cacctgcaga catgagaccg aacccgtctc tcgctgcgtg aggtcgtaca    8400
tttggtacgg tgttccgcta cgggtcgtg agagccgccc tgtaccggtc acccgcccaa     8460
ttggatcctt catgcgcgcg gacgctactc gtgcttacgt cacgcagatg tctgaagttg    8520
ggaaccgtat tgagaaagtc accattgagc agacgattgc cttggaggat cagttcctta    8580
tggatcgcta caacttggcc cttgccaggg ctaagaatgg cggtccgtat cggggctggt    8640
cttatgaaga ggctgtggcc aaggttcgcc ctcgggctgc cgctggccat aacgtcaagc    8700
tctctgttgc cgatctcaaa acgcctgcgg gtcggaaaat cgtggaggac accatccagt    8760
ctattgctgt tgagcgtgat gaacatcctt tcatgcttac agctaagtct gaggtgtttt    8820
tccaagataa gaagactcgc aagccacctc ggctgctctg ttaccccctca ttggagttta    8880
gagtggctga gaaaatgatc ctaggcgacc ctggcttggt agccaaggcc gtcctgggtg    8940
atgcatatgg tttccagtac accccccaac aacgggttag aaaactactc tctctctggg    9000
atgagaagca aatacccatt gctatcacgg ttgacgccaa gtgctttgat tccaccatca    9060
cggcgtttga tgtcgaccga gaagctgaaa tctatgccat tgcccatgag aaaccagatc    9120
tggttcgcgc tctccatcgg cactataagg caggtcctat ggtgaaccgt gagggcgttg    9180
```

| | |
|---|---|
| aggttggtta ccgtaactgc cgcccatctg gcatttacac cacttctgct tctaattcca | 9240 |
| ttacttgctg gatcaaggtg ggtgccgcct gtcgtaagat aggccttagg aatccttcct | 9300 |
| tcctcatcca cggtgatgac tgtgtcatta tcgcggagag gggagacgag gaccctacac | 9360 |
| ctgcttgcg tgcagctttg ctggaatatg gtatgactc agatcctgca ctccacgctt | 9420 |
| cgctggacga ggcggagtca gcttccactt tcttggctga gtgcacggcg ggttacgacc | 9480 |
| gccgtaagat ttatttcctt tccactgact tccggaaggt acttgcgagg ctacgtctg | 9540 |
| agtacggaga cccggtcgct tctgcgtgtg gttacacctt gctctatccg tggcacccctt | 9600 |
| tgactaggtg ggtcctaatg gcgcaggtca ttggactccc cttttaagg ggtgcctcgg | 9660 |
| tggacgaggc aatcacgtgc gaggtggctg gtaaccgtct cacgtttcct ctcaagcagc | 9720 |
| tgccatccat cctggtggcc ctgcatggcc cggagtgctt gcgcgtcgtc tctgactcca | 9780 |
| ataagaccct cagggagaca aacaatgcgc ttcaggccct cagaatgcgg gggctttcct | 9840 |
| ggtaccggaa gaggactatt gctctcaggc ttaaaatgat cagagctggt gggcagtggg | 9900 |
| cgaagttggc caaggctctc atctggcctc cttctgccta catcccatcg ttggaggttg | 9960 |
| acaccttcga cgcaacccag ctttggaca ttatgagcag gccctataac aaccttgagc | 10020 |
| tccagattgg caagccgatt cgtcggtcgc tgactggact cttgtgtct aggatctgtt | 10080 |
| cttttttgg ttctgacatt cctgctacct tagccgaaag gtatgcactt ggtcttgttt | 10140 |
| tggtcggttg ggctctcgcc ggctactggc ttctgttctg ggtgtgagcc cctagtttac | 10200 |
| tagcacccctt tacagttttc ctactaaaca tgattgtttg ttagtccaag gcaacaggct | 10260 |
| tcggccgggg gagtagcgcc cccccctttg tgagctcgta ccccctttt ggggctgttc | 10320 |
| ctccctggga agaggagcag tacatccccg gctggcagcc gttaattgct acgtggtggt | 10380 |
| tatagcccgg caaggttaac aggggagta gtgcccccccc cgccccaact cgggtagcgc | 10440 |
| gtacgctcgt cggtcctccg acgttaaaga acctggcct | 10479 |

<210> SEQ ID NO 2
<211> LENGTH: 9567
<212> TYPE: DNA
<213> ORGANISM: Theiler's disease-associated virus

<400> SEQUENCE: 2

| | |
|---|---|
| atggcgccctt tcttgttgct ggttcttttg tgcggggccg gtgctatccg cgcccccgcc | 60 |
| tcacacaaat gttccttcaa aggccggttt tatctgtcaa actgctgtga tccaaaggac | 120 |
| atactgctct gcacttacga cttctgcgtt acccgcgttg gttgtcatgt gtgcacagaa | 180 |
| gtttgttgga acgtctctcg tcctggcatt tctgttcgac ccggttcagg tgatgtggag | 240 |
| cccgacctta aggggttctt ctcggtcgct gcggtgggtg gctatgctgc ctccctcatc | 300 |
| ggcctcggag agcctttttc tgtcggcttg cttggcctca ccatcctta ccgggttgat | 360 |
| actggggttc ctgacgggtt gcgttgcgac agaccttgca atgtgtcagt tcccgtttgg | 420 |
| ccctcgtccc tcgagggat gcgggtcttg tgggaagttg tctggggttt gctgtaccgc | 480 |
| attccgcaca tgatttgggc agcctttaac atcttcgatg tgtggttgtt gggtctagtc | 540 |
| atcctcctta ccctggaggg tcgctggcac ctggcgatca tgctcgtcct gccgctggc | 600 |
| ttgtctactt ctagtgctga acttgttggg gagccatggg actcatgcac ctgtaagggt | 660 |
| gttgtgggtc ttaggcacct taacgagact acttctccat gtctctgtga aaatggccct | 720 |
| tggtactatg atgctggtac gccaggcctc acctcttttcg agagggggg tggctactgt | 780 |
| ccttcccgat cggtccgcag gtccggatgc tcgctgtggt gccagtgggg atcgtgggtt | 840 |

```
actatctacc ctccctcctg gcctaacggc cggcattctt ggctctgtaa ttggcggtgt      900
tggtgcaatg gtcgccgatg ctggattacc tgcctcgttg acgcacgtcg acattggtgt      960
ggttcctgcg tccgcgattg ttgggctgag accgctgatg attctcttac cttcgggaac     1020
tgtggcactg gccctcgcgt cactgctaac ttaaccgctt tcccttttgca ctatggtcag     1080 aaatctactg ttgctttggc tactaaaatg gtcttgactg ctaaattaca accccttgtgg    1140 aggaatctta acactaccat tatgtgctca gttattcgga cttctgtcca ttgctttagt     1200
tgcatcggct tgccgtcgcc tcccgcgggt ttgtgggagc gtgtcccggg cgaacccatt     1260
tctgattgtg aaggcgtgca ggtttccact ggtaagcgga ctcccacatg cccaaccaag     1320
cagaggtgga atgctactgt gcacgtctgc cccggttacg ccttctactc tcccgcgtat     1380
gatgatggcg agcttcatgt tgctggctac tggcagtggc ttttggccgg acgcactatt     1440
cacttttggt ttcttgtaga tttcctgctt gtttacttgt tcttgatgca cctctctggt     1500
gcgcgcatca cccccttttt agccttggct ctttggattc acttgcgggg ggggtctttt    1560
ggatccccca ctccgatacc tggctgcaaa aataagaatg aagccatcca caactacaca     1620
cactgtgtcc aggctcttgg tcacgccatt agcgtggttg gtgaggcgag tgcgaattat     1680
gctggtcact ggctgctaca gggcccgttt accggtctct cgtggatagt caacgccacg     1740
tcgtccgcat tcaatatcac ctcccatgcc ttgaccactg tcggctctac actgtcatca     1800
ctggctgagg cttggattcc cttgggcggg gcctcacatc ccctcgctcc ttccacaggc     1860
agtttagcgg cggcgatcct agcgccgtgc gcctcttgtg ctcctgccgc ttggtttagc     1920
gcagctccca tgctaggctg ggcgtttcgc tatcccactt ggcacgagtc cattatggct     1980
ctgcttttgg tcctgattta catgaggttc gccggggtcg ctcggcttgc cgctctggtt     2040
acttggaagt tgactcgcaa cttcggcgct gttggtgtgc tcgtcctcct agtgcttgcg     2100
cgtaggaaga ccagtgcttt ggggtacgag atctgtattt cccttacggg cgaggctgat     2160
tgggactggt tggattttttc ctcctggctc ctctcgcttc tgttcgcttg ggcagtgctt     2220
gctctcgcgt cccttacacc agcaatgaag aagcgtaagc tccgatggta ctctcgctgg     2280
gcttggtgct actctcggtt catctcgtgg gtcgaccaca ctccattcaa cggtgtagat     2340
cccctttctc ggaaggcttc ctactactgg ctgtttgcgg gtctggtttg gcctaacgag     2400
gttgccgttg tggttgcctc gtacgtcttg attgccgtcg tggttgactt gactgacatt     2460
ttactagaga ccctcttgtt gtcaaatcct gatctgggaa ggctcgcggt gttgtgtgac     2520 accatcgcg gtctccaggtc tccctggttc tccattgggt tctggagcg cgcagctagg     2580 cgtggcattt acctctatca ccaccagggg catttgtccg cacggctcgc acagtatctc     2640
agggagttgg atggtgcctt ggagccgcg cgggttacgc cgcaggactg cgagtttgtg     2700
cgcgacgctc agcggattct tgagtgtggc cgcaattatc gcgggaaggc ggttgttgcc     2760
cgcaacggtg acactgtcat cattggcgcc gttcgcgggg cctgggagct cccccccggg    2820
ttcgtgctta cggcccccct catgcttcga agcgttggcc gtggagtctg gcagacgcta    2880
gtgacgagca tgatggggaa ggacaaggaa gatcacacag gcaatgtcct tatccttggg     2940
accgctgcca cccggtcaat ggggacgtgc gtcgggggg tggtttacac cacattccac    3000
tcctccaacg gtcggacttt ggctgggcca actgggcccc taaatcctcg gtggtggtcg     3060
ccctcggacg acaccgccgt gtacccaatg cctgtaggct gcagaagtct agagatttgt     3120
ggatgtggag cccggagcgc atgggtactg cgcaaggatg gtgctctagt ccacggtgaa     3180
```

```
ctgtttcctg gacgtgagat tagactggat gtcgctggtc gtgttgcaga ctttaagggc    3240
gcatcaggtt cacccatact ctgtgaccag ggtcatgcca tgggtatgtt gaccgcggtg    3300
tcgcatcggg ggccggaagt acactcggcc ctctttgtca agccgtggga cagcgttccc    3360
agggatgccc aaacggttac ggacgtgggt gcacctcctg cggtacctgg caaaggcaac    3420
tacgaggagc gatccttgtt cttgcccact ggcactggca agtccaccct tgtccctgcc    3480
aattatgcca agtcaggcca caagaccttg gttctgaacc cgtctgttgc cactgttgcc    3540
gccatgggtc cttacatgaa ggacaaaatg gcattacac cgtccatctt tgctggccat    3600
gggcccaccg ctatctcgcg caacactggg tctaacctgg tgtacgcgac ttacggtcgt    3660
ttcttggcca agcataagca gttgctggac ggtgtctctg ttattctttg tgatgagtgc    3720
cacagctcag acccgacagt attgttgggt attgggctgg tgcgctctga agcgaagaag    3780
gccggagtga acttagttct cttcggtaca gctacaccac ctggctatgc tacagtccct    3840
cataagaaca tcacggaggc accggttggg acggatggtg acattccatt ctatggtttc    3900
tacttgaagt ccactaacta caccactggc agacatctga tctttgtcca ctctaagagt    3960
gaggcggagc gcgtcgcctc cgctcttact gctaagggcg tcaaagctat gttccactac    4020
tcaggtcggg atccaaccgc aatccccacc actggtagtt tgaccgtagt agccaccgat    4080
gcccttaaca caggatacac aggtgacttt gatacggtga cggactgcaa tgtggctgtg    4140
caggaagaag ttaccgttga tcttgaacct accttcacca tttctcttcg cactcggcca    4200
gctacggctg atctgcgtgc ccagaggagg gggcgttgcg gtcgcggcag gcctggcctg    4260
taccgttact gtatagcctc ttccccgcct tgtggcacgg tcccatccgg ggccgtttgg    4320
gccgcttttg acgctgcgct gacttggtac gatattcagc ccgccgccgc tgcgcggttg    4380
attggacttt ttgcagagtg cccttacacc gggcacattg gcgtaaactt gcaggacccc    4440
cagcgggtct atgaggtcct cgctccgttt gcgctgacgc cagacgtagt gagagcaagg    4500
aacgccgggg tcagctggcc cctcctcgtt ggagtccaac ggtcagagtg caagcgctgc    4560
gcctcaggtc ctccttccaa cgccccccac tggcagggtt tggtcggcga ttgtgccgtt    4620
ccgctgcttt acgccttgga gactcagagg cccgagaggg taatccgatc tccattggtc    4680
gatcaattgg ctgcggcctt gggcgactct gttacagaga cgtcctctgg ccccatcctt    4740
ttggccggct tggcgttggc tgcggccgct gctattgctg actacaccgg gactttggtg    4800
gtcgttggga cctttgacgt gcgccctggg ggggctccgc ggcctcccca atcgcgcgat    4860
ctgcccggcg gattatcatc aggacagcca cagagtgatg gcgaggggcc tcccctccc    4920 cgtcgcactg accagctgac agactcccaa actttggacg cactccagga tgtgatgacc    4980
cagacatcgt gggagtgtct ggattattgc taccgggtag cgaccggtac cctggctcct    5040
agaaccgccg acgcgctgga aagcggggcg cgttggcttc gggaggcgtg ctgtgggact    5100
aaccctccca ctagtccatt cccaggtggg tgggggtca cccaacccct acctctcgga    5160
caccttgctg tgaaggcttg gcaaaccttg ctcaacaact gggtactgc tatttccctg    5220 gtcaccgcgg cctgggccgc tggtagttct cctccgcttg cttgtatcgc ctcagcgttg    5280
cttgggttgc aaagcgcgtt gccgctcgac gtgcgcctcc cggccgctct ccttgctggt    5340
gccggtggca ctctcttcgg agatgccgcc actggcttgg ggatggccgc gtcgttcatg    5400
ttgggtggca cggttggaac cgctggcccc ttcatgttcc tacttgaagt cttgggggg    5460 tatgagtcga cggtggtcgg cgcctccctt gcatttgacc ttttttctgg aaacgcttct    5520
atgtcagact tggtttacct aatccctgct ctcggctcac ctgggcccgc agtcgctggc    5580
```

```
tttgccgttg gctttgttct ccacttggct ctcggtaagg ctccgtctcg ggcctggttg    5640
aaccgacttc ttactctttt acctcgctcg gtcgctttac ctcaggactt cttttggag    5700 gaggacgtga gggctcgagc ttctgagctc ctgcgttccc tttctattag tcgttctgtg    5760
tctaagctcc tggcttctgt tggtgacaag tacatcactc gtacctctgg cagcctcttc    5820
tgggaggtcg cagccactgt gatctcctgg tttaggcgcc tgttggactg ggtcacctcc    5880
tgcgtgaagg accggatgcc ctctgttcct gtgcctatgt tgacctgcca ggccgcttac    5940
actggacctt gggttggtac tggtaccgtc actggccgtt gcggctgtgg cgctgccatc    6000
tctgctgact tcgaggaggg tgttcgcgtt cgctggcaca ctacttcata tttctgccgt    6060
gggtactttg cccgcggcat tcctctgaat actcttggca ctacttcagg tcctcgcccg    6120
gcccccaagc tcgtgggtca ccgggctatc catcccgtgg ggcttactgg ctacgttgag    6180
gttttgcgcg cggaaactgg tgaggtaaca atcactagga ctaccgagca tgatctcact    6240
cgtgaccaac ttctccacgc cttacgccag ccgccctacc aggtggatgg tgtggtctgt    6300
tctctccgct attcggcttc actcattgcc atgatttacg gttctggtgc cgttgttgat    6360
tacgaaggtc gggccattac cctccctcac accgtccccg gagatggcgt caatcccgag    6420
tatatcggga cggtcgccct cgaaggggat gctgtccggg aggctatggc tgaaccagag    6480
gtttggcatg acaccactga ccgttttcct gacagtgttg agccggaaga gcttgagcgc    6540
ttgactctcg gctccgaggt tgagttgcct ccgttggatc cggagggacc aggggtcgtt    6600
ccgtctgagc gtaccttctt tgtggcttcc aatccgcaag gtgaggtcgc catcgagagg    6660
gacgttgaga cgcttactcc ccctattcct cctgttcccc cgttggctcc tttgcccacg    6720
aggccggtgg tcttgcctcc acctccttct gattctggcc cttgggtac atccgactac    6780 ccagctacct actctgacac cggctctatg ccgccgttgg agggtgagct ccgtggttcg    6840
ggtgcatcca ctcctatttt ctggcaggaa cctactcgtt tctcccatgt gcctacatct    6900
attagcattg agtctactga caggtctatc gctcaggggt tgctcgactc cgtcggttct    6960
tcggctgagg cattggccgt tgctactgaa gttgttaatc gcagctttct cacacctgct    7020 cttttgccatg aagcgctcca tggttctggc gccttggtgg cttcactccc gccgccggac    7080
cccgaggttg cctcggtcgc ttccacaccc gagcctgaca ctgttcatgg cgcggttgcg    7140
gtggcggccc agacgcgtt ggggactgtt gcggcggcct tgacggctgc cactggcaat    7200
agttccgggg aggcttctcc tgtgctccct gaaccccagg tgcgggttgt gcacttgact    7260
gctccttgtt tcaatcatga tggggatgtt cttttgtactt cggctgacat caccttggcc    7320
ggagttttgg tgcatgccgg ggggcgtttt aaccaccggc acagcttctg ggtcaatggt    7380
gttaggcgca ggggcaccac tcgcgtggcg tccctgtgtg acactgctgt tcagttact    7440 gttaggtgca attctccctc gggctcttct tgcagccaaa catcacttcc tcctgctgaa    7500
cctgctgtgc ggagccctag ccctagggcc ccgcgcggcg tgcacatcag ttggacttgc    7560
tgccaaaatc gttcctaccg tggttttac tcaggaaact ttaccatttc tgacatttgt    7620
gatgggtttg ccatctttcc agactcctcc cacctcttct tccatgggaa ccgggtgttg    7680
acactcgaga ctcgtgttga ggaactggag ggagaacaga ttgagattca gtacacctgc    7740
agacatgaga ccgaacccgt ctctcgctgc gtgaggtcgt acatttggta cggtgttccg    7800
ctacgggtcg gtgagagccg ccctgtaccg gtcacccgcc caattggatc cttcatgcgc    7860
gcggacgcta ctcgtgctta cgtcacgcag atgtctgaag ttgggaaccg tattgagaaa    7920
```

```
gtcaccattg agcagacgat tgccttggag gatcagttcc ttatggatcg ctacaacttg    7980
gcccttgcca gggctaagaa tggcggtccg tatcggggct ggtcttatga agaggctgtg    8040
gccaaggttc gccctcgggc tgccgctggc cataacgtca agctctctgt tgccgatctc    8100
aaaacgcctg cgggtcggaa aatcgtggag gacaccatcc agtctattgc tggtgagcgt    8160
gatgaacatc ctttcatgct tacagctaag tctgaggtgt ttttccaaga taagaagact    8220
cgcaagccac ctcggctgct ctgttacccc tcattggagt ttagagtggc tgagaaaatg    8280
atcctaggcg accctggctt ggtagccaag gccgtcctgg gtgatgcata tggtttccag    8340
tacacccccc aacaacgggt tagaaaacta ctctctctct gggatgagaa gcaaataccc    8400
attgctatca cggttgacgc caagtgcttt gattccacca tcacggcgtt tgatgtcgac    8460
cgagaagctg aaatctatgc cattgcccat gagaaaccag atctggttcg cgctctccat    8520
cggcactata aggcaggtcc tatggtgaac cgtgagggcg ttgaggttgg ttaccgtaac    8580
tgccgcccat ctggcattta caccacttct gcttctaatt ccattacttg ctggatcaag    8640
gtgggtgccg cctgtcgtaa gataggcctt aggaatcctt ccttcctcat ccacggtgat    8700
gactgtgtca ttatcgcgga gaggggagac gaggaccctga cacctgcttt gcgtgcagct    8760
ttgctggaat atgggtatga ctcagatcct gcactccacg cttcgctgga cgaggcggag    8820
tcagcttcca ctttcttggc tgagtgcacg gcgggttacg accgccgtaa gatttatttc    8880
cttttccactg acttccggaa ggtacttgcg agggctacgt ctgagtacgg agacccggtc    8940
gcttctgcgt gtggttacac cttgctctat ccgtggcacc ctttgactag gtgggtccta    9000
atggcgcagg tcattggact ccccttttta aggggtgcct cggtggacga ggcaatcacg    9060
tgcgaggtgg ctggtaaccg tctcacgttt cctctcaagc agctgccatc catcctggtg    9120
gccctgcatg gccggagtg cttgcgcgtc gtctctgact ccaataagac cctcaggagag    9180
acaaacaatg cgcttcaggc cctcagaatg cgggggcttt cctggtaccg gaagaggact    9240
attgctctca ggcttaaaat gatcagagct ggtgggcagt gggcgaagtt ggccaaggct    9300
ctcatctggc ctccttctgc ctacatccca tcgttggagg ttgacacctt cgacgcaacc    9360
cagcttttgg acattatgag caggcccta aacaaccttg agctccagat tggcaagccg    9420
attcgtcggt cgctgactgg actctttgtg tctaggatct gttctttttt tggttctgac    9480
attcctgcta ccttagccga aaggtatgca cttggtcttg ttttggtcgg ttgggctctc    9540
gccggctact ggcttctgtt ctgggtg                                         9567
```

<210> SEQ ID NO 3
<211> LENGTH: 3189
<212> TYPE: PRT
<213> ORGANISM: Theiler's disease-associated virus

<400> SEQUENCE: 3

```
Met Ala Pro Phe Leu Leu Leu Val Leu Leu Cys Gly Ala Gly Ala Ile
1               5                   10                  15

Arg Ala Pro Ala Ser His Lys Cys Ser Phe Lys Gly Arg Phe Tyr Leu
            20                  25                  30

Ser Asn Cys Cys Asp Pro Lys Asp Ile Leu Leu Cys Thr Tyr Asp Phe
        35                  40                  45

Cys Val Thr Arg Val Gly Cys His Val Cys Thr Glu Val Cys Trp Asn
    50                  55                  60

Val Ser Arg Pro Gly Ile Ser Val Arg Pro Gly Ser Gly Asp Val Glu
65                  70                  75                  80
```

Pro Asp Leu Lys Gly Phe Phe Ser Val Ala Val Gly Gly Tyr Ala
             85                  90                  95

Ala Ser Leu Ile Gly Leu Gly Glu Pro Phe Ser Val Gly Leu Leu Gly
            100                 105                 110

Leu Thr Ile Leu Tyr Arg Val Asp Thr Gly Val Pro Asp Gly Leu Arg
            115                 120                 125

Cys Asp Arg Pro Cys Asn Val Ser Val Pro Val Trp Pro Ser Ser Leu
130                 135                 140

Glu Gly Met Arg Val Leu Trp Glu Val Val Trp Gly Leu Leu Tyr Arg
145                 150                 155                 160

Ile Pro His Met Ile Trp Ala Ala Phe Asn Ile Phe Asp Val Trp Leu
                165                 170                 175

Leu Gly Leu Val Ile Leu Leu Thr Leu Glu Gly Arg Trp His Leu Ala
            180                 185                 190

Ile Met Leu Val Leu Ala Ala Gly Leu Ser Thr Ser Ser Ala Glu Leu
            195                 200                 205

Val Gly Glu Pro Trp Asp Ser Cys Thr Cys Lys Gly Val Val Gly Leu
            210                 215                 220

Arg His Leu Asn Glu Thr Thr Ser Pro Cys Leu Cys Glu Asn Gly Pro
225                 230                 235                 240

Trp Tyr Tyr Asp Ala Gly Thr Pro Gly Leu Thr Ser Phe Glu Arg Gly
                245                 250                 255

Gly Gly Tyr Cys Pro Ser Arg Ser Val Arg Arg Ser Gly Cys Ser Leu
            260                 265                 270

Trp Cys Gln Trp Gly Ser Trp Val Thr Ile Tyr Pro Pro Ser Trp Pro
            275                 280                 285

Asn Gly Arg His Ser Trp Leu Cys Asn Trp Arg Cys Trp Cys Asn Gly
            290                 295                 300

Arg Arg Cys Trp Ile Thr Cys Leu Val Asp Ala Arg Arg His Trp Cys
305                 310                 315                 320

Gly Ser Cys Val Arg Asp Cys Trp Ala Glu Thr Ala Asp Asp Ser Leu
                325                 330                 335

Thr Phe Gly Asn Cys Gly Thr Gly Pro Arg Val Thr Ala Asn Leu Thr
            340                 345                 350

Ala Phe Pro Leu His Tyr Gly Gln Lys Ser Thr Val Ala Leu Ala Thr
            355                 360                 365

Lys Met Val Leu Thr Ala Lys Leu Gln Pro Leu Trp Arg Asn Leu Asn
370                 375                 380

Thr Thr Ile Met Cys Ser Val Ile Arg Thr Ser Val His Cys Phe Ser
385                 390                 395                 400

Cys Ile Gly Leu Pro Ser Pro Ala Gly Leu Trp Glu Arg Val Pro
                405                 410                 415

Gly Glu Pro Ile Ser Asp Cys Glu Gly Val Gln Val Ser Thr Gly Lys
            420                 425                 430

Arg Thr Pro Thr Cys Pro Thr Lys Gln Arg Trp Asn Ala Thr Val His
            435                 440                 445

Val Cys Pro Gly Tyr Ala Phe Tyr Ser Pro Ala Tyr Asp Asp Gly Glu
            450                 455                 460

Leu His Val Ala Gly Tyr Trp Gln Trp Leu Ala Gly Arg Thr Ile
465                 470                 475                 480

His Phe Trp Phe Leu Val Asp Phe Leu Val Tyr Leu Phe Leu Met
                485                 490                 495

His Leu Ser Gly Ala Arg Ile Thr Pro Phe Leu Ala Leu Ala Leu Trp

```
                    500                 505                 510
Ile His Leu Arg Gly Gly Val Phe Gly Ser Pro Thr Pro Ile Pro Gly
                515                 520                 525
Cys Lys Asn Lys Asn Glu Ala Ile His Asn Tyr Thr His Cys Val Gln
            530                 535                 540
Ala Leu Gly His Ala Ile Ser Val Val Gly Glu Ala Ser Ala Asn Tyr
545                 550                 555                 560
Ala Gly His Trp Leu Leu Gln Gly Pro Phe Thr Gly Leu Ser Trp Ile
                565                 570                 575
Val Asn Ala Thr Ser Ser Ala Phe Asn Ile Thr Ser His Ala Leu Thr
                580                 585                 590
Thr Val Gly Ser Thr Leu Ser Ser Leu Ala Glu Ala Trp Ile Pro Leu
            595                 600                 605
Gly Gly Ala Ser His Pro Leu Ala Pro Ser Thr Gly Ser Leu Ala Ala
            610                 615                 620
Ala Ile Leu Ala Pro Cys Ala Ser Cys Ala Pro Ala Ala Trp Phe Ser
625                 630                 635                 640
Ala Ala Pro Met Leu Gly Trp Ala Phe Arg Tyr Pro Thr Trp His Glu
                645                 650                 655
Ser Ile Met Ala Leu Leu Val Leu Ile Tyr Met Arg Phe Ala Gly
                660                 665                 670
Val Ala Arg Leu Ala Ala Leu Val Thr Trp Lys Leu Thr Arg Asn Phe
            675                 680                 685
Gly Ala Val Gly Val Leu Val Leu Val Leu Ala Arg Arg Lys Thr
            690                 695                 700
Ser Ala Leu Gly Tyr Glu Ile Cys Ile Ser Leu Thr Gly Glu Ala Asp
705                 710                 715                 720
Trp Asp Trp Leu Asp Phe Ser Ser Trp Leu Leu Ser Leu Leu Phe Ala
                725                 730                 735
Trp Ala Val Leu Ala Leu Ala Ser Leu Thr Pro Ala Met Lys Lys Arg
                740                 745                 750
Lys Leu Arg Trp Tyr Ser Arg Trp Ala Trp Cys Tyr Ser Arg Phe Ile
            755                 760                 765
Ser Trp Val Asp His Thr Pro Phe Asn Gly Val Asp Pro Leu Ser Arg
770                 775                 780
Lys Ala Ser Tyr Tyr Trp Leu Phe Ala Gly Leu Val Trp Pro Asn Glu
785                 790                 795                 800
Val Ala Val Val Ala Ser Tyr Val Leu Ile Ala Val Val Asp
                805                 810                 815
Leu Thr Asp Ile Leu Leu Glu Thr Leu Leu Leu Ser Asn Pro Asp Leu
                820                 825                 830
Gly Arg Leu Ala Val Leu Cys Asp Thr Ile Ala Gly Leu Arg Ser Pro
            835                 840                 845
Trp Phe Leu His Trp Val Leu Glu Arg Ala Ala Arg Gly Ile Tyr
            850                 855                 860
Leu Tyr His His Gln Gly His Leu Ser Ala Arg Leu Ala Gln Tyr Leu
865                 870                 875                 880
Arg Glu Leu Asp Gly Ala Leu Glu Pro Ala Arg Val Thr Pro Gln Asp
                885                 890                 895
Cys Glu Phe Val Arg Asp Ala Gln Arg Ile Leu Glu Cys Gly Arg Asn
                900                 905                 910
Tyr Arg Gly Lys Ala Val Val Ala Arg Asn Gly Asp Thr Val Ile Ile
            915                 920                 925
```

-continued

Gly Ala Val Arg Gly Ala Trp Glu Leu Pro Pro Gly Phe Val Leu Thr
930                 935                 940

Ala Pro Leu Met Leu Arg Ser Val Gly Arg Gly Val Trp Gln Thr Leu
945                 950                 955                 960

Val Thr Ser Met Met Gly Lys Asp Lys Glu Asp His Thr Gly Asn Val
            965                 970                 975

Leu Ile Leu Gly Thr Ala Ala Thr Arg Ser Met Gly Thr Cys Val Gly
            980                 985                 990

Gly Val Val Tyr Thr Thr Phe His Ser Ser Asn Gly Arg Thr Leu Ala
        995                 1000                1005

Gly Pro Thr Gly Pro Leu Asn Pro Arg Trp Trp Ser Pro Ser Asp
    1010                1015                1020

Asp Thr Ala Val Tyr Pro Met Pro Val Gly Cys Arg Ser Leu Glu
    1025                1030                1035

Ile Cys Gly Cys Gly Ala Arg Ser Ala Trp Val Leu Arg Lys Asp
    1040                1045                1050

Gly Ala Leu Val His Gly Glu Leu Phe Pro Gly Arg Glu Ile Arg
    1055                1060                1065

Leu Asp Val Ala Gly Arg Val Ala Asp Phe Lys Gly Ala Ser Gly
    1070                1075                1080

Ser Pro Ile Leu Cys Asp Gln Gly His Ala Met Gly Met Leu Thr
    1085                1090                1095

Ala Val Ser His Arg Gly Pro Glu Val His Ser Ala Leu Phe Val
    1100                1105                1110

Lys Pro Trp Asp Ser Val Pro Arg Asp Ala Gln Thr Val Thr Asp
    1115                1120                1125

Val Gly Ala Pro Pro Ala Val Pro Gly Lys Gly Asn Tyr Glu Glu
    1130                1135                1140

Arg Ser Leu Phe Leu Pro Thr Gly Thr Gly Lys Ser Thr Leu Val
    1145                1150                1155

Pro Ala Asn Tyr Ala Lys Ser Gly His Lys Thr Leu Val Leu Asn
    1160                1165                1170

Pro Ser Val Ala Thr Val Ala Ala Met Gly Pro Tyr Met Lys Asp
    1175                1180                1185

Lys Met Gly Ile Thr Pro Ser Ile Phe Ala Gly His Gly Pro Thr
    1190                1195                1200

Ala Ile Ser Arg Asn Thr Gly Ser Asn Leu Val Tyr Ala Thr Tyr
    1205                1210                1215

Gly Arg Phe Leu Ala Lys His Lys Gln Leu Leu Asp Gly Val Ser
    1220                1225                1230

Val Ile Leu Cys Asp Glu Cys His Ser Ser Asp Pro Thr Val Leu
    1235                1240                1245

Leu Gly Ile Gly Leu Val Arg Ser Glu Ala Lys Lys Ala Gly Val
    1250                1255                1260

Asn Leu Val Leu Phe Gly Thr Ala Thr Pro Pro Gly Tyr Ala Thr
    1265                1270                1275

Val Pro His Lys Asn Ile Thr Glu Ala Pro Val Gly Thr Asp Gly
    1280                1285                1290

Asp Ile Pro Phe Tyr Gly Phe Tyr Leu Lys Ser Thr Asn Tyr Thr
    1295                1300                1305

Thr Gly Arg His Leu Ile Phe Val His Ser Lys Ser Glu Ala Glu
    1310                1315                1320

```
Arg Val Ala Ser Ala Leu Thr Ala Lys Gly Val Lys Ala Met Phe
    1325                1330                1335

His Tyr Ser Gly Arg Asp Pro Thr Ala Ile Pro Thr Thr Gly Ser
    1340                1345                1350

Leu Thr Val Ala Thr Asp Ala Leu Asn Thr Gly Tyr Thr Gly
    1355                1360                1365

Asp Phe Asp Thr Val Thr Asp Cys Asn Val Ala Val Gln Glu Glu
    1370                1375                1380

Val Thr Val Asp Leu Glu Pro Thr Phe Thr Ile Ser Leu Arg Thr
    1385                1390                1395

Arg Pro Ala Thr Ala Asp Leu Arg Ala Gln Arg Arg Gly Arg Cys
    1400                1405                1410

Gly Arg Gly Arg Pro Gly Leu Tyr Arg Tyr Cys Ile Ala Ser Ser
    1415                1420                1425

Pro Pro Cys Gly Thr Val Pro Ser Gly Ala Val Trp Ala Ala Phe
    1430                1435                1440

Asp Ala Ala Leu Thr Trp Tyr Asp Ile Gln Pro Ala Ala Ala Ala
    1445                1450                1455

Arg Leu Ile Gly Leu Phe Ala Glu Cys Pro Tyr Thr Gly His Ile
    1460                1465                1470

Gly Val Asn Leu Gln Asp Pro Gln Arg Val Tyr Glu Val Leu Ala
    1475                1480                1485

Pro Phe Ala Leu Thr Pro Asp Val Val Arg Ala Arg Asn Ala Gly
    1490                1495                1500

Val Ser Trp Pro Leu Leu Val Gly Val Gln Arg Ser Glu Cys Lys
    1505                1510                1515

Arg Cys Ala Ser Gly Pro Pro Ser Asn Ala Pro His Trp Gln Gly
    1520                1525                1530

Leu Val Gly Asp Cys Ala Val Pro Leu Leu Tyr Ala Leu Glu Thr
    1535                1540                1545

Gln Arg Pro Glu Arg Val Ile Arg Ser Pro Leu Val Asp Gln Leu
    1550                1555                1560

Ala Ala Ala Leu Gly Asp Ser Val Thr Glu Thr Ser Ser Gly Pro
    1565                1570                1575

Ile Leu Leu Ala Gly Leu Ala Leu Ala Ala Ala Ala Ile Ala
    1580                1585                1590

Asp Tyr Thr Gly Thr Leu Val Val Val Gly Thr Phe Asp Val Arg
    1595                1600                1605

Pro Gly Gly Ala Pro Arg Pro Pro Gln Ser Arg Asp Leu Pro Gly
    1610                1615                1620

Gly Leu Ser Ser Gly Gln Pro Gln Ser Asp Gly Glu Gly Pro Pro
    1625                1630                1635

Pro Pro Arg Arg Thr Asp Gln Leu Thr Asp Ser Gln Thr Leu Asp
    1640                1645                1650

Ala Leu Gln Asp Val Met Thr Gln Thr Ser Trp Glu Cys Leu Asp
    1655                1660                1665

Tyr Cys Tyr Arg Val Ala Thr Gly Thr Leu Ala Pro Arg Thr Ala
    1670                1675                1680

Asp Ala Leu Glu Ser Gly Ala Arg Trp Leu Arg Glu Ala Cys Cys
    1685                1690                1695

Gly Thr Asn Pro Pro Thr Ser Pro Phe Pro Gly Gly Trp Gly Val
    1700                1705                1710

Thr Gln Pro Leu Pro Leu Gly His Leu Ala Val Lys Ala Trp Gln
```

```
                1715                1720                1725
Thr Leu Leu Asn Asn Leu Gly Thr Ala Ile Ser Leu Val Thr Ala
        1730                1735                1740
Ala Trp Ala Ala Gly Ser Ser Pro Pro Leu Ala Cys Ile Ala Ser
        1745                1750                1755
Ala Leu Leu Gly Leu Gln Ser Ala Leu Pro Leu Asp Val Arg Leu
        1760                1765                1770
Pro Ala Ala Leu Leu Ala Gly Ala Gly Thr Leu Phe Gly Asp
        1775                1780                1785
Ala Ala Thr Gly Leu Gly Met Ala Ala Ser Phe Met Leu Gly Gly
        1790                1795                1800
Thr Val Gly Thr Ala Gly Pro Phe Met Phe Leu Leu Glu Val Leu
        1805                1810                1815
Gly Gly Tyr Glu Ser Thr Val Val Gly Ala Ser Leu Ala Phe Asp
        1820                1825                1830
Leu Phe Ser Gly Asn Ala Ser Met Ser Asp Leu Val Tyr Leu Ile
        1835                1840                1845
Pro Ala Leu Gly Ser Pro Gly Pro Ala Val Ala Gly Phe Ala Val
        1850                1855                1860
Gly Phe Val Leu His Leu Ala Leu Gly Lys Ala Pro Ser Arg Ala
        1865                1870                1875
Trp Leu Asn Arg Leu Leu Thr Leu Leu Pro Arg Ser Val Ala Leu
        1880                1885                1890
Pro Gln Asp Phe Phe Leu Glu Glu Asp Val Arg Ala Arg Ala Ser
        1895                1900                1905
Glu Leu Leu Arg Ser Leu Ser Ile Ser Arg Ser Val Ser Lys Leu
        1910                1915                1920
Leu Ala Ser Val Gly Asp Lys Tyr Ile Thr Arg Thr Ser Gly Ser
        1925                1930                1935
Leu Phe Trp Glu Val Ala Ala Thr Val Ile Ser Trp Phe Arg Arg
        1940                1945                1950
Leu Leu Asp Trp Val Thr Ser Cys Val Lys Asp Arg Met Pro Ser
        1955                1960                1965
Val Pro Val Pro Met Leu Thr Cys Gln Ala Ala Tyr Thr Gly Pro
        1970                1975                1980
Trp Val Gly Thr Gly Thr Val Thr Gly Arg Cys Gly Cys Gly Ala
        1985                1990                1995
Ala Ile Ser Ala Asp Phe Glu Glu Gly Val Arg Val Arg Trp His
        2000                2005                2010
Thr Thr Ser Tyr Phe Cys Arg Gly Tyr Phe Ala Arg Gly Ile Pro
        2015                2020                2025
Leu Asn Thr Leu Gly Thr Thr Ser Gly Pro Arg Pro Ala Pro Lys
        2030                2035                2040
Leu Val Gly His Arg Ala Ile His Pro Val Gly Leu Thr Gly Tyr
        2045                2050                2055
Val Glu Val Leu Arg Ala Glu Thr Gly Glu Val Thr Ile Thr Arg
        2060                2065                2070
Thr Thr Glu His Asp Leu Thr Arg Asp Gln Leu Leu His Ala Leu
        2075                2080                2085
Arg Gln Pro Pro Tyr Gln Val Asp Gly Val Val Cys Ser Leu Arg
        2090                2095                2100
Tyr Ser Ala Ser Leu Ile Ala Met Ile Tyr Gly Ser Gly Ala Val
        2105                2110                2115
```

```
Val Asp Tyr Glu Gly Arg Ala Ile Thr Leu Pro His Thr Val Pro
2120                2125                2130

Gly Asp Gly Val Asn Pro Glu Tyr Ile Gly Thr Val Ala Leu Glu
2135                2140                2145

Gly Asp Ala Val Arg Glu Ala Met Ala Glu Pro Glu Val Trp His
2150                2155                2160

Asp Thr Thr Asp Arg Phe Ser Asp Ser Val Glu Pro Glu Glu Leu
2165                2170                2175

Glu Arg Leu Thr Leu Gly Ser Glu Val Glu Leu Pro Pro Leu Asp
2180                2185                2190

Pro Glu Gly Pro Gly Val Val Pro Ser Glu Arg Thr Phe Phe Val
2195                2200                2205

Ala Ser Asn Pro Gln Gly Glu Val Ala Ile Glu Arg Asp Val Glu
2210                2215                2220

Thr Leu Thr Pro Pro Ile Pro Pro Val Pro Pro Leu Ala Pro Leu
2225                2230                2235

Pro Thr Arg Pro Val Val Leu Pro Pro Pro Ser Asp Ser Gly
2240                2245                2250

Pro Leu Gly Thr Ser Asp Tyr Pro Ala Thr Tyr Ser Asp Thr Gly
2255                2260                2265

Ser Met Pro Pro Leu Glu Gly Glu Leu Arg Gly Ser Gly Ala Ser
2270                2275                2280

Thr Pro Ile Phe Trp Gln Glu Pro Thr Arg Phe Ser His Val Pro
2285                2290                2295

Thr Ser Ile Ser Ile Glu Ser Thr Asp Arg Ser Ile Ala Gln Gly
2300                2305                2310

Leu Leu Asp Ser Val Gly Ser Ser Ala Glu Ala Leu Ala Val Ala
2315                2320                2325

Thr Glu Val Val Asn Arg Ser Phe Leu Thr Pro Ala Leu Cys His
2330                2335                2340

Glu Ala Leu His Gly Ser Gly Ala Leu Val Ala Ser Leu Pro Pro
2345                2350                2355

Pro Asp Pro Glu Val Ala Ser Val Ala Ser Thr Pro Glu Pro Asp
2360                2365                2370

Thr Val His Gly Ala Val Val Ala Ala Gln Thr Ala Leu Gly
2375                2380                2385

Thr Val Ala Ala Ala Leu Thr Ala Ala Thr Gly Asn Ser Ser Gly
2390                2395                2400

Glu Ala Ser Pro Val Leu Pro Glu Pro Gln Val Arg Val Val His
2405                2410                2415

Leu Thr Ala Pro Cys Phe Asn His Asp Gly Asp Val Leu Cys Thr
2420                2425                2430

Ser Ala Asp Ile Thr Leu Ala Gly Val Leu Val His Ala Gly Gly
2435                2440                2445

Arg Phe Asn His Arg His Ser Phe Trp Val Asn Gly Val Arg Arg
2450                2455                2460

Arg Gly Thr Thr Arg Val Ala Ser Leu Cys Asp Thr Ala Val Ser
2465                2470                2475

Val Thr Val Arg Cys Asn Ser Pro Ser Gly Ser Ser Cys Ser Gln
2480                2485                2490

Thr Ser Leu Pro Pro Ala Glu Pro Ala Val Arg Ser Pro Ser Pro
2495                2500                2505
```

```
Arg Ala Pro Arg Gly Val His Ile Ser Trp Thr Cys Cys Gln Asn
    2510            2515                2520
Arg Ser Tyr Arg Gly Phe Tyr Ser Gly Asn Phe Thr Ile Ser Asp
    2525            2530                2535
Ile Cys Asp Gly Phe Ala Ile Phe Pro Asp Ser Ser His Leu Phe
    2540            2545                2550
Phe His Gly Asn Arg Val Leu Thr Leu Glu Thr Arg Val Glu Glu
    2555            2560                2565
Leu Glu Gly Glu Gln Ile Glu Ile Gln Tyr Thr Cys Arg His Glu
    2570            2575                2580
Thr Glu Pro Val Ser Arg Cys Val Arg Ser Tyr Ile Trp Tyr Gly
    2585            2590                2595
Val Pro Leu Arg Val Gly Glu Ser Arg Pro Val Pro Val Thr Arg
    2600            2605                2610
Pro Ile Gly Ser Phe Met Arg Ala Asp Ala Thr Arg Ala Tyr Val
    2615            2620                2625
Thr Gln Met Ser Glu Val Gly Asn Arg Ile Glu Lys Val Thr Ile
    2630            2635                2640
Glu Gln Thr Ile Ala Leu Glu Asp Gln Phe Leu Met Asp Arg Tyr
    2645            2650                2655
Asn Leu Ala Leu Ala Arg Ala Lys Asn Gly Gly Pro Tyr Arg Gly
    2660            2665                2670
Trp Ser Tyr Glu Glu Ala Val Ala Lys Val Arg Pro Arg Ala Ala
    2675            2680                2685
Ala Gly His Asn Val Lys Leu Ser Val Ala Asp Leu Lys Thr Pro
    2690            2695                2700
Ala Gly Arg Lys Ile Val Glu Asp Thr Ile Gln Ser Ile Ala Gly
    2705            2710                2715
Glu Arg Asp Glu His Pro Phe Met Leu Thr Ala Lys Ser Glu Val
    2720            2725                2730
Phe Phe Gln Asp Lys Lys Thr Arg Lys Pro Pro Arg Leu Leu Cys
    2735            2740                2745
Tyr Pro Ser Leu Glu Phe Arg Val Ala Glu Lys Met Ile Leu Gly
    2750            2755                2760
Asp Pro Gly Leu Val Ala Lys Ala Val Leu Gly Asp Ala Tyr Gly
    2765            2770                2775
Phe Gln Tyr Thr Pro Gln Gln Arg Val Arg Lys Leu Leu Ser Leu
    2780            2785                2790
Trp Asp Glu Lys Gln Ile Pro Ile Ala Ile Thr Val Asp Ala Lys
    2795            2800                2805
Cys Phe Asp Ser Thr Ile Thr Ala Phe Asp Val Asp Arg Glu Ala
    2810            2815                2820
Glu Ile Tyr Ala Ile Ala His Glu Lys Pro Asp Leu Val Arg Ala
    2825            2830                2835
Leu His Arg His Tyr Lys Ala Gly Pro Met Val Asn Arg Glu Gly
    2840            2845                2850
Val Glu Val Gly Tyr Arg Asn Cys Arg Pro Ser Gly Ile Tyr Thr
    2855            2860                2865
Thr Ser Ala Ser Asn Ser Ile Thr Cys Trp Ile Lys Val Gly Ala
    2870            2875                2880
Ala Cys Arg Lys Ile Gly Leu Arg Asn Pro Ser Phe Leu Ile His
    2885            2890                2895
Gly Asp Asp Cys Val Ile Ile Ala Glu Arg Gly Asp Glu Asp Pro
```

-continued

```
                2900                2905                2910

Thr Pro Ala Leu Arg Ala Ala Leu Leu Glu Tyr Gly Tyr Asp Ser
    2915                2920                2925

Asp Pro Ala Leu His Ala Ser Leu Asp Glu Ala Glu Ser Ala Ser
    2930                2935                2940

Thr Phe Leu Ala Glu Cys Thr Ala Gly Tyr Asp Arg Arg Lys Ile
    2945                2950                2955

Tyr Phe Leu Ser Thr Asp Phe Arg Lys Val Leu Ala Arg Ala Thr
    2960                2965                2970

Ser Glu Tyr Gly Asp Pro Val Ala Ser Ala Cys Gly Tyr Thr Leu
    2975                2980                2985

Leu Tyr Pro Trp His Pro Leu Thr Arg Trp Val Leu Met Ala Gln
    2990                2995                3000

Val Ile Gly Leu Pro Phe Leu Arg Gly Ala Ser Val Asp Glu Ala
    3005                3010                3015

Ile Thr Cys Glu Val Ala Gly Asn Arg Leu Thr Phe Pro Leu Lys
    3020                3025                3030

Gln Leu Pro Ser Ile Leu Val Ala Leu His Gly Pro Glu Cys Leu
    3035                3040                3045

Arg Val Val Ser Asp Ser Asn Lys Thr Leu Arg Glu Thr Asn Asn
    3050                3055                3060

Ala Leu Gln Ala Leu Arg Met Arg Gly Leu Ser Trp Tyr Arg Lys
    3065                3070                3075

Arg Thr Ile Ala Leu Arg Leu Lys Met Ile Arg Ala Gly Gly Gln
    3080                3085                3090

Trp Ala Lys Leu Ala Lys Ala Leu Ile Trp Pro Pro Ser Ala Tyr
    3095                3100                3105

Ile Pro Ser Leu Glu Val Asp Thr Phe Ala Thr Gln Leu Leu
    3110                3115                3120

Asp Ile Met Ser Arg Pro Tyr Asn Asn Leu Glu Leu Gln Ile Gly
    3125                3130                3135

Lys Pro Ile Arg Arg Ser Leu Thr Gly Leu Phe Val Ser Arg Ile
    3140                3145                3150

Cys Ser Phe Phe Gly Ser Asp Ile Pro Ala Thr Leu Ala Glu Arg
    3155                3160                3165

Tyr Ala Leu Gly Leu Val Leu Val Gly Trp Ala Leu Ala Gly Tyr
    3170                3175                3180

Trp Leu Leu Phe Trp Val
    3185
```

<210> SEQ ID NO 4
<211> LENGTH: 20
<212> TYPE: DNA
<213> ORGANISM: Theiler's disease-associated virus

<400> SEQUENCE: 4
agggttcttc gggtaaatcc                                           20

<210> SEQ ID NO 5
<211> LENGTH: 21
<212> TYPE: DNA
<213> ORGANISM: Theiler's disease-associated virus

<400> SEQUENCE: 5
ccctcggact gaattatagg c                                         21

<210> SEQ ID NO 6
<211> LENGTH: 20
<212> TYPE: DNA
<213> ORGANISM: Theiler's disease-associated virus

<400> SEQUENCE: 6
gctttccctt tgcactatgg 20

<210> SEQ ID NO 7
<211> LENGTH: 20
<212> TYPE: DNA
<213> ORGANISM: Theiler's disease-associated virus

<400> SEQUENCE: 7
caagccgatg caactaaagc 20

<210> SEQ ID NO 8
<211> LENGTH: 20
<212> TYPE: DNA
<213> ORGANISM: Theiler's disease-associated virus

<400> SEQUENCE: 8
ggctctttgg attcacttgc 20

<210> SEQ ID NO 9
<211> LENGTH: 20
<212> TYPE: DNA
<213> ORGANISM: Theiler's disease-associated virus

<400> SEQUENCE: 9
ccagtgacca gcataattcg 20

<210> SEQ ID NO 10
<211> LENGTH: 20
<212> TYPE: DNA
<213> ORGANISM: Theiler's disease-associated virus

<400> SEQUENCE: 10
atgccatggg tatgttgacc 20

<210> SEQ ID NO 11
<211> LENGTH: 20
<212> TYPE: DNA
<213> ORGANISM: Theiler's disease-associated virus

<400> SEQUENCE: 11
ctcctcgtag ttgcctttgc 20

<210> SEQ ID NO 12
<211> LENGTH: 21
<212> TYPE: DNA
<213> ORGANISM: Theiler's disease-associated virus

<400> SEQUENCE: 12
tgggagtgtc tggattattg c 21

<210> SEQ ID NO 13
<211> LENGTH: 20
<212> TYPE: DNA
<213> ORGANISM: Theiler's disease-associated virus

<400> SEQUENCE: 13
caaggtgtcc gagaggtagg 20

<210> SEQ ID NO 14
<211> LENGTH: 21
<212> TYPE: DNA
<213> ORGANISM: Theiler's disease-associated virus

<400> SEQUENCE: 14
tggtactggt accgtcactg g                                        21

<210> SEQ ID NO 15
<211> LENGTH: 20
<212> TYPE: DNA
<213> ORGANISM: Theiler's disease-associated virus

<400> SEQUENCE: 15
gcgaggacct gaagtagtgc                                          20

<210> SEQ ID NO 16
<211> LENGTH: 19
<212> TYPE: DNA
<213> ORGANISM: Theiler's disease-associated virus

<400> SEQUENCE: 16
ctcctgtgct ccctgaacc                                           19

<210> SEQ ID NO 17
<211> LENGTH: 20
<212> TYPE: DNA
<213> ORGANISM: Theiler's disease-associated virus

<400> SEQUENCE: 17
aacaccattg acccagaagc                                          20

<210> SEQ ID NO 18
<211> LENGTH: 20
<212> TYPE: DNA
<213> ORGANISM: Theiler's disease-associated virus

<400> SEQUENCE: 18
cttctgccta catcccatcg                                          20

<210> SEQ ID NO 19
<211> LENGTH: 20
<212> TYPE: DNA
<213> ORGANISM: Theiler's disease-associated virus

<400> SEQUENCE: 19 tgcataccttt tcggctaagg                                         20

<210> SEQ ID NO 20
<211> LENGTH: 18
<212> TYPE: DNA
<213> ORGANISM: Theiler's disease-associated virus

<400> SEQUENCE: 20
atgcggcggc gttattcc                                            18

<210> SEQ ID NO 21
<211> LENGTH: 24
<212> TYPE: DNA
<213> ORGANISM: Theiler's disease-associated virus

<400> SEQUENCE: 21

```
gctatcaatc tgtcaatcct gtcc                                            24

<210> SEQ ID NO 22
<211> LENGTH: 21
<212> TYPE: DNA
<213> ORGANISM: Theiler's disease-associated virus

<400> SEQUENCE: 22
cgggtaaacg gcgggagtaa c                                               21

<210> SEQ ID NO 23
<211> LENGTH: 24
<212> TYPE: DNA
<213> ORGANISM: Theiler's disease-associated virus

<400> SEQUENCE: 23
taggtaggga cagtgggaat ctcg                                            24

<210> SEQ ID NO 24
<211> LENGTH: 18
<212> TYPE: DNA
<213> ORGANISM: Theiler's disease-associated virus

<400> SEQUENCE: 24
caccacacct tctacaac                                                   18

<210> SEQ ID NO 25
<211> LENGTH: 18
<212> TYPE: DNA
<213> ORGANISM: Theiler's disease-associated virus

<400> SEQUENCE: 25
atctgggtca tcttctcg                                                   18

<210> SEQ ID NO 26
<211> LENGTH: 18
<212> TYPE: DNA
<213> ORGANISM: Theiler's disease-associated virus

<400> SEQUENCE: 26
gccatcacca tcttccag                                                   18

<210> SEQ ID NO 27
<211> LENGTH: 20
<212> TYPE: DNA
<213> ORGANISM: Theiler's disease-associated virus

<400> SEQUENCE: 27
gactccacaa catattcagc                                                 20

<210> SEQ ID NO 28
<211> LENGTH: 166
<212> TYPE: DNA
<213> ORGANISM: Theiler's disease-associated virus

<400> SEQUENCE: 28
agggttcttc gggtaaatcc cggcgcggtg ttttgggttc agggcagtag gggcagacgg      60
gccagcagtc gctggttcct ggtaccacca ccctatccgg acgacctccc tcacgaaagg     120
tcgccacggt ctgtggctcg acgacgccta taattcagtc cgaggg                    166

<210> SEQ ID NO 29
<211> LENGTH: 156
```

```
<212> TYPE: DNA
<213> ORGANISM: Theiler's disease-associated virus

<400> SEQUENCE: 29
gctttccctt tgcactatgg tcagaaatct actgttgctt tggctactaa aatggtcttg 60
actgctaaat tacaaccctt gtggaggaat cttaacacta ccattatgtg ctcagttatt 120
cggacttctg tccattgctt tagttgcatc ggcttg 156

<210> SEQ ID NO 30
<211> LENGTH: 166
<212> TYPE: DNA
<213> ORGANISM: Theiler's disease-associated virus
<400> SEQUENCE: 30
ggctctttgg attcacttgc gggggggggt ctttggatcc cccactccga tacctggctg 60
caaaaataag aatgaagcca tccacaacta cacacactgt gtccaggctc ttggtcacgc 120
cattagcgtg gttggtgagg cgagtgcgaa ttatgctggt cactgg 166

<210> SEQ ID NO 31
<211> LENGTH: 155
<212> TYPE: DNA
<213> ORGANISM: Theiler's disease-associated virus
<400> SEQUENCE: 31
atgccatggg tatgttgacc gcggtgtcgc atcgggggcc ggaagtacac tcggccctct 60
ttgtcaagcc gtgggacagc gttcccaggg atgcccaaac ggttacggac gtgggtgcac 120
ctcctgcggt acctggcaaa ggcaactacg aggag 155

<210> SEQ ID NO 32
<211> LENGTH: 178
<212> TYPE: DNA
<213> ORGANISM: Theiler's disease-associated virus
<400> SEQUENCE: 32
tgggagtgtc tggattattg ctaccgggta gcgaccggta ccctggctcc tagaaccgcc 60
gacgcgctgg aaagcggggc gcgttggctt cgggaggcgt gctgtgggac taaccctccc 120
actagtccat tcccaggtgg gtggggggtc acccaacccc tacctctcgg acaccttg 178

<210> SEQ ID NO 33
<211> LENGTH: 163
<212> TYPE: DNA
<213> ORGANISM: Theiler's disease-associated virus
<400> SEQUENCE: 33
tggtactggt accgtcactg gccgttgcgg ctgtggcgct gccatctctg ctgacttcga 60
ggagggtgtt cgcgttcgct ggcacactac ttcatatttc tgccgtgggt actttgcccg 120
cggcattcct ctgaatactc ttggcactac ttcaggtcct cgc 163

<210> SEQ ID NO 34
<211> LENGTH: 167
<212> TYPE: DNA
<213> ORGANISM: Theiler's disease-associated virus
<400> SEQUENCE: 34
ctcctgtgct ccctgaaccc caggtgcggg ttgtgcactt gactgctcct tgtttcaatc 60
atgatgggga tgttctttgt acttcggctg acatcacctt ggccggagtt ttggtgcatg 120
```

```
ccgggggggcg ttttaaccac cggcacagct tctgggtcaa tggtgtt            167
```

<210> SEQ ID NO 35
<211> LENGTH: 197
<212> TYPE: DNA
<213> ORGANISM: Theiler's disease-associated virus

<400> SEQUENCE: 35

```
cttctgccta catcccatcg ttggaggttg acaccttcga cgcaacccag cttttggaca    60
ttatgagcag gccctataac aaccttgagc tccagattgg caagccgatt cgtcggtcgc   120
tgactggact ctttgtgtct aggatctgtt cttttttttgg ttctgacatt cctgctacct   180
tagccgaaag gtatgca                                                   197
```

<210> SEQ ID NO 36
<211> LENGTH: 18
<212> TYPE: DNA
<213> ORGANISM: Theiler's disease-associated virus

<400> SEQUENCE: 36

```
cgtaagggcg cgtagtgg                                                   18
```

<210> SEQ ID NO 37
<211> LENGTH: 18
<212> TYPE: DNA
<213> ORGANISM: Theiler's disease-associated virus

<400> SEQUENCE: 37

```
ccgaagcatc aaggaacc                                                   18
```

<210> SEQ ID NO 38
<211> LENGTH: 20
<212> TYPE: DNA
<213> ORGANISM: Theiler's disease-associated virus

<400> SEQUENCE: 38

```
acacattgca aggtctgtcg                                                 20
```

<210> SEQ ID NO 39
<211> LENGTH: 20
<212> TYPE: DNA
<213> ORGANISM: Theiler's disease-associated virus

<400> SEQUENCE: 39

```
acacattgca aggtctgtcg                                                 20
```

<210> SEQ ID NO 40
<211> LENGTH: 20
<212> TYPE: DNA
<213> ORGANISM: Theiler's disease-associated virus

<400> SEQUENCE: 40

```
aacaccgcca attacagagc                                                 20
```

<210> SEQ ID NO 41
<211> LENGTH: 20
<212> TYPE: DNA
<213> ORGANISM: Theiler's disease-associated virus

<400> SEQUENCE: 41

```
aaccgagagt agcaccaagc                                                 20
```

```
<210> SEQ ID NO 42
<211> LENGTH: 20
<212> TYPE: DNA
<213> ORGANISM: Theiler's disease-associated virus
<400> SEQUENCE: 42
caaatcctga tctgggaagg 20

<210> SEQ ID NO 43
<211> LENGTH: 20
<212> TYPE: DNA
<213> ORGANISM: Theiler's disease-associated virus
<400> SEQUENCE: 43
cccaaggata aggacattgc 20

<210> SEQ ID NO 44
<211> LENGTH: 20
<212> TYPE: DNA
<213> ORGANISM: Theiler's disease-associated virus
<400> SEQUENCE: 44
tttgtgatga gtgccacagc 20

<210> SEQ ID NO 45
<211> LENGTH: 20
<212> TYPE: DNA
<213> ORGANISM: Theiler's disease-associated virus
<400> SEQUENCE: 45
gcgaagagaa atggtgaagg 20

<210> SEQ ID NO 46
<211> LENGTH: 20
<212> TYPE: DNA
<213> ORGANISM: Theiler's disease-associated virus
<400> SEQUENCE: 46
gttctgaacc cgtctgttgc 20

<210> SEQ ID NO 47
<211> LENGTH: 20
<212> TYPE: DNA
<213> ORGANISM: Theiler's disease-associated virus
<400> SEQUENCE: 47
cagcaactgc ttatgcttgg 20

<210> SEQ ID NO 48
<211> LENGTH: 20
<212> TYPE: DNA
<213> ORGANISM: Theiler's disease-associated virus
<400> SEQUENCE: 48
acccaagttg ttgagcaagg 20

<210> SEQ ID NO 49
<211> LENGTH: 20
<212> TYPE: DNA
<213> ORGANISM: Theiler's disease-associated virus
<400> SEQUENCE: 49
tacactggac cttgggttgg 20
```

<210> SEQ ID NO 50
<211> LENGTH: 21
<212> TYPE: DNA
<213> ORGANISM: Theiler's disease-associated virus

<400> SEQUENCE: 50
caccagaacc gtaaatcatg g 21

<210> SEQ ID NO 51
<211> LENGTH: 20
<212> TYPE: DNA
<213> ORGANISM: Theiler's disease-associated virus

<400> SEQUENCE: 51
gagcagtcaa gtgcacaacc 20

<210> SEQ ID NO 52
<211> LENGTH: 20
<212> TYPE: DNA
<213> ORGANISM: Theiler's disease-associated virus

<400> SEQUENCE: 52
ttgccatctt tccagactcc 20

<210> SEQ ID NO 53
<211> LENGTH: 20
<212> TYPE: DNA
<213> ORGANISM: Theiler's disease-associated virus

<400> SEQUENCE: 53
ataagaccag ccccgatacg 20

<210> SEQ ID NO 54
<211> LENGTH: 20
<212> TYPE: DNA
<213> ORGANISM: Theiler's disease-associated virus

<400> SEQUENCE: 54
gtcaaccgtg atagcaatgg 20

<210> SEQ ID NO 55
<211> LENGTH: 20
<212> TYPE: DNA
<213> ORGANISM: Theiler's disease-associated virus

<400> SEQUENCE: 55 actcccctg ttaaccttgc 20

<210> SEQ ID NO 56
<211> LENGTH: 19
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (14)..(19)
<223> OTHER INFORMATION: N at positions 14-19 may be any naturally-
occuring nucleotide

<400> SEQUENCE: 56
gctcttccga tctnnnnnn 19

<210> SEQ ID NO 57

```
<211> LENGTH: 13
<212> TYPE: DNA
<213> ORGANISM: Artificial Sequence
<220> FEATURE:
<223> OTHER INFORMATION: Synthetic construct

<400> SEQUENCE: 57
gctcttccga tct                                                        13

<210> SEQ ID NO 58
<211> LENGTH: 58
<212> TYPE: DNA
<213> ORGANISM: Artificial Sequence
<220> FEATURE:
<223> OTHER INFORMATION: Synthetic construct

<400> SEQUENCE: 58
aatgatacgg cgaccaccga gatctacact ctttccctac acgacgctct tccgatct      58

<210> SEQ ID NO 59
<211> LENGTH: 65
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (25)..(31)
<223> OTHER INFORMATION: N at positions 25-31 may be any naturally-
      occuring nucleotide

<400> SEQUENCE: 59
caagcagaag acggcatacg agatnnnnnn ngtgactgga gttcagacgt gtgctcttcc    60
gatct                                                                65

<210> SEQ ID NO 60
<211> LENGTH: 18
<212> TYPE: DNA
<213> ORGANISM: Artificial Sequence
<220> FEATURE:
<223> OTHER INFORMATION: Synthetic construct

<400> SEQUENCE: 60
aatgatacgg cgaccacc                                                   18

<210> SEQ ID NO 61
<211> LENGTH: 19
<212> TYPE: DNA
<213> ORGANISM: Artificial Sequence
<220> FEATURE:
<223> OTHER INFORMATION: Synthetic construct

<400> SEQUENCE: 61
caagcagaag acggcatac                                                  19

<210> SEQ ID NO 62
<211> LENGTH: 23
<212> TYPE: DNA
<213> ORGANISM: Artificial Sequence
<220> FEATURE:
<223> OTHER INFORMATION: Artificial construct

<400> SEQUENCE: 62
aatgatacgg cgaccaccga gat                                             23

<210> SEQ ID NO 63
```

```
<211> LENGTH: 21
<212> TYPE: DNA
<213> ORGANISM: Artificial Sequence
<220> FEATURE:
<223> OTHER INFORMATION: Synthetic construct

<400> SEQUENCE: 63
caagcagaag acggcatacg a                                              21
```